United States Patent
Arguelles Delgado et al.

(10) Patent No.: US 11,926,634 B2
(45) Date of Patent: Mar. 12, 2024

(54) PROCESSES FOR THE PREPARATION OF SELECTIVE ESTROGEN RECEPTOR DEGRADERS

(71) Applicant: Eli Lilly and Company, Indianapolis, IN (US)

(72) Inventors: Alonso Jose Arguelles Delgado, Indianapolis, IN (US); Boris Arnoldovich Czeskis, Carmel, IN (US); Mai Khanh Nguyen Hawk, Indianapolis, IN (US); Douglas Patton Kjell, West Lafayette, IN (US); Yu Lu, Zionsville, IN (US); Nicholas Andrew Magnus, Indianapolis, IN (US); David Michael Remick, Fishers, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 18/160,457

(22) Filed: Jan. 27, 2023

(65) Prior Publication Data
US 2023/0242545 A1    Aug. 3, 2023

Related U.S. Application Data

(60) Provisional application No. 63/409,060, filed on Sep. 22, 2022, provisional application No. 63/305,520, filed on Feb. 1, 2022.

(51) Int. Cl.
C07D 491/052 (2006.01)
B01J 23/44 (2006.01)

(52) U.S. Cl.
CPC .......... *C07D 491/052* (2013.01); *B01J 23/44* (2013.01)

(58) Field of Classification Search
CPC ....... C07D 491/052; A61P 35/00; B01J 23/44
See application file for complete search history.

(56) References Cited

U.S. PATENT DOCUMENTS 10,654,866 B2 * 5/2020 Bastian ................ C07D 401/12
11,014,915 B2 * 5/2021 Pal ....................... C07D 405/10

OTHER PUBLICATIONS

Taylor, Moddie D., Louis R. Grant, and Clifton A. Sands. "A convenient preparation of pyridine-borane." *Journal of the American Chemical Society* 77, No. 6 (1955): 1506-1507.
Vo, Lanchi, James Ciula, and Owen W. Gooding. "Chemical development on the chiral auxiliary (S)-4-(phenylmethyl)-2-oxazolidinone utilizing automated synthesis and DoE." *Organic process research & development* 7, No. 4 (2003): 514-520.

* cited by examiner

*Primary Examiner* — Sikarl A Witherspoon
(74) *Attorney, Agent, or Firm* — Bradley W. Crawford

(57) ABSTRACT

Disclosed are methods of making selective estrogen receptor degraders (SERDs) of Formula A, as well as intermediates thereof, salts thereof including a pharmaceutically acceptable salt, and pharmaceutical compositions thereof:

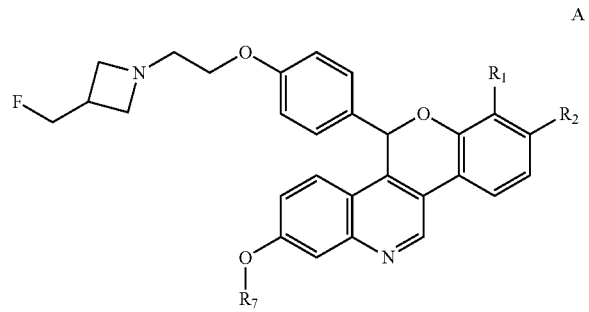

A wherein either $R_1$ or $R_2$ is independently Cl, F, —$CF_3$, or —$CH_3$, and the other is H; and $R_7$ is H or PG.

20 Claims, 3 Drawing Sheets

PROCESSES FOR THE PREPARATION OF SELECTIVE ESTROGEN RECEPTOR DEGRADERS

BACKGROUND

Selective estrogen receptor degraders (SERDs) bind to the estrogen receptor (ER) and downregulate ER-mediated transcriptional activity. The degradation and downregulation caused by SERDs can be useful in the treatment of various proliferative immune mediated disorders, cell proliferation disorders, including cancers such as breast cancer, ovarian cancer, endometrial cancer, prostate cancer, uterine cancer, gastric cancer, and lung cancer as well as mutations due to emerging resistance. Some small molecule examples of SERDs have been disclosed in the literature (see, e.g., WO2005073204, WO2014205136, and WO2016097071). Nonetheless, there is a need for new SERDs to treat ER-positive cancers, such as breast cancer, gastric cancer, and/or lung cancer.

As described in U.S. Pat. No. 10,654,866 (the '866 patent) a series of SERDs of the following formula have been discovered, along with pharmaceutically acceptable salts thereof:

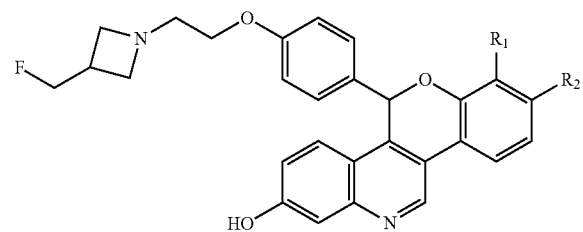

wherein one of $R_1$ and $R_2$ are independently Cl, F, —$CF_3$, or —$CH_3$, and the other is H. These SERDs are effective inhibitors of cell proliferation and generally exhibit better pharmacokinetic (PK) and pharmacodynamic (PD) properties relative to other known and characterized SERDs.

The '866 patent describes synthetic methods for preparing these compounds that utilize the following intermediates:

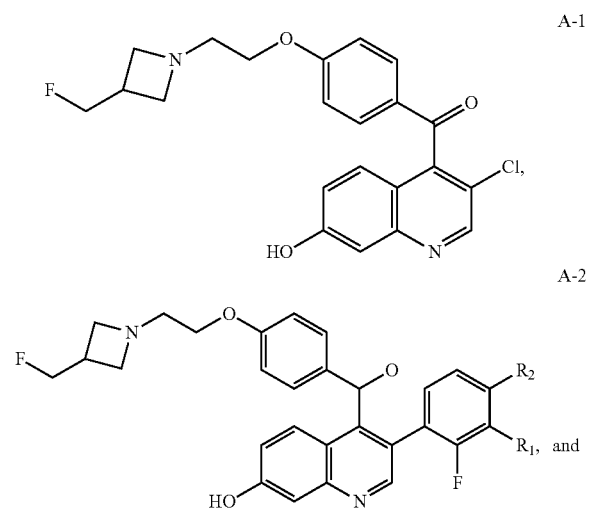

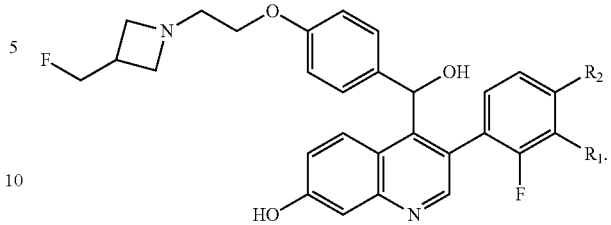

Where $R_1$ or $R_2$ is independently Cl, F, $CF_3$, or —$CH_3$, and the other is hydrogen. These intermediates bind to the estrogen receptor (ER) and downregulate ER-mediated transcriptional activity, and therefore are SERD active intermediates. Since these intermediates are SERD active, their use required special conditions, such as the use of high containment facilities, which are expensive and limited in number.

Disclosed herein are new methods and intermediates that avoid the use of the SERD active intermediates. Furthermore, the likelihood of SERD active contaminants is greatly reduced, and high containment facilities are not required. These new methods provide an efficient, cost-effective, and facile synthesis of SERD active compounds that utilize ecologically friendly reagents, allow for optimal impurity control, and form crystalline materials. The crystalline materials allow for facile purification of the SERD active compounds.

Further, novel intermediates useful in the preparation of SERD active compounds, such as those of Formula A (below), and pharmaceutically acceptable salts thereof, are also disclosed. The methods disclosed herein minimize the presence of the SERD active intermediates and impurities, and therefore also minimizes the need to use high potency/high containment manufacturing conditions. This greatly improves the efficiency and safety of the methods of making the compounds of Formula A, while reducing manufacturing costs.

SUMMARY

Disclosed herein are processes for preparing a compound of Formula A:

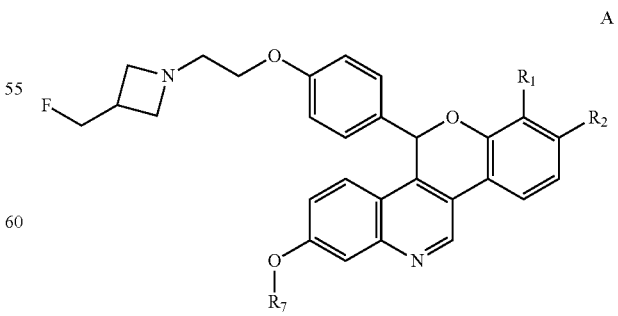

or a pharmaceutically acceptable salt thereof, wherein either $R_1$ or $R_2$ is independently Cl, F, —$CF_3$, or —$CH_3$, and the other is H; and $R_7$ is H or PG, wherein the process comprises reacting a compound of structure 8:

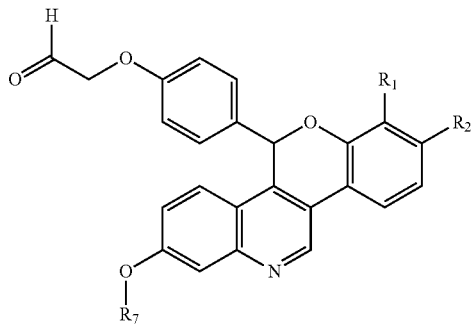

or a salt thereof, wherein $R_7$ is PG or H; wherein PG is an alcohol protecting group, in a solvent with an amine of structure 9

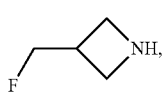

or a salt thereof, and a reducing agent. Suitable reducing reagents are disclosed elsewhere, in this application.

Intermediates useful in preparing the compounds of Formula A are also disclosed herein.

Disclosed herein are compounds of Formula A

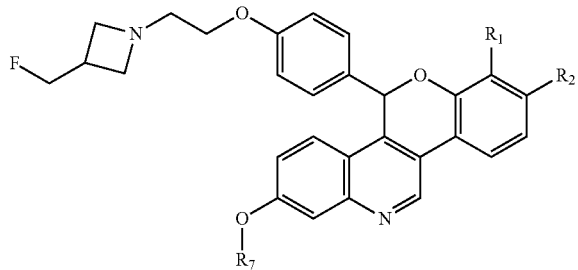

or a pharmaceutically acceptable salt thereof, wherein either $R_1$ or $R_2$ is independently Cl, F, —$CF_3$, or —$CH_3$, and the other is H; and $R_7$ is H or PG, obtainable by reacting a compound of structure 8:

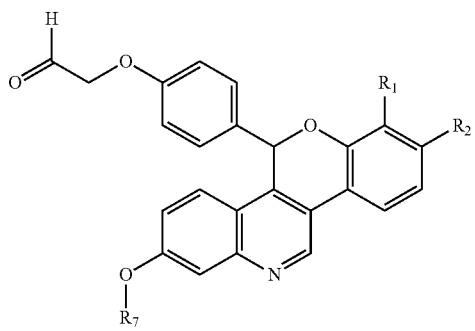

or a salt thereof, in a solvent with an amine of structure 9

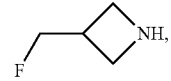

or a salt thereof, and a reducing agent. Suitable reducing reagents are disclosed elsewhere, in this application.

Disclosed herein are compounds of Formula A

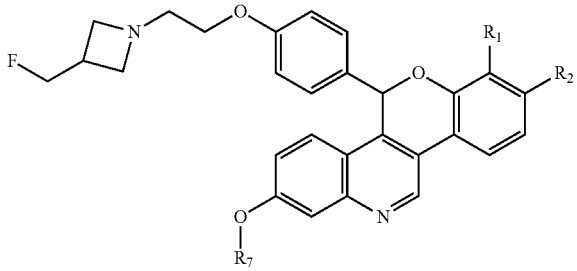

or pharmaceutically acceptable salts thereof, wherein either $R_1$ or $R_2$ is independently Cl, F, —$CF_3$, or —$CH_3$, and the other is H; and $R_7$ is H or PG, obtainable by reacting a compound of structure 8:

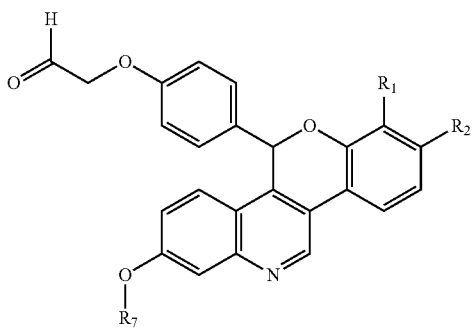

or a salt thereof, in a solvent with an amine of structure 9

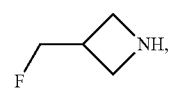

or a salt thereof, and a reducing agent, wherein the compounds of Formula A have an enantiomeric excess of at least about 92%.

Disclosed herein are compounds of Formula A

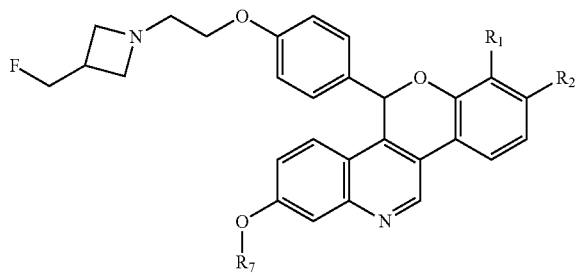

or a pharmaceutically acceptable salt thereof, wherein either $R_1$ or $R_2$ is independently Cl, F, —$CF_3$, or —$CH_3$, and the other is H; and $R_7$ is H or PG, which contain a $C_3$-$C_7$ alcohol. The compounds of Formula A can be prepared using the methods disclosed herein.

Disclosed herein are compounds of Formula A

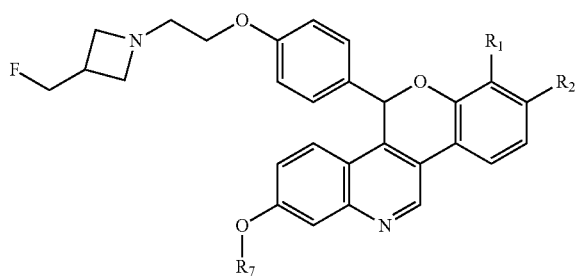

or a pharmaceutically acceptable salt thereof, wherein either $R_1$ or $R_2$ is independently Cl, F, —$CF_3$, or —$CH_3$, and the other is H; and $R_7$ is H or PG, obtainable by reacting a compound of structure 8:

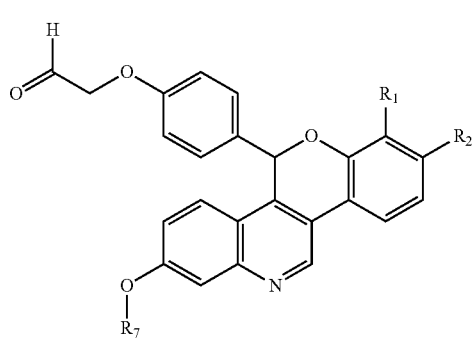

or a salt thereof, in a solvent with an amine of structure 9

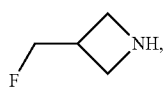

Or a salt thereof, and a reducing agent, wherein the compound of Formula A contains a $C_3$-$C_7$ alcohol.

Disclosed herein are compounds of Formula A

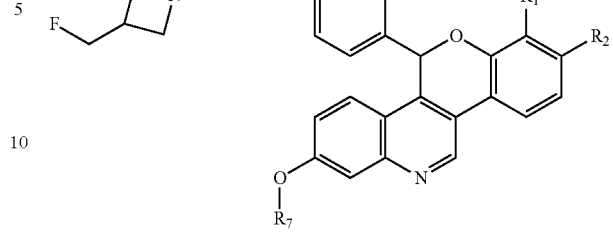

or a pharmaceutically acceptable salt thereof, wherein either $R_1$ or $R_2$ is independently Cl, F, —$CF_3$, or —$CH_3$, and the other is H; and $R_7$ is H or PG, having a purity of at least 98% area and containing less than 1% area of one or more dihydroquinoline or quinoline based impurities, which are defined below. The compounds of Formula A can be prepared using the methods disclosed herein.

Disclosed herein are compounds of Formula A

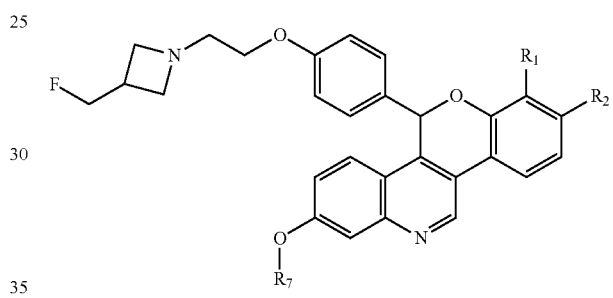

or a pharmaceutically acceptable salt thereof, wherein either $R_1$ or $R_2$ is independently Cl, F, —$CF_3$, or —$CH_3$, and the other is H; and $R_7$ is H or PG, obtainable by reacting a compound of structure 8:

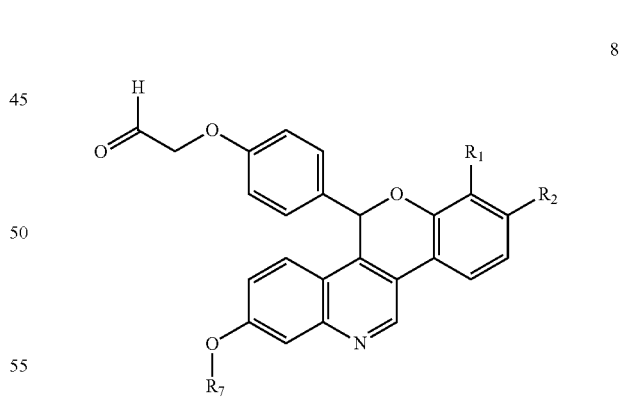

or a salt thereof, in a solvent with an amine of structure 9

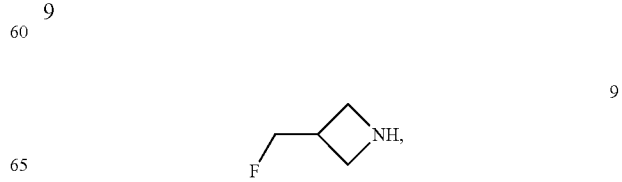

Or a salt thereof, and a reducing agent, wherein the compound of Formula A has a purity of at least 98% area and containing less than 1% area of one or more dihydroquinoline or quinoline based impurities, which are defined below.

Disclosed herein are compounds of Formula B

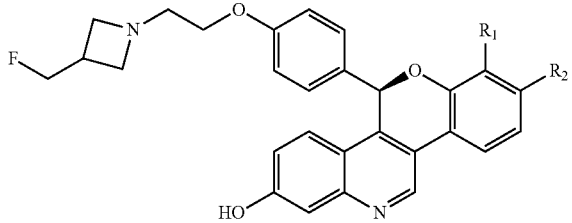

or a pharmaceutically acceptable salt thereof, wherein either $R_1$ or $R_2$ is independently Cl, F, —$CF_3$, or —$CH_3$, and the other is H; and $R_7$ is H or PG, having a purity of at least 98% area containing less than 1% area of one or more dihydroquinoline or quinoline based impurities.

Also disclosed herein is a process for preparing pyridine borane, the process comprising: reacting a pyridinium salt and sodium borohydride in a solvent.

DETAILED DESCRIPTION

Figure 1:
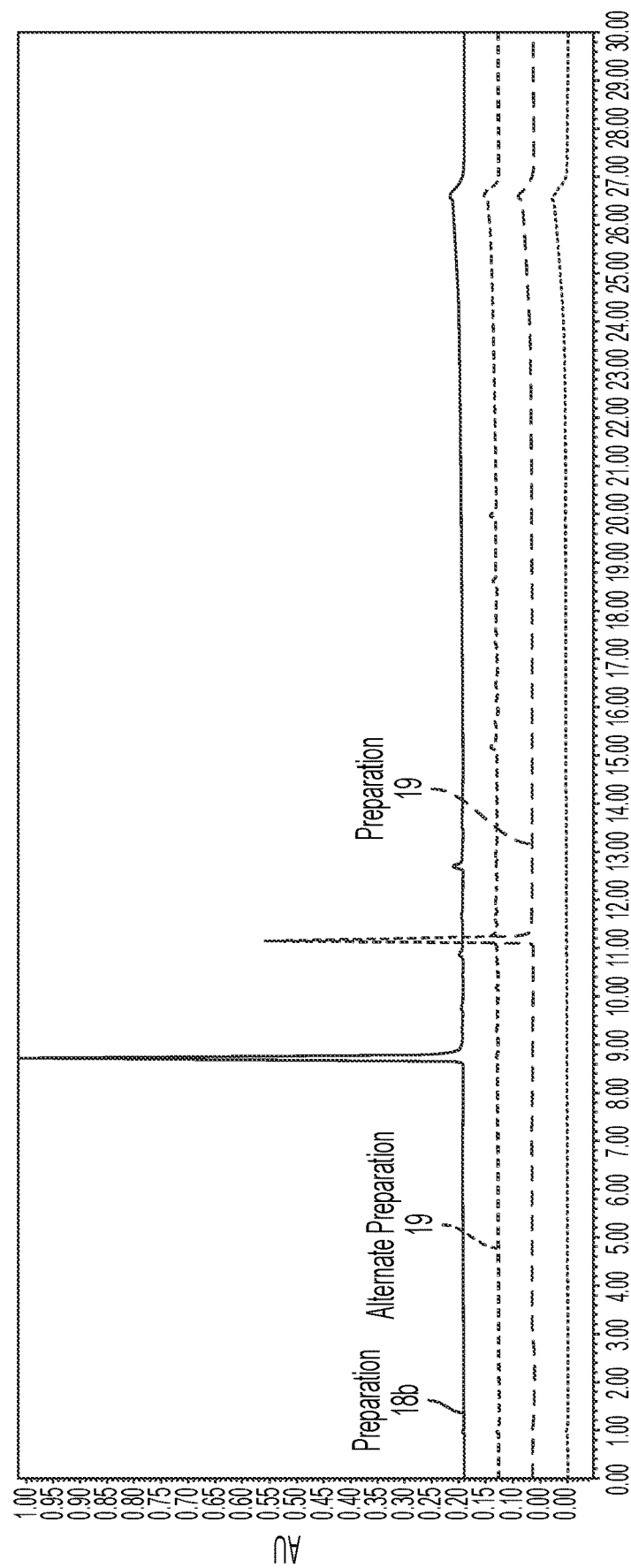
FIG. 1 is chromatography overlay of Preparation 18b, Preparation 19, and Alternate Preparation 19 utilizing chromatography system 1.

Several methods of preparing the compound of Formula A are described herein. While these methods change the order in which a group or portion of the molecule is added to the quinoline core or otherwise manipulated, each method utilizes the reaction between structures 8 and 9. As described below, the Compounds of Formula A contain a chiral center, and the methods described herein may be useful in the preparation of enantio-enriched material.

Compounds of Formula A contain a chiral center and the methods described herein can be used to prepare racemic Formula A or enantio-enriched Formula A that comprises predominantly the R enantiomer or the S enantiomer. The R and S enantiomers encompassed by Formula A are shown immediately below. The R-enantiomeric form is exemplified in Formula B:

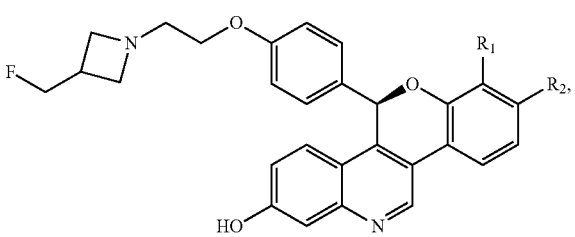

and the S-enantiomeric form is exemplified in Formula C:

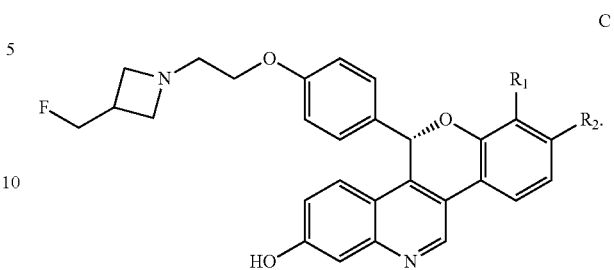

The enantio-enriched compounds of Formula A, i.e., the compounds of Formula B (where there is more enantiomer of Formula B than of Formula C) and Formula C (where there is more enantiomer of Formula C than of Formula B), may be prepared be chiral synthesis (as described herein) or racemic Formula A can be resolved to afford enantio-enriched material using methods known in the art, such as chiral chromatography or by converting the racemic Formula A into diastereomeric salts, separating the diastereomeric salts, converting the diastereomeric salts into a non-salt form and isolating the enantio-enriched compound. While Formula A can be resolved as described above, any racemic intermediate disclosed herein can be resolved using the methods known in the art, and the resulting enantio-enriched compound can be used to prepare enantio-enriched compounds of Formula B or Formula C.

The compounds of Formulas A, B, and C that can be made using the methods disclosed herein are disclosed in Table 1 (in these compounds, $R_7$ is H):

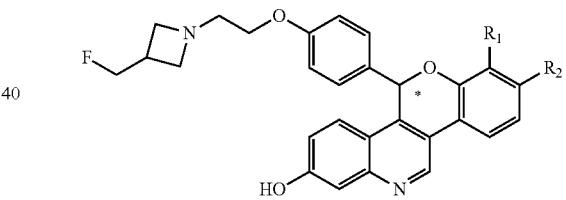

| Compound | $R_1$ | $R_2$ | Stereo at (*) |
|---|---|---|---|
| A-1 | H | $CF_3$ | Racemic |
| A-2 | $CF_3$ | H | Racemic |
| A-3 | H | Cl | Racemic |
| A-4 | Cl | H | Racemic |
| A-5 | H | F | Racemic |
| A-6 | F | H | Racemic |
| A-7 | H | $CH_3$ | Racemic |
| A-8 | $CH_3$ | H | Racemic |
| B-1 | H | $CF_3$ | R |
| B-2 | $CF_3$ | H | R |
| B-3 | H | Cl | R |
| B-4 | Cl | H | R |
| B-5 | H | F | R |
| B-6 | F | H | R |
| B-7 | H | $CH_3$ | R |
| B-8 | $CH_3$ | H | R |
| C-1 | H | $CF_3$ | S |
| C-2 | $CF_3$ | H | S |
| C-3 | H | Cl | S |
| C-4 | Cl | H | S |
| C-5 | H | F | S |
| C-6 | F | H | S |
| C-7 | H | $CH_3$ | S |
| C-8 | $CH_3$ | H | S |

In an embodiment, the compounds of Formula A have the R-enantiomeric form, i.e., they are Formula B.

In a particularly preferred embodiment, the compound of Formula B is

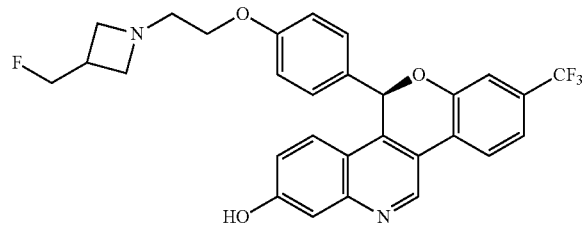 [SMILES: Oc1ccc2c3c(cnc2c1)-c1ccc(C(F)(F)F)cc1O[C@@H]3c1ccc(OCCN2CC(CF)C2)cc1]

or a pharmaceutically acceptable salt thereof.

In one embodiment, this compound is the free amine. In another embodiment, this compound is the tosylate salt. In a further embodiment, this compound is prepared according to any of the processes disclosed herein.

Also described herein are pharmaceutical compositions comprising the compounds of Formulas A, B, and C, as described herein, or pharmaceutically acceptable salts thereof, in combination with a pharmaceutically acceptable excipient, carrier, or diluent. The pharmaceutical compositions described herein may be prepared using pharmaceutically acceptable additives. The term "pharmaceutically acceptable additive(s)" as used herein, refers to one or more carriers, diluents, and excipients that are compatible with the other additives of the compositions or formulations and not deleterious to the patient. The compounds of Formula A, B, and C or pharmaceutically acceptable salts thereof, described herein can be formulated as pharmaceutical compositions administered by a variety of routes, such as oral or IV. Bioavailability is often a factor in cancer treatment and the ability to choose administration methods and pharmaceutical compositions to control or optimize the bioavailability of an active ingredient is useful. For example, an orally bioavailable SERD composition would be particularly useful. The compounds of Formula A, B, and C, or pharmaceutically acceptable salts thereof, as described herein are believed to have oral bioavailability. Examples of pharmaceutical compositions and processes for their preparation can be found in "Remington: The Science and Practice of Pharmacy", L. V. Allen Jr, Editor, 22nd Ed., Mack Publishing Co., 2012. Non-limiting examples of pharmaceutically acceptable carriers, diluents, and excipients include the following: saline, water, starch, sugars, mannitol, and silica derivatives; binding agents such as carboxymethyl cellulose and other cellulose derivatives, alginates, gelatin, and polyvinyl-pyrrolidone; kaolin and bentonite; and polyethyl glycols.

According to the various aspects and embodiments described herein, disclosed herein are new methods of preparing compounds of Formula A, B, and C. Compounds of Formula A, B, and C can be prepared using the reagents and reaction schemes illustrated in the Schemes, Preparations and Examples below. The specific synthetic steps for each of the routes described may be combined in different ways, or in conjunction with steps from different procedures, to prepare compounds of Formula A, B, and C as described herein, or salts thereof, including pharmaceutically acceptable salts.

The products can be recovered by conventional methods well known in the art, including extraction, evaporation, precipitation, chromatography, filtration, trituration, and crystallization. The reagents and starting materials are readily available to one of ordinary skill in the art, such as from commercial sources or may be produced using methods known by those of skill.

In some aspects, the disclosure provides methods for the synthesis of novel intermediates and processes useful for the synthesis of the compounds of Formula A, B, and C as described herein. In such aspects, the disclosure provides compositions of matter comprising novel intermediate compounds, and salts thereof. Additionally, certain intermediates described herein may contain one or more protecting groups. The protecting group may be variable and can be the same or different in each occurrence depending on the particular reaction conditions and the particular transformations to be performed. Typical protection and deprotection conditions are known to the skilled artisan and are described in the literature (See for example "Greene's Protective Groups in Organic Synthesis", Fourth Edition, by Peter G. M. Wuts and Theodora W. Greene, John Wiley and Sons, Inc. 2007).

Individual isomers, enantiomers, and diastereomers may be separated or resolved by one of ordinary skill in the art at any convenient point in the synthesis of compounds of Formula A, B, and C as described herein, by methods such as selective crystallization techniques or chiral chromatography (See for example, J. Jacques, et al., "Enantiomers, Racemates, and Resolutions", John Wiley and Sons, Inc., 1981, and E. L. Eliel and S. H. Wilen, "Stereochemistry of Organic Compounds", Wiley-Interscience, 1994).

One of skill in the art will also appreciate that the compounds of Formula A, B, and C and pharmaceutically acceptable salts thereof, can be deuterated or tritiated (where at least one hydrogen is replaced by a deuterium or tritium), and such molecules are within the scope of the compounds disclosed herein. The deuterated and tritiated compounds are enriched in deuterium and/or tritium to levels beyond those that could be found in nature.

In the deuterated compounds, including intermediates, disclosed herein, at least one position is isotopically enriched (an isotopically-enriched compound stands in contrast to a "non-isotopically enriched" compound, in which the percentages of the various isotopes are substantially the same as the naturally occurring percentages) at least 20%, relative to a non-isotopically enriched compound. In an embodiment, at least two positions are isotopically enriched at least 20% relative to a non-isotopically enriched compound. In an embodiment, at least three positions are isotopically enriched at least 20% relative to a non-isotopically enriched compound. In another embodiment, at least four positions are isotopically enriched at least 20% relative to a non-isotopically enriched compound.

In the deuterated compounds, including intermediates, disclosed herein, at least one position is isotopically enriched (an isotopically-enriched compound stands in contrast to a "non-isotopically enriched" compound, in which the percentages of the various isotopes are substantially the same as the naturally occurring percentages) at least 30%, relative to a non-isotopically enriched compound. In an embodiment, at least two positions are isotopically enriched at least 30% relative to a non-isotopically enriched compound. In an embodiment, at least three positions are isotopically enriched at least 30% relative to a non-isotopically enriched compound. In another embodiment, at least four positions are isotopically enriched at least 30% relative to a non-isotopically enriched compound.

In the deuterated compounds, including intermediates, disclosed herein, at least one position is isotopically enriched (an isotopically-enriched compound stands in contrast to a "non-isotopically enriched" compound, in which the percentages of the various isotopes are substantially the same as the naturally occurring percentages) at least 40%, relative to a non-isotopically enriched compound. In an embodiment, at least two positions are isotopically enriched at least 40% relative to a non-isotopically enriched compound. In an embodiment, at least three positions are isotopically enriched at least 40% relative to a non-isotopically enriched compound. In another embodiment, at least four positions are isotopically enriched at least 40% relative to a non-isotopically enriched compound.

In the deuterated compounds, including intermediates, disclosed herein, at least one position is isotopically enriched (an isotopically-enriched compound stands in contrast to a "non-isotopically enriched" compound, in which the percentages of the various isotopes are substantially the same as the naturally occurring percentages) at least 50%, relative to a non-isotopically enriched compound. In an embodiment, at least two positions are isotopically enriched at least 50% relative to a non-isotopically enriched compound. In an embodiment, at least three positions are isotopically enriched at least 50% relative to a non-isotopically enriched compound. In another embodiment, at least four positions are isotopically enriched at least 50% relative to a non-isotopically enriched compound.

In the deuterated compounds, including intermediates, disclosed herein, at least one position is isotopically enriched (an isotopically-enriched compound stands in contrast to a "non-isotopically enriched" compound, in which the percentages of the various isotopes are substantially the same as the naturally occurring percentages) at least 60%, relative to a non-isotopically enriched compound. In an embodiment, at least two positions are isotopically enriched at least 60% relative to a non-isotopically enriched compound. In an embodiment, at least three positions are isotopically enriched at least 60% relative to a non-isotopically enriched compound. In another embodiment, at least four positions are isotopically enriched at least 60% relative to a non-isotopically enriched compound.

In the deuterated compounds, including intermediates, disclosed herein, at least one position is isotopically enriched (an isotopically-enriched compound stands in contrast to a "non-isotopically enriched" compound, in which the percentages of the various isotopes are substantially the same as the naturally occurring percentages) at least 70%, relative to a non-isotopically enriched compound. In an embodiment, at least two positions are isotopically enriched at least 70% relative to a non-isotopically enriched compound. In an embodiment, at least three positions are isotopically enriched at least 70% relative to a non-isotopically enriched compound. In another embodiment, at least four positions are isotopically enriched at least 70% relative to a non-isotopically enriched compound.

In the deuterated compounds, including intermediates, disclosed herein, at least one position is isotopically enriched (an isotopically-enriched compound stands in contrast to a "non-isotopically enriched" compound, in which the percentages of the various isotopes are substantially the same as the naturally occurring percentages) at least 80%, relative to a non-isotopically enriched compound. In an embodiment, at least two positions are isotopically enriched at least 80% relative to a non-isotopically enriched compound. In an embodiment, at least three positions are isotopically enriched at least 80% relative to a non-isotopically enriched compound. In another embodiment, at least four positions are isotopically enriched at least 80% relative to a non-isotopically enriched compound.

In the deuterated compounds, including intermediates, disclosed herein, at least one position is isotopically enriched (an isotopically-enriched compound stands in contrast to a "non-isotopically enriched" compound, in which the percentages of the various isotopes are substantially the same as the naturally occurring percentages) at least 90%, relative to a non-isotopically enriched compound. In an embodiment, at least two positions are isotopically enriched at least 90% relative to a non-isotopically enriched compound. In an embodiment, at least three positions are isotopically enriched at least 90% relative to a non-isotopically enriched compound. In another embodiment, at least four positions are isotopically enriched at least 90% relative to a non-isotopically enriched compound.

In one aspect, disclosed herein is a process for preparing a compound, or salts thereof, of Formula A:

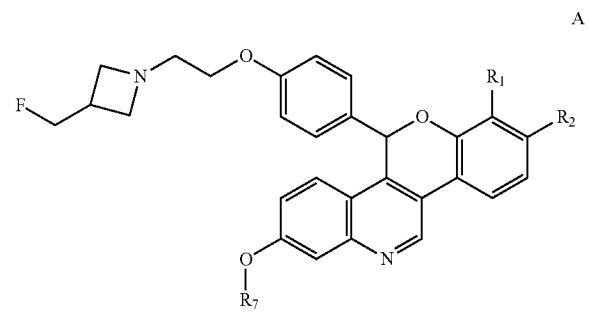

wherein either $R_1$ or $R_2$ is independently Cl, F, —$CF_3$, or —$CH_3$, and the other is H; and $R_7$ is H or PG, wherein the process comprises reacting a compound of the structure:

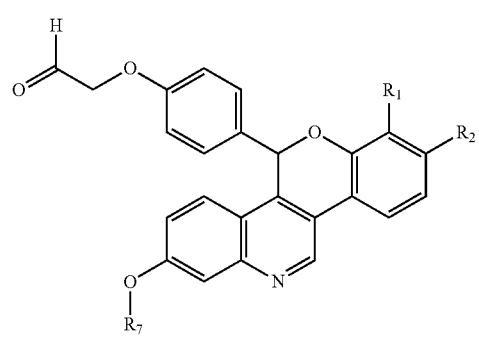

or a salt thereof, in a solvent with an amine of structure 9

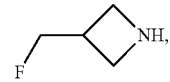

or a salt thereof, and a reducing agent.

In embodiments, the process may comprise preparing a compound of structure 8, or a salt thereof, the process comprising reacting a compound of the structure

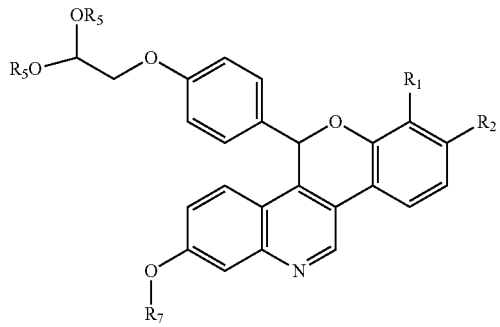

7 wherein each $R_5$ is independently $C_1$-$C_6$ alkyl or the two $R_5$ groups combined are —$CH_2CH_2$— or —$CH_2CH_2CH_2$—, and $R_7$ is PG or H; wherein PG is an alcohol protecting group, under hydrolytic conditions at a pH of about 6 or less. In some embodiments, the hydrolytic conditions comprise reaction with an acid. In one embodiment, $R_7$ is H. In an alternate embodiment, $R_7$ is a protecting group (PG).

In some embodiments, the process may comprise preparing a compound of the structure 7, or a salt thereof, the process comprising reacting a compound of the structure

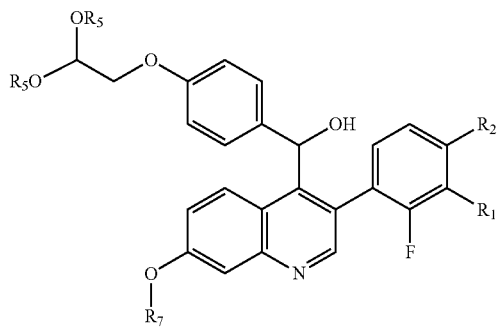

6 under basic conditions effective to deprotonate the hydroxyl group to cyclize the compound. In some embodiments, the basic conditions can comprise a base selected from $Cs_2CO_3$, NaH, sodium tert-butoxide, NaOH, LiGH, KOH, and alkoxides such as methoxide, ethoxide, sodium tert-pentoxide, or potassium tert-pentoxide, where the counterion is derived from a group I or group II element, or a non-nucleophilic base such as DBU. In one embodiment, the base comprises at least one of $Cs_2CO_3$, sodium tert-pentoxide, or NaOH.

In some embodiments, the process comprises preparing a compound of the structure 6, or a salt thereof, the process comprising reacting a compound of the structure

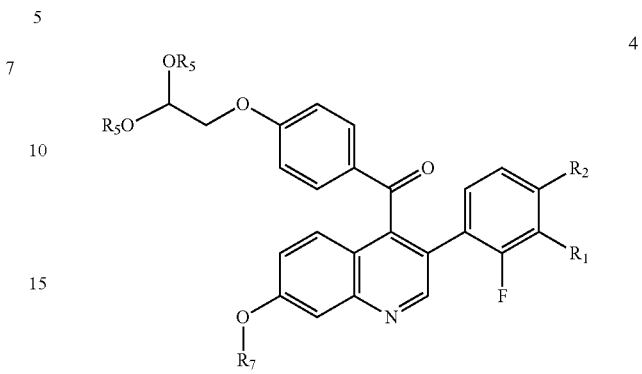

4 under conditions effective to reduce the ketone to produce alcohol 6. During the reduction of ketone 4, some dihydroquinoline 5 may also form. Dihydroquinoline may be oxidized back to the quinoline 6 using at least one oxidizing agent.

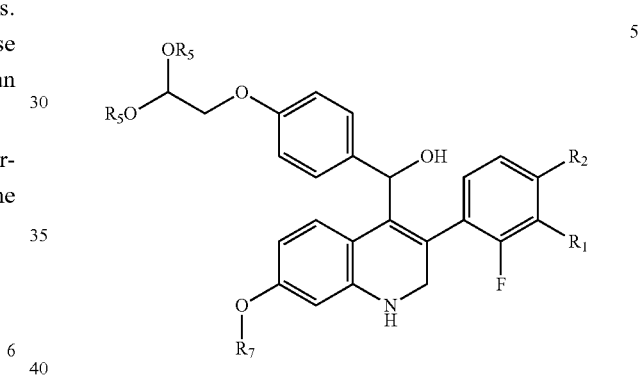

5

Examples of oxidizing agents include, but are not limited to $MnO_2$, DDQ, and oxygen. In some embodiments, the oxidizing agent is $MnO_2$. One skilled in the art would also realize that the ketone could be reduced under standard reducing conditions such as $NaBH_4$, $LiBH_4$, $LiAlH_4$, $NaBH_3CN$, STAB, or hydrogenation such as hydrogen/palladium or hydridic reagents to give the racemic alcohol, which could be subjected to chiral resolution.

In some embodiments, the process may comprise preparing a compound of the structure 4, or salt thereof, the process comprising reacting a compound of the structure

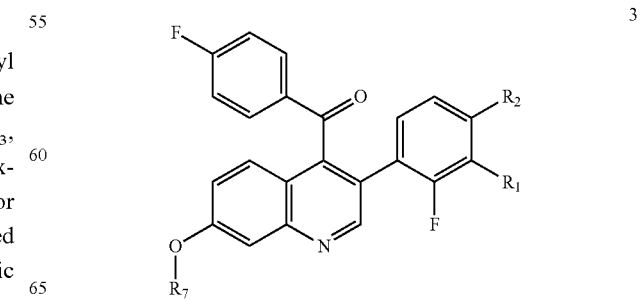

3 under conditions effective to perform an intermolecular nucleophilic aromatic substitution ($S_NAr$) of the fluoro group with a compound such as 2,2-diethoxyethanol, 2,2-dimethoxyethanol, 2-hydroxymethyl-1,3-dioxane, or 2-hydroxymethyl-1,3-dioxolane, a protected aldehyde-2-carbon fragment-alcohol to form 4. Acetals, such as dimethyl acetal, diethyl acetal or —$CH_2CH_2$— or —$CH_2CH_2CH_2$— are non-limiting examples of aldehyde protecting groups that can be used in the processes disclosed herein.

In some embodiments, the process comprises preparing a compound of the structure 3, or salt thereof, the process comprising a cross-coupling reaction between a compound of the structure

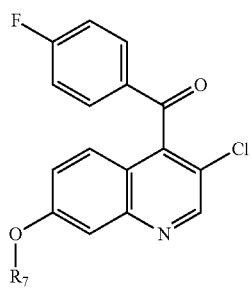

1 with a compound of the structure

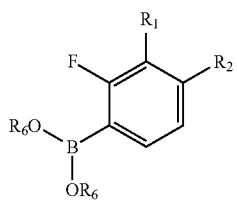

2 where $R_6$ can be hydrogen or alkyl or a structure where the two $R_6$ groups are joined by at least two carbons, to form dioxaborolanes or dioxaborinanes, under conditions comprising a palladium or a nickel catalyst effective to form the compound of structure 3.

Alternatively, in some embodiments, the process may prepare a compound of structure 3, or salt thereof, by reacting a compound of structure 17

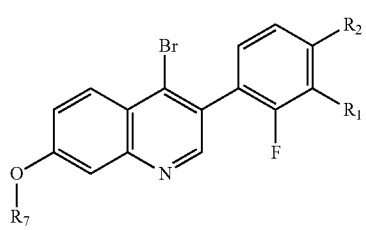

17 with a compound of the structure 13 (acid chloride or Weinreb amide) or 13a (aldehyde)

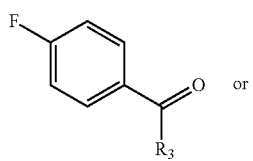

13

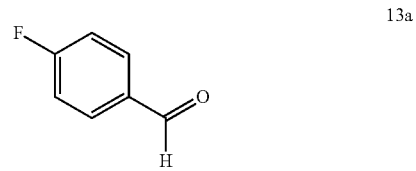

13a where $R_3$=Cl or HN(OMe)$R_4$ and $R_4$=$C_1$-$C_4$ alkyl, under standard Grignard or lithiation addition reaction conditions. In cases where 13a is used, the resulting product is an alcohol, which is then oxidized to the ketone, using methods disclosed herein or methods known in the art.

Compounds of Formula A, B, and C as described herein, pharmaceutically acceptable salts thereof, and pharmaceutical compositions thereof, may be used to treat breast cancer, ovarian cancer, endometrial cancer, prostate cancer, uterine cancer, gastric cancer, or lung cancer. Methods of treatment include administering a therapeutically effective amount of a compound as described herein, or a pharmaceutically acceptable salt thereof, to a patient in need. The compounds described herein, and pharmaceutically acceptable salts thereof, can be used in the treatment of breast cancer, ovarian cancer, endometrial cancer, prostate cancer, uterine cancer, gastric cancer, and lung cancer as well as mutations due to emerging resistance. Endometrial cancers include endometrioid endometrial cancer.

The compounds Formula A, B, and C and pharmaceutically acceptable salts thereof, find use in the manufacture of a medicament for treating breast cancer, ovarian cancer, endometrial cancer, prostate cancer, uterine cancer, gastric cancer, or lung cancer, among other diseases and disorders related to cell proliferation, particularly unregulated cell proliferation driven by ER transcription.

These and other aspects and embodiments are provided in more detail in the description that follows.

Novel methods of making tetracyclic compounds and pharmaceutical salts thereof that act as SERDs are disclosed herein. The SERDs that are prepared by the methods and processes described herein provide inhibition of ER-mediated transcription that will be useful in treating cancers such as breast cancer, ovarian cancer, endometrial cancer, prostate cancer, uterine cancer, gastric cancer, and lung cancer as well as mutations due to emerging resistance. Endometrial cancers include endometrioid endometrial cancer. These SERDs can be used either as single agents or in combination with other classes of drugs including selective estrogen receptor modulators (SERMs), aromatase inhibitors, CDK4 inhibitors, CDK6 inhibitors, PI3K inhibitors, and mTOR inhibitors to treat hormone receptor-positive cancers such as breast cancer, gastric cancer, and/or lung cancer In an aspect, the disclosure provides a process for preparing a compound, or a salt thereof, of Formula A:

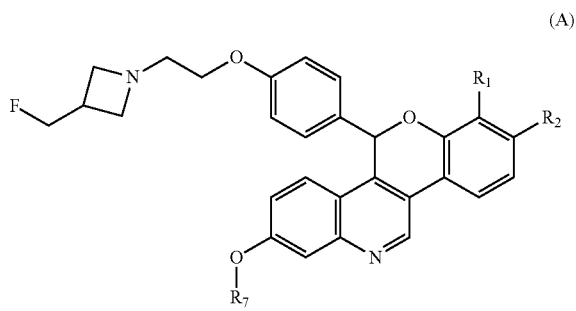

(A)

wherein either R₁ or R₂ is independently Cl, F, —CF₃, or —CH₃, and the other is H; and R₇ is H or PG,
wherein the process comprises reacting a compound of the structure:

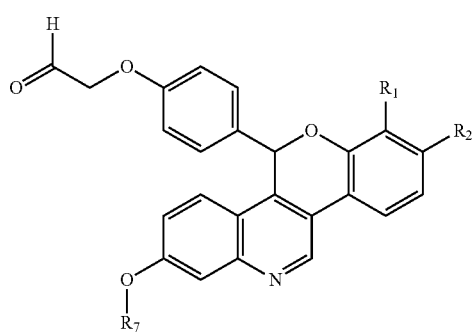

8 or a salt thereof, in a solvent with an amine of structure 9

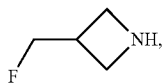

9 or a salt thereof, and a reducing agent. Examples of suitable solvents include polar solvents. Polar solvents include alcohols, ethers, nitriles, and some halogenated hydrocarbons. Examples of suitable alcohol solvents include MeOH, EtOH, isopropyl alcohol tert-butanol, tert-amyl alcohol, while suitable ethers include THF, cyclopentyl methyl ether, methyl tert-butyl ether, and 2-MeTHF. ACN is an example of a suitable nitrile solvent. Suitable halogenated solvents include DCM, chloroform and 1,2-dichloroethane. Other solvents that may be used include DMF NMP, NBP, DMSO, and DMAC. Combinations of two or more solvents may be used.

Examples of reducing agents include, but are not limited to STAB, LiBH₄, NaBH₄, NaBH₃CN or pyridine borane. In some reduction protocols, a base, such as TEA or DIPEA is also present. In one embodiment, the reducing agent comprises STAB. In another embodiment, the reducing agent comprises NaBH₃CN. In still another embodiment, the reducing agent comprises pyridine borane.

In embodiments, the process may comprise preparing a compound of structure 8, or a salt thereof, the process comprising reacting a compound of the structure

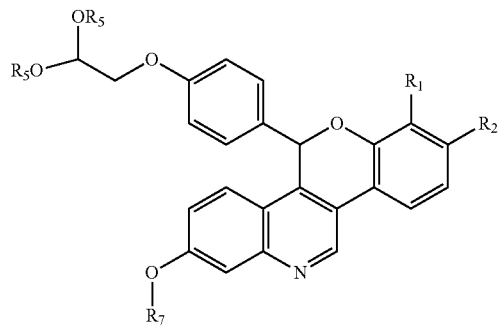

7 under hydrolytic conditions. In some embodiments, the hydrolytic conditions comprise using an acid.

In some embodiments, the process may comprise preparing a compound of the structure 7, or a salt thereof, the process comprising reacting a compound of the structure

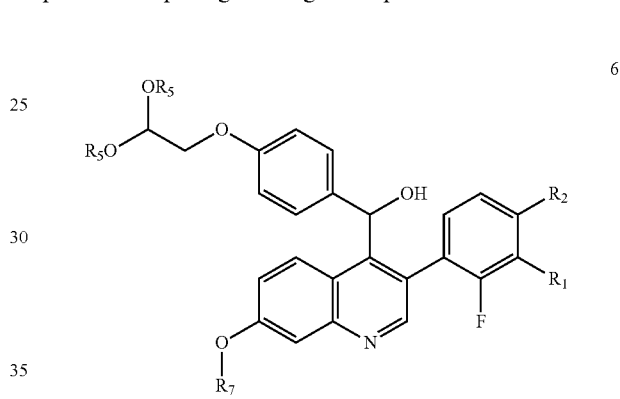

6 under basic conditions. The base deprotonates the hydroxyl group, which then reacts, to form the cyclized compound. In some embodiments, the basic conditions comprise a base selected from Cs₂CO₃, NaH, sodium tert-butoxide, LiGH, NaOH, KOH, and alkoxides such as methoxide, ethoxide, sodium tert-pentoxide, or potassium tert-pentoxide, where the counterion is derived from a group I or group II element, or an organic base such as DBU. In one embodiment, the base comprises at least one of Cs₂CO₃, sodium tert-pentoxide, or NaOH.

In some embodiments, the process may comprise preparing a compound of the structure 6, or a salt thereof, the process comprising reacting a compound of the structure

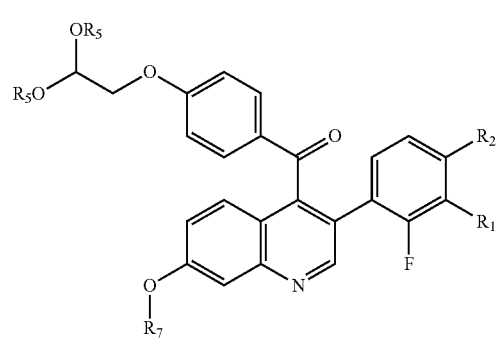

4 under conditions effective to reduce the ketone to an alcohol. Such conditions comprise the use of a ketone reducing agent. Examples of ketone reducing agents include, but are not limited to LiAlH₄, NaBH₄, or borane-ligand, where the ligand is THF, Me₂S, catechol, or N,N-diethylaniline.

In some embodiments, the ketone is enantioselectively reduced, to produce the corresponding chiral non-racemic alcohol of structure 6B or 6C. Examples of chiral reduction protocols and/or agents include, but are not limited to using LiAlH₄ coordinated to a chiral ligand, such as BINOL, chiral borohydride reducing agents, chiral alkylborohydride reducing agents, a Corey-Bakshi-Shibata (CBS) reduction comprising a borolidine reagent, chiral ligands coordinated to a metallic catalyst (such as hydrogen gas and ruthenium coordinated to BINAP), enzymatic reductions, and rhodium coordinated to PyBOX. In one embodiment, the enantioselective reducing conditions comprise a CBS reduction comprising a borolidine reagent.

In some embodiments, the process may comprise preparing a compound of the structure 4, or salt thereof, the process comprising reacting a compound of the structure

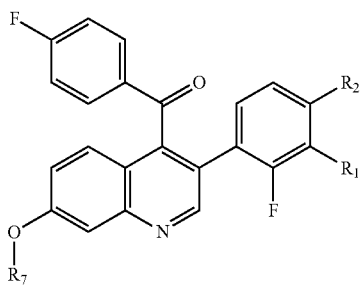

under conditions effective to perform a $S_NAr$ of the fluoro group with a compound such as 2,2-diethoxyethanol or 2-hydroxymethyl-1,3-dioxolane, a protected aldehyde-2-carbon fragment-alcohol to form 4. Alkyl and cyclic acetals, such as dimethyl, diethyl acetals or —CH₂CH₂— or —CH₂CH₂CH₂, are non-limiting examples of aldehyde protecting groups.

In some embodiments, the process may comprise preparing a compound of the structure 3, or salt thereof, the process comprising a cross-coupling reaction between a compound of the structure

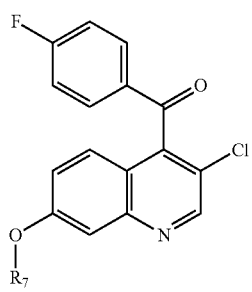

with a compound of the structure

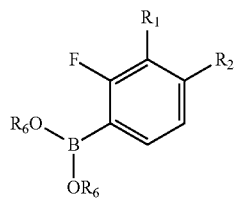

where $R_6$ can be hydrogen or alkyl or a structure where the two $R_6$ groups are joined by at least two carbons, to form dioxaborolanes or dioxaborinanes. In an embodiment, the cross-coupling reaction uses a catalyst. In an embodiment, the catalyst comprises a transition metal catalyst. Transition metal catalysts that may be used comprise palladium catalyst or nickel catalyst. In some embodiments, when a palladium catalyst is used, the palladium catalyst may comprise XantPhos Pd G2, cataCXium® A Pd G3, bis(triphenylphosphine)palladium(II) chloride, tris(dibenzylideneacetone)dipalladium (0) with tricyclohexylphosphine, (1,1'-bis(diphenylphosphino)ferrocene)palladium(II) chloride, palladium tetrakistriphenylphosphine, or palladium(II) acetate. Suitable nickel catalysts could be NiCl₂(dppp), NiCl₂(dppf), G3DenP-Ni.

Definitions

As used herein, "ACN" refers to acetonitrile; "(Amphos)₂PdCl₂" refers to bis(di-tert-butyl(4-dimethylaminophenyl)phosphine)dichloropalladium(II); "BSA" refers to Bovine Serum Albumin; "BINAP" refers to 2,2'-bis(diphenylphosphino)-1,1'-binaphthyl; "BINOL" refers to 1,1'bi-2-naphthol; "Bu" refers to butyl; "besylate" refers to $C_6H_5SO_3$-or benzenesulfonate; "cataCXium® A Pd G3" refers to [(di(1-adamantyl)-butylphosphine)-2-(2'-amino-1,1'-biphenyl)]palladium(II) methanesulfonate; "DBU" refers to 1,8-diazabicylo(5.4.0)undec-7-ene; "DCM" refers to dichloromethane or methylene chloride; "DDQ" refers to 2,3-dichloro-5,6-dicyano-1,4-benzoquinone; "DEA" refers to diethylamine; "DIPEA" refers to N,N-diisopropylethylamine; "DMAC" refers to dimethylacetamide; "DMF" refers to N,N-dimethylformamide; "DMSO" refers to dimethylsulfoxide; "ee" refers to enantiomeric excess and may be measured using chiral gas chromatography or chiral liquid chromatography. "Erα" refers to estrogen receptor α; "EtOAc" refers to ethyl acetate; "EtOH" refers to ethanol or ethyl alcohol; "Ex" refers to example; "FLU" refers to fluorescence unit; "G3DenP-Ni" refers to dendrimer stabilized nickel nanoparticles; "h" refers to hours; "hERα" refers to human estrogen receptor α; "IC₅₀" refers to concentration of compound that reduces a given response (ligand binding, enzyme response) by 50%; "IPA" refers to isopropyl alcohol or isopropanol; "Me" refers to methyl; "MeOH" refers to methanol or methyl alcohol; "2-MeTHF" refers to 2-methyltetrahydrofuran; "mesylate" refers to $CH_3SO_3$— or methylsulfonate; "min" refers to minutes; "MTBE" refers to methyl tert-butyl ether; "NiCl$_2$(dppf)" refers to 1,1'-bis(diphenylphosphino)ferrocenedichloronickel(II); "NCS" refers to N-chlorosuccinimide; "NiCl$_2$(dppp)" refers to dichloro[1,3-bis(diphenylphosphino)propane]nickel; "NBP" refers to N-butylpyrrolidinone; "NMP" refers to N-methyl-2-pyrrolidone; "PBS" refers to Phosphate Buffered Saline; "PEPPSI™-IPr" refers to Pyridine-Enhanced Precatalyst Preparation Stabilization and Initiation-[1,3-Bis(2,6-diisopropylphenyl)imidazol-2-ylidene](3-chloropyridyl)palladium(II) dichloride; "Prep" refers to preparation; "PyBOX" refers to pyridine linker of bis(oxazoline) ligands; "RNase" refers to a group of hydrolytic enzymes that degrade ribonucleic acid (RNA) molecules; "RT" refers to room temperature; "STAB" refers to sodium triacetoxyborohydride; "TEMPO" refers to (2,2,6,6-tetramethylpiperidin-1-yl)oxyl or (2,2,6,6-tetramethylpiperidin-1-yl)oxidanyl; "THF" refers to tetrahydrofuran; "tosylate" refers to $H_3CC_6H_4SO_2$— or -OTs; "p-TsOH" refers to 4-methylbenzenesulfonic acid or toluenesulfonic acid; "XantPhos Pd G2" refers to chloro[(4,5-bis(diphenylphosphino)-9,9-dimethylxanthene)-2-(2'-amino-1,1'-biphenyl)]palladium(II); "XPhos Pd G2" refers to chloro(2-dicyclohexylphosphino-2',4',6'-triisopropyl-1,1'-biphenyl)[2-(2'-amino-1,1'-biphenyl)]palladium(II) and "XRPD" refers to x-ray powder diffraction.

All compound names were generated using Biovia Draw 2017 R$_2$, ChemDraw version 19.1 or were derived therefrom.

The following schemes, preparations, and examples further illustrate the invention.

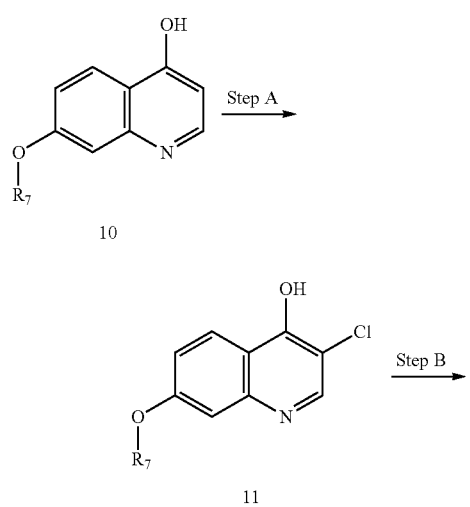

Scheme 1

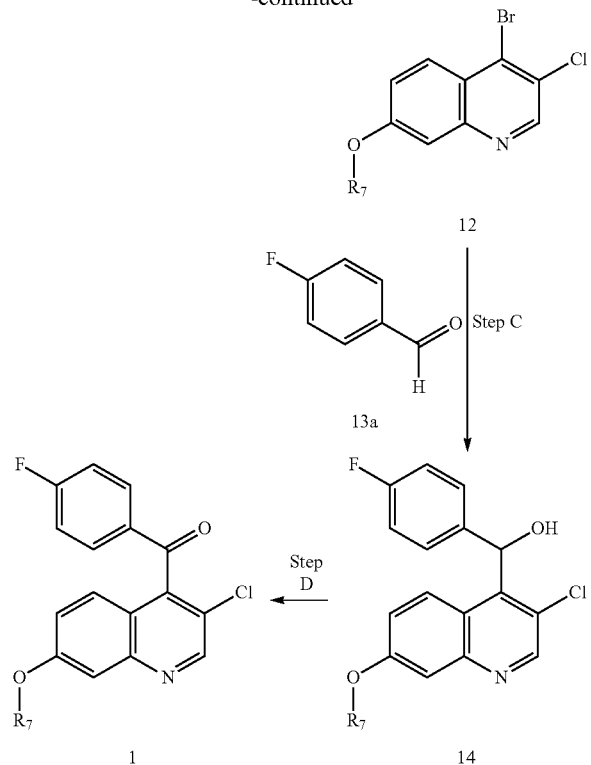

Scheme 1 describes the preparation of intermediates of structure 1. R$_7$ is PG or H, wherein PG is an alcohol protecting group. Examples of alcohol protecting groups include, but not limited to $C_1$-$C_4$ alkyl, benzyl, benzoyl, $C_1$-$C_6$ alkanoyl, methoxyethoxymethyl ether groups, silyl ether groups such as trimethyl silyl, triethyl silyl, tert-butyldimethylsilyl, tri-isopropylsilyloxymethyl, and tri-isopropylsilyl, tetrahydropyranyl, tetrahydrofuranyl, and ethoxyethyl ethers. In one embodiment, PG is methyl. In another embodiment, PG is benzoyl.

In Scheme 1, Step A, 7-methoxy-4-hydroxyquinoline, compound 10, is treated with a halogenating agent, such as NCS, with heating in DMF to about 40° C. to provide compound 11. In Step B, compound 11 can be reacted in with P(O)Br$_3$ in a solvent such as toluene with heating to about 100° C., to brominate the quinoline ring at the 4 position, displacing the hydroxy group to provide compound 12 of Step B. Alternatively, this transformation can also be performed under milder conditions using phosphorous tribromide in a solvent such as DMF at about 40° C. to give compound 12.

In Step C, a Grignard reaction is accomplished. The reaction involves an organometallic reaction in which an aryl magnesium halide, the Grignard reagent, adds to a carbonyl group such as an aldehyde, compound 13a, to give a benzylic alcohol, compound 14. Compound 14 is then oxidized to compound 1 using an oxidizing agent. Examples of oxidizing agents include KMnO$_4$, K$_2$Cr$_2$O$_7$, pyridinium chlorochromate, Dess-Martin conditions, Swern conditions, Oppenauer conditions, Fetizon conditions, and KBr/TEMPO, with sodium hypochlorite as the oxidant. In one embodiment KBr/TEMPO with sodium hypochlorite is used in a biphasic solvent system comprising EtOAc/water. Alternatively, after Step D, the aryl methyl ether of Step D may be demethylated (when PG is methyl) under a variety of conditions recognizable to the skilled artisan, such as treatment with BBr$_3$ or HBr. For example, compound 1 can be treated with BBr$_3$ slowly in a solvent such as DCM, which can be stirred and quenched under conditions to provide the deprotected product of compound 1 (where R$_7$ is H), or alternatively reacted with aqueous HBr under conditions (e.g., at reflux) to provide the deprotected product of compound 1 (where R$_7$ is H).

Scheme 2

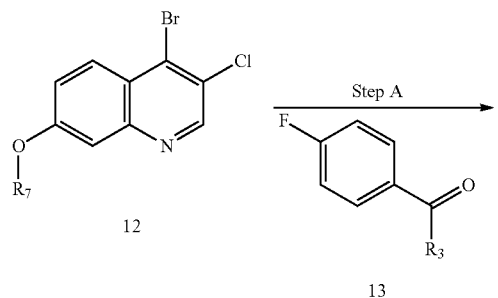

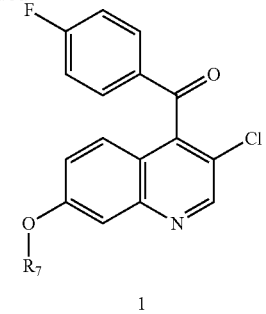

Scheme 2 illustrates an alternative method of coupling 12 and 13 to form compound 1, wherein PG is defined as above and R$_3$ can be Cl, N(OMe)R$_4$, where R$_4$=C$_1$-C$_4$ alkyl. In Step A, the ketone, compound 1, is generated by adding the Grignard reagent to the acid chloride (R$_3$=Cl) or Weinreb amide (R$_3$=N(OMe)R$_4$) with a solvent such as THF at temperatures below 0° C., preferably about −15 to −25° C. to give compound 1. In addition, organometallic nucleophiles can be used in place of the Grignard reagents, such as organolithium or organozinc variants of the Grignard reagent shown.

Alternatively, after Step A, the aryl methyl ether (when PG is methyl) of Step A may be demethylated as described in Scheme 1, after Step D.

Scheme 3

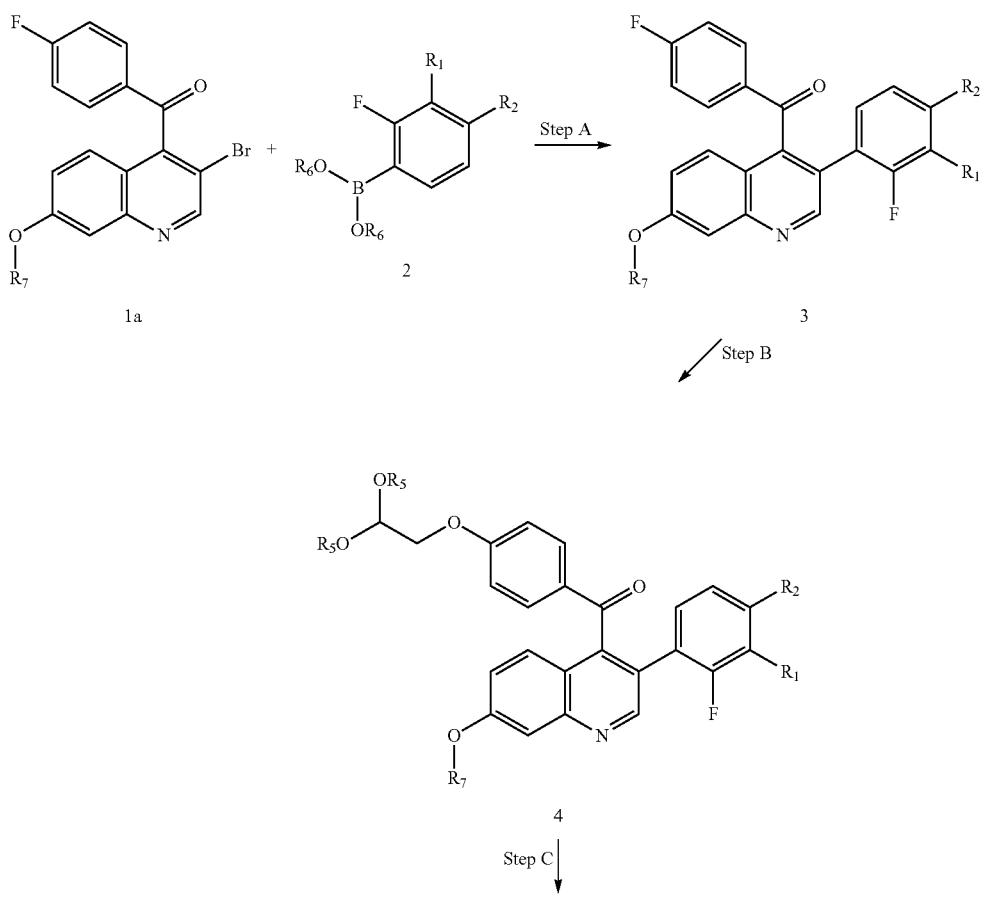

-continued
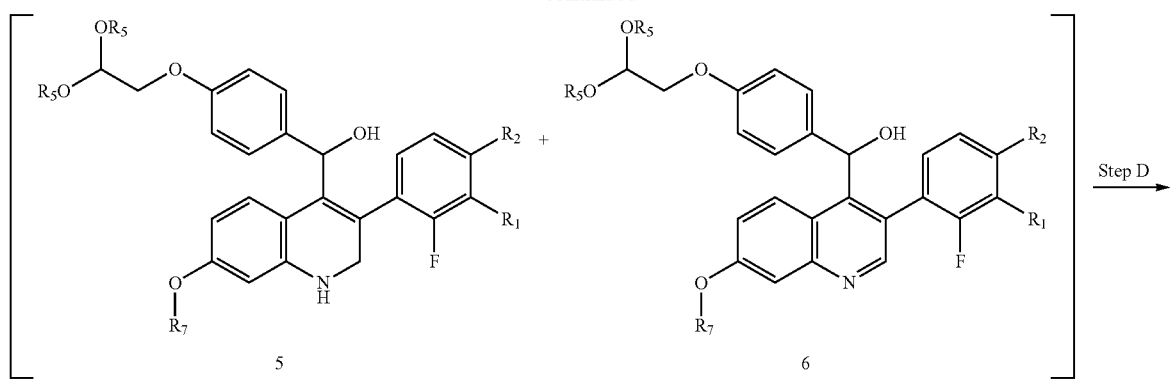
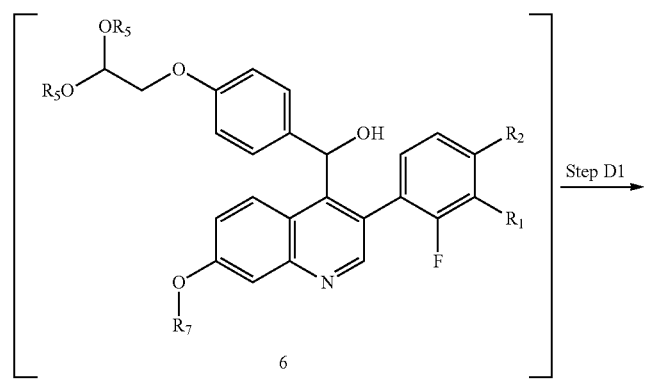
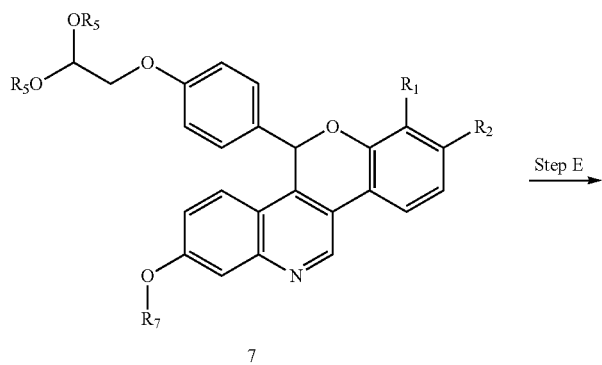
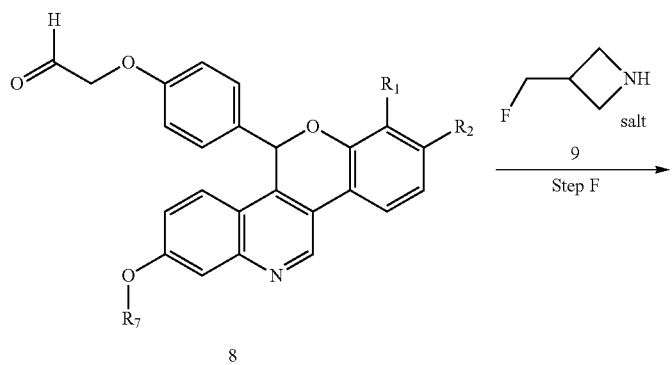

-continued

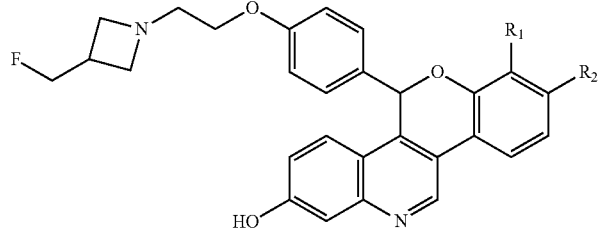

A

In Scheme 3, Step A, a Suzuki reaction may be carried out under basic conditions with compounds 1 and 2. The Suzuki reaction is well known in the art as a cross-coupling reaction, between a boronic acid, boronic ester or cyclic boronic ester and an organohalide or pseudohalide, such as a triflate (OTf), utilizing a palladium(0) catalyst or nickel catalyst. $R_6$ can be hydrogen or alkyl or a structure where the two $R_6$ groups are joined by at least two carbons, to form dioxaborolanes or dioxaborinanes. A variety of conditions that may be useful for facilitating such cross-coupling reactions. Alternative cross-coupling reactions include Negishi, Hiyama, Kumada, or Stille. Suitable palladium reagents may include XantPhos Pd G2, cataCXium® A Pd G3, bis(triphenylphosphine)palladium(II) chloride, tris(dibenzylideneacetone)dipalladium (0) with tricyclohexylphosphine, (1,1'-bis (diphenylphosphino)ferrocene)palladium(II) chloride, palladium tetrakistriphenylphosphine, or palladium(II) acetate. Suitable nickel catalysts could be $NiCl_2$(dppp), $NiCl_2$(dppf), G3DenP-Ni. The reaction can be an efficient high yielding reaction with low catalyst load (e.g., 1 mol % or lower). For example, a 4-halogen-substituted quinoline ketone, compound 1, where the halogen is typically Cl but could be Br or F, is coupled with an appropriately substituted boronic acid or ester (compound 2) such as a 2-fluoro 3 and/or 4-substituted phenylboronic acid utilizing a catalyst as above such as Pd-Xphos-G2 to form compound 3 and a base such as $NaHCO_3$, $K_2CO_3$, or $Cs_2CO_3$ in a solvent such as THF and water and heating to about 65° C. Other suitable solvents could be toluene, dioxane or DMF and temperature can range from about RT to about 100° C. In some embodiments, a Pd-XPhos-G2 Buchwald type catalyst may be used in the reaction. The reaction uses low palladium levels and thus palladium scavenging may be minimized or not needed; however, if necessary, Pd scavenging may be performed with silica thiol, which is the silica-bond equivalent of 1-propanethiol.

In Step B, compound 3 may undergo a $S_NAr$ reaction to form a protected aldehyde using 2,2-diethoxyethanol in a polar aprotic solvent and a base. Step B may be performed at temperatures below room temperature, such as about 5° C. Suitable bases include, but are not limited to sodium tert-butoxide, NaH, $Cs_2CO_3$, sodium tert-pentoxide, potassium tert-pentoxide, and/or DBU. In an embodiment, as the solvent comprises THF, and the base is potassium tert-butoxide. Various acetals, such as dimethyl, diethyl acetals, —$CH_2CH_2$— or —$CH_2CH_2CH_2$— can be used to protect the aldehyde group. Other possible polar aprotic solvents can be DMF, acetone, ACN, DCM, and EtOAc. The reaction may have high yields and may produce a crystalline product. For example, electron poor aromatic ring compound (compound 3) is reacted with an electron rich species, such as 2,2-diethoxyethanol to form compound 4.

One skilled in the art will recognize that the intermolecular $S_NAr$ reaction in Step B could be completed before the Suzuki reaction of Step A. Such a re-ordering may require less catalyst and boronic acid/ester which could result in a more economical process. See Scheme 4 below.

In Step C, the ketone moiety in compound 4 can be reduced to the alcohol in a chiral or achiral manner. Scheme 4, below, describes the chiral reduction of the ketone. The ketone could be reduced under standard reducing conditions. Suitable achiral reducing agents include, but are not limited to $NaBH_4$, $LiBH_4$, $LiAlH_4$, $NaBH_3CN$, or STAB. The resulting racemic alcohol can be subjected to chiral separation and isolation of the desired enantiomer.

The reduction of the ketone moiety in compound 4 affords a mixture of compounds 5 and 6. Without wishing to be bound to a theory, it is believed the over reduction of compound 6 to compound 5 is facilitated by the presence of residual Pd, from Step A. The Pd content of compound 3 and/or compound 4 can be reduced using silica thiol or a similar reagent. In some embodiments, the quenching of the reduction reaction may produce hydrogen gas, which may require an absorber. Preferably, the mixture of compounds 5 and 6 contains less than about 20% or less than about 15% or less than about 10% compound or less than about 9% or less than about 8% of compound 5, as determined by $^1H$ NMR.

The mixture of compounds 5 and 6 is usually not isolated. Instead, it is subjected to oxidation conditions, which converts compound 5 to compound 6. This oxidation can be accomplished using a variety of oxidizing agents. Examples of oxidizing agents include oxygen in an inert carrier (to prevent fires) and $MnO_2$. $MnO_2$ is inexpensive and abundant, but dense, and requires good agitation to keep in suspension. Various forms and particle sizes of $MnO_2$ may be utilized. A packed column (external to a reactor) may be used to avoid suspension and reactor fouling issues. In some embodiments, solvent exchanges may be avoided by utilizing ACN as the solvent. In another embodiment, about 5% oxygen in nitrogen can be used to oxidize compound 5 to compound 6.

After the oxidation reaction of step D, crude compound 6 is cyclized in Step D1, to form compound 7. Cyclization conditions include treating compound 6 with a suitable base, such as, for example, $Cs_2CO_3$, NaH, sodium tert-butoxide, LiGH, NaOH, KOH, an alkoxide base, such as sodium, potassium or lithium methoxide, sodium potassium or lithium ethoxide, sodium tert-pentoxide, or potassium tert-pentoxide, a non-nucleophilic base, such, for example, DBU, or mixtures of two or more thereof. In one embodiment, the base comprises at least one of $Cs_2CO_3$, sodium tert-pentoxide, or NaOH. In another embodiment, the base comprises $Cs_2CO_3$ or sodium tert-pentoxide. In a further embodiment, the base is $Cs_2CO_3$, and the cyclization reaction is performed at a temperature of about 80-90° C. or about 85° C. In another embodiment, the base is sodium tert-pentoxide. In an embodiment, the base is sodium tert-pentoxide, and the cyclization reaction is performed at a temperature of about 20-30° C. or about 25° C.

In some embodiments, undesirable solvents, such as dioxane, may be avoided by using solvents such as ACN, 2-MeTHF, and/or tert-amyl alcohol. While these three solvents are acceptable, the use of tert-amyl alcohol and/or 2-MeTHF are preferred. In one embodiment, the solvent comprises 2-MeTHF. In another embodiment, the solvent consists of 2-MeTHF. In a further, the solvent comprises tert-amyl alcohol or it consists of tert-amyl alcohol.

In Step E, compound 7 may undergo acetal hydrolysis to form aldehyde compound 8. This reaction may be carried out with an acid such as HCl, $H_2SO_4$, p-TsOH, methanesulfonic acid, trifluoromethanesulfonic acid, acetic acid, or trichloroacetic acid. In a preferred embodiment, the solvent for the hydrolysis comprises water and optionally, a second solvent, such as ACN. In another embodiment, p-TsOH is the preferred acid. In a preferred embodiment, at least one the following hydrolysis systems is used: $H_2SO_4$ in wet acetone, aqueous HCl in ACN, aqueous HCl in THF, TsOH in water and acetonitrile, or TsOH in aqueous THE can also with used. For example, compound 7 is can deprotected using aqueous HCl in ACN and the resulting aldehyde 8 forms a precipitate. Alternatively, compound 7 can be deprotected using TsOH in water and acetonitrile. In some embodiments, when the pH of the reaction mixture is controlled at about 6, the aldehyde is obtained, along with some of the hemiacetal. In some embodiments, the aldehyde is isolated as the hydrate, such as the monohydrate or dihydrate. Typically, the hydrate contains no more than about 8% water, more commonly, less than 6% water and still more preferably, less than 4% water, as determined using Karl Fischer titration. In a further embodiment, the aldehyde contains about 3% water, as determined by Karl Fischer titration. The presence of the monohydrate was confirmed via $^1$H NMR. The aldehyde monohydrate often contains some hemiacetal. For example, when $R_5$ is methyl or ethyl, then the methyl or ethyl acetal, respectively, is also formed. The exact pH of the deprotection reaction will affect the amount of hydrate (mono and/or di) and/or acetal present. In some embodiments, the bisulfite adduct of the aldehyde is prepared. The hydrated aldehyde and the hemiacetal form of the aldehyde convert to the aldehyde, when dissolved, such as, for example, for the reductive amination reaction of Step F.

In Step F, aldehyde 8, is subjected to reductive amination in a solvent, using a reducing agent. Examples of suitable solvents include polar solvents. Polar solvents include alcohols, ethers, nitriles, and some halogenated hydrocarbons. Examples of suitable alcohol solvents include MeOH, EtOH, and isopropyl alcohol. Suitable ethers include THF, cyclopentyl methyl ether, methyl tert-butyl ether, and 2-methyl THF (2-MeTHF). ACN is an example of a suitable nitrile solvent. Suitable halogenated solvents include DCM, chloroform and 1,2-dichloroethane. Other solvent that may be used include dimethyl formamide (DMF) NMP, NBP, DMSO, and DMAC. Combinations of two or more solvents may be used. In an embodiment, the alcohol solvent contains isopropanol, tert-butyl alcohol and/or tert-amyl alcohol. In another embodiment, the alcohol solvent contains isopropanol. In an embodiment, the alcohol solvent contains tert-butyl alcohol. In yet another embodiment, the alcohol solvent contains tert-amyl alcohol. In another embodiment, the solvent comprises THF or 2-MeTHF. In some embodiments, the solvent is THF. In another embodiment, the THF is anhydrous. In other embodiments, the solvent comprises 2-MeTHF. In another embodiment, the 2-MeTHF is anhydrous.

Reducing agents that can be used include, but are not limited to, $LiBH_4$, $NaBH_4$, $NaBH_3CN$, pyridine borane, STAB, or other boranes. In an embodiment, the reducing agent is STAB. In an alternate embodiment, the reducing agent is pyridine borane. In another embodiment, the reducing agent is $NaBH_3CN$. In some embodiments, the reducing agent is STAB, and the solvent comprises THF and/or 2-MeTHF. In some other embodiments, the reducing agent is pyridine borane, and the solvent comprises an alcohol.

In an embodiment, azetidine 9 is a free base. If a salt of azetidine 9 is used, suitable salts include, but are not limited to the HCl salt, tosylate salt, mesylate salt, or besylate salt. In one embodiment, the azetidine salt is the HCl salt. In another embodiment, the azetidine salt is the tosylate salt. When a salt of azetidine 9 is used, an external base can be added to the reductive amination reaction mixture, in order to at least partially convert the azetidine salt to the free base. A variety of bases may be used, including, organic and inorganic bases. Examples of organic bases include, but are not limited to TEA, DIPEA, and pyridine.

In one embodiment, the alcohol solvent contains EtOH, an azetidine salt 9 is used, the reducing agent is STAB, and the external base is TEA or DIPEA. In another embodiment, the alcohol solvent contains isopropanol, tert-butanol and/or tert-amyl alcohol and the reducing agent contains pyridine borane. In another embodiment, the alcohol solvent contains isopropanol, tert-butanol and/or tert-amyl alcohol and the reducing agent contains $NaBH_3CN$. In an embodiment, the alcohol solvent contains tert-amyl alcohol, and the reducing agent contains pyridine borane. In another embodiment, the solvent contains tert-amyl alcohol, the reducing agent contains pyridine borane, and the HCl salt of azetidine 9 is used. In a different embodiment, the solvent contains tert-butyl alcohol, the reducing agent contains pyridine borane, and the HCl salt of azetidine 9 is used. In yet another embodiment, the solvent contains isopropanol, the reducing agent contains pyridine borane, and the HCl salt of azetidine 9 is used. In another embodiment, the solvent contains tert-amyl alcohol, the reducing agent contains pyridine borane, and the tosylate salt of azetidine 9 is used. In a different embodiment, the solvent contains tert-butyl alcohol, the reducing agent contains pyridine borane, and the tosylate salt of azetidine 9 is used. In yet another embodiment, the solvent contains isopropanol, the reducing agent contains pyridine borane, and the tosylate salt of azetidine 9 is used.

The removal of the PG group can occur at any point during the synthesis of the compounds of Formula A, B, and C. In one embodiment, it is removed before the reaction between compounds 8 and 9. When the PG group is methyl, $BBr_3$, can be used to remove it.

Generally, a pharmaceutically acceptable salt of a compound of Formula A, B, and C can be formed by treating the free base of Formula A, B, and C with a pharmaceutically acceptable acid in a suitable solvent. Formula A, B, and C can be isolated, and the salt formed in a separate step, or the salt form can be isolated without isolating the neutral material of Formula A, B, and C. The formation of pharmaceutically acceptable salts is well known. See, for example, P. Stahl, et al., HANDBOOK OF PHARMACEU- TICAL SALTS: PROPERTIES, SELECTION AND USE, (VCHA/Wiley-VCH, 2002); Gould, P. L., "Salt selection for basic drugs," International Journal of Pharmaceutics, 33: 201-217 (1986); Bastin, R. J., et al. "Salt Selection and Optimization Procedures for Pharmaceutical New Chemical Entities," Organic Process Research and Development, 4: 427-435 (2000); and Berge, S. M., et al., "Pharmaceutical Salts," Journal of Pharmaceutical Sciences, 66: 1-19, (1977). One of ordinary skill in the art will appreciate that a compound of Formula A, B, and C as described herein is readily converted to and may be isolated as a pharmaceutically acceptable salt. Examples of useful salts include, but are not limited to, the HCl salt, the benzenesulfonic acid salt (besylate), the 4-methybenzenesulfonic acid salt (tosylate), or the methylsulfonic acid salt (mesylate). In one embodiment, the pharmaceutically acceptable salt is the besylate salt. In another embodiment, the pharmaceutically acceptable salt is the tosylate salt. In still another embodiment, the pharmaceutically acceptable salt is the mesylate. In another embodiment, the pharmaceutically acceptable salt is the HCl salt.

In an embodiment, the compound of Formula A or a pharmaceutically acceptable salt thereof is a compound of Formula B

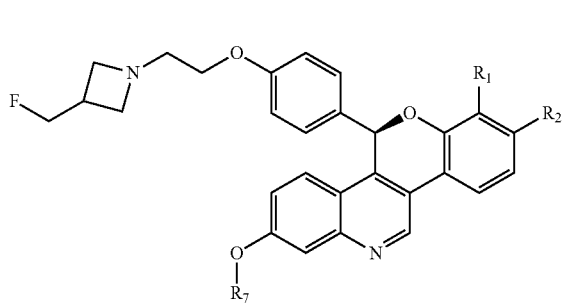

or a pharmaceutically acceptable salt thereof, wherein either $R_1$ or $R_2$ is independently Cl, F, —$CF_3$, or —$CH_3$, and the other is H; and $R_7$ is H or PG.

In a preferred embodiment, the compound of form B is

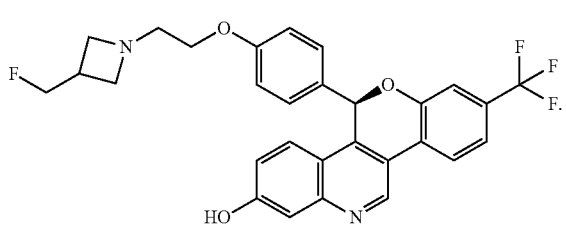 [SMILES: Oc1ccc2c3c(cnc2c1)-c1ccc(C(F)(F)F)cc1O[C@@H]3c1ccc(OCCN2CC(CF)C2)cc1]

Scheme 4 illustrates a chiral synthesis of enantiomer B.

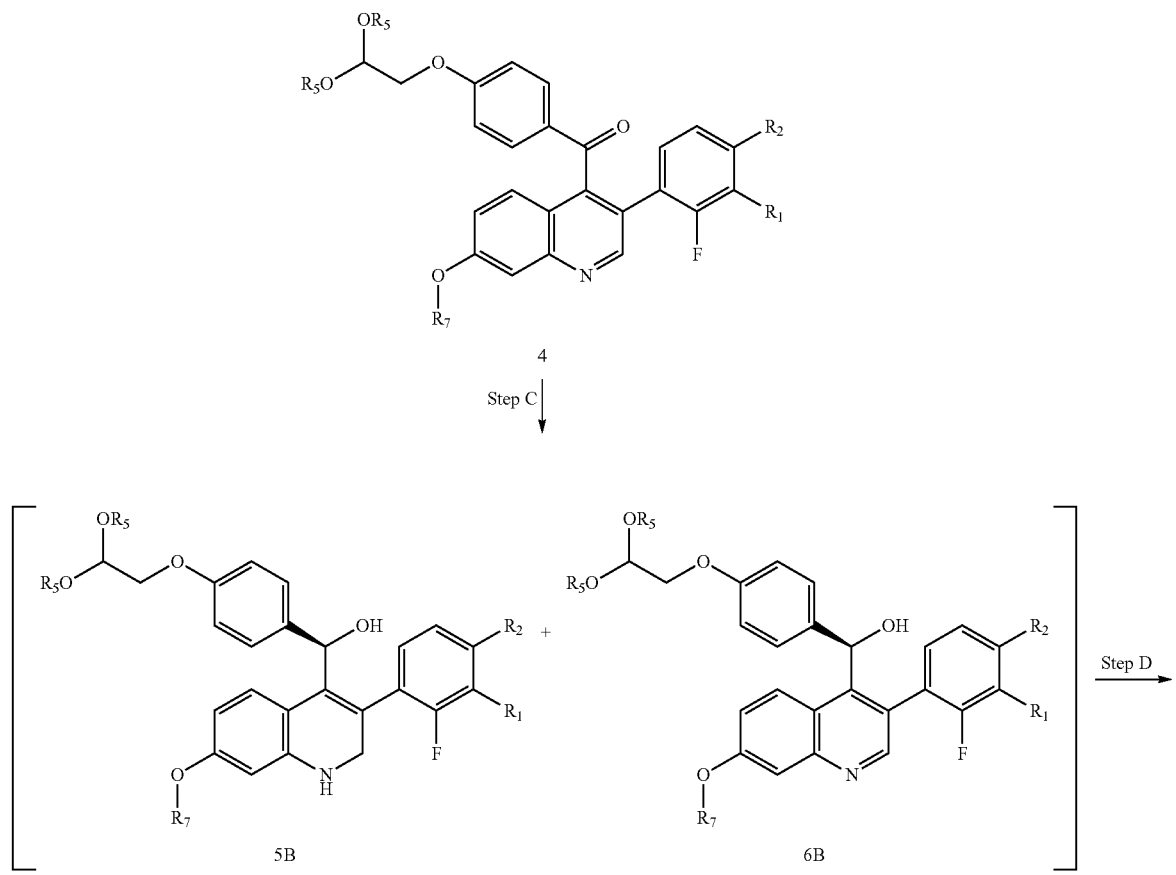

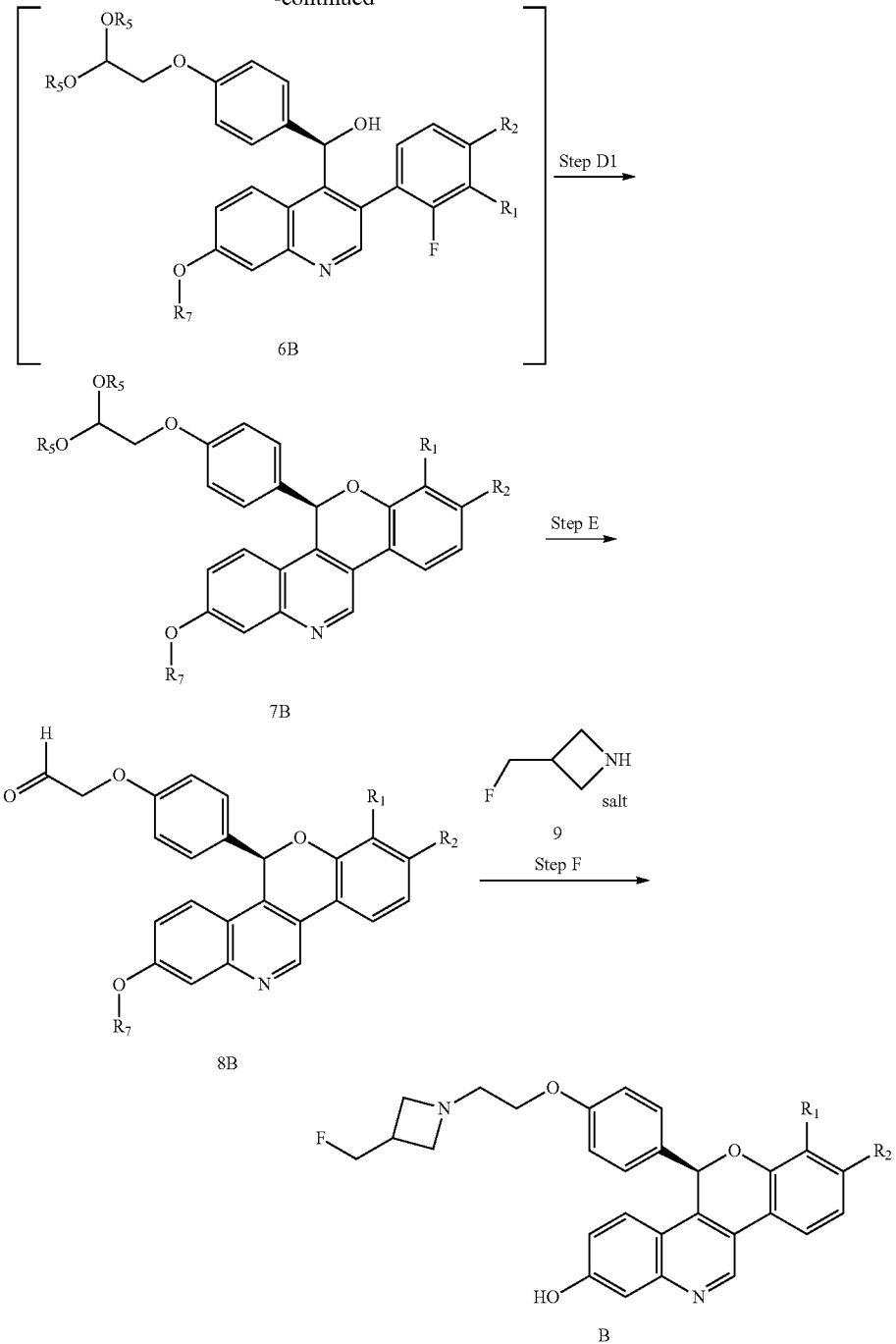

Scheme 4 illustrates a chiral synthesis of enantiomer B. A key step in making the chiral compounds is setting the chirality of the alcohol in Step C, as this chirality is preserved in steps D, D1, E, and F.

In Step C, pro-chiral compound 4 undergoes a chiral reduction to selectively form the chiral alcohol 6B. During the reduction, the dihydroquinoline 5B is also formed. Without wishing to be bound by a theory, it is believed residual Pd in compound 4 (from the Suzuki coupling) leads to over-reduction of compound 6B to form compound 5B. As noted in Scheme 3, dihydroquinoline 5B may be oxidized to quinoline 6B using at least one oxidizing agent. Examples of suitable oxidizing agents include, but are not limited to MnO$_2$, DDQ, and oxygen. In some embodiments, the oxidizing agent is MnO$_2$. In another embodiment, the oxidizing agent is oxygen in an inert gas. While various oxygen concentrations may be used, it is desirable to use lower concentrations, as doing so will help to minimize any fire hazards. In an embodiment, the oxidizing agent is about 5% oxygen in nitrogen. The mixture of 5B and 6B is typically not isolated before the oxidation reaction.

In one embodiment, a chiral reducing protocol that can be used is the CBS chiral ketone reduction. The CBS reduction utilizes a borolidine reagent, such as trimethyl borate in combination with a chiral amino compound, such as diphenyl-[(2R)-pyrrolidin-2-yl]methanol, and a boron based reducing agent, such as BH$_3$-Me$_2$S. Other borolidine reagents that could be used include triethylborate, triisopropyl borate, tri-t-butyl borate, or tributylborane. Other boron based reducing agents that could be used include borane N,N-diethylaniline, BH$_3$-THF, or other borane sources. Other reducing protocols, such as enzymatic or catalytic hydrogenation, may be used.

Examples of compounds 5B and 6B that can be made using the methods disclosed herein include, but are not limited to:

(R)-4-((4-(2,2-Diethoxyethoxy)phenyl)(hydroxy)methyl)-3-(2-fluoro-4-(trifluoromethyl)phenyl)quinolin-7-ol

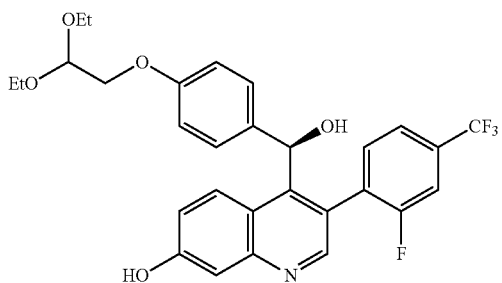 [SMILES: CCOC(COc1ccc([C@@H](O)c2c(-c3ccc(C(F)(F)F)cc3F)cnc3cc(O)ccc23)cc1)OCC]

4-[(R)-[4-(2,2-Dimethoxyethoxy)phenyl]-hydroxy-methyl]-3-[2-fluoro-4-(trifluoromethyl)phenyl]quinolin-7-ol

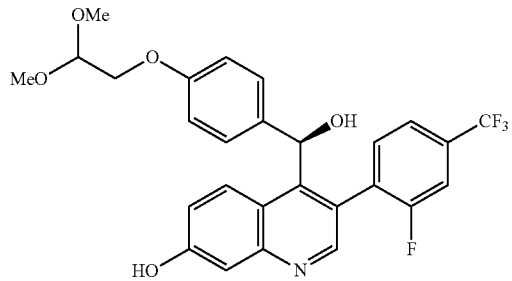 [SMILES: COC(COc1ccc([C@@H](O)c2c(-c3ccc(C(F)(F)F)cc3F)cnc3cc(O)ccc23)cc1)OC]

4-[(R)-[4-(1,3-Dioxolan-2-ylmethoxy)phenyl]-hydroxy-methyl]-3-[2-fluoro-4-(trifluoromethyl)phenyl]quinolin-7-ol

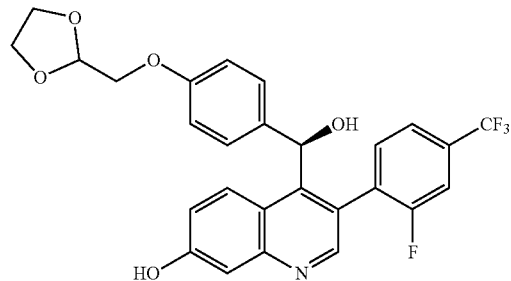 [SMILES: Oc1ccc2c([C@H](O)c3ccc(OCC4OCCO4)cc3)c(-c3ccc(C(F)(F)F)cc3F)cnc2c1]

4-[(R)-[4-(1,3-Dioxan-2-ylmethoxy)phenyl]-hydroxy-methyl]-3-[2-fluoro-4-(trifluoromethyl)phenyl]quinolin-7-ol

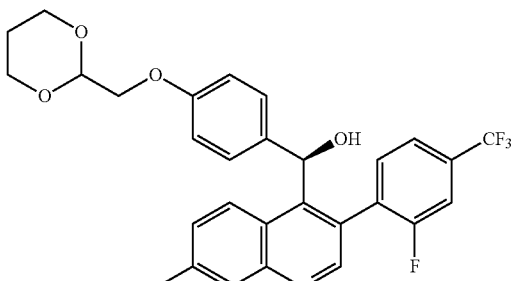

4-[(R)-[4-(2,2-Diethoxyethoxy)phenyl]-hydroxy-methyl]-3-[2-fluoro-4-(trifluoromethyl)phenyl]-1,2-dihydroquinolin-7-ol

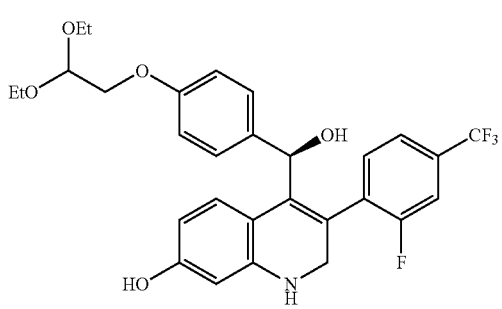 [SMILES: CCOC(COc1ccc([C@@H](O)C2=C(c3ccc(C(F)(F)F)cc3F)CNc3cc(O)ccc32)cc1)OCC]

| | -continued |
|---|---|
| 4-[(R)-[4-(2,2-Dimethoxyethoxy)phenyl]-hydroxy-methyl]-3-[2-fluoro-4-(trifluoromethyl)phenyl]-1,2-dihydroquinolin-7-ol | 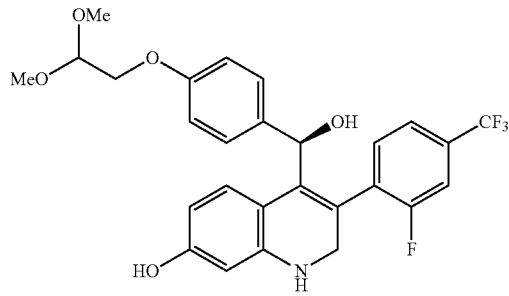 [SMILES: COC(COc1ccc([C@@H](O)C2=C(c3ccc(C(F)(F)F)cc3F)CNc3cc(O)ccc32)cc1)OC] |
| 4-[(R)-[4-(1,3-Dioxolan-2-ylmethoxy)phenyl]-hydroxy-methyl]-3-[2-fluoro-4-(trifluoromethyl)phenyl]-1,2-dihydroquinolin-7-ol | 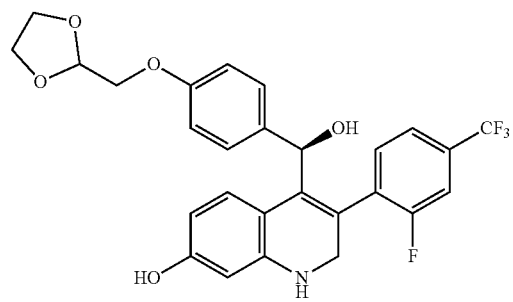 [SMILES: Oc1ccc2c(c1)NCC(c1ccc(C(F)(F)F)cc1F)=C2[C@H](O)c1ccc(OCC2OCCO2)cc1] |
| 4-[(R)-[4-(1,3-Dioxan-2-ylmethoxy)phenyl]-hydroxy-methyl]-3-[2-fluoro-4-(trifluoromethyl)phenyl]-1,2-dihydroquinolin-7-ol | 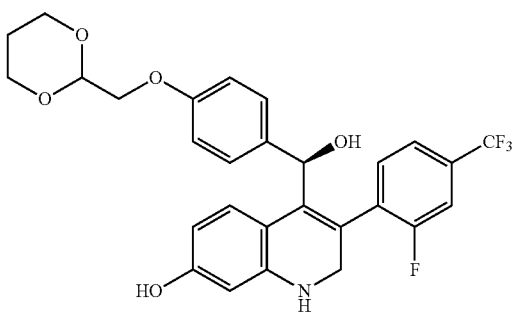 [SMILES: Oc1ccc2c(c1)NCC(c1ccc(C(F)(F)F)cc1F)=C2[C@H](O)c1ccc(OCC2OCCCO2)cc1] |

The above compounds are also potential impurities in the compound of Formula B, where $R_7$ is H, $R_1$ is H and $R_2$ is $CF_3$.

Steps D, E, and F in Scheme 4 can be completed as described in Scheme 3. Preferably, the oxidation, deprotection, cyclization, and coupling reactions maintain the stereochemical integrity of the starting material, i.e., little, if any, of the stereochemical purity is lost. For example, if compound 6B is 95±5% a single enantiomer (as determined by chiral HPLC or chiral gas chromatography (GC)), the resulting product, compound 7B is 95±5% a single enantiomer (as determined by chiral HPLC or chiral GC). Likewise, when compound 7B or 8B is 97% a single enantiomer, then compounds 8B and A are also 97% a single enantiomer.

Examples of compounds of Formula 7B that can be made using the methods disclosed herein include, but are not limited to

| (R)-5-4-(2,2-Diethoxyethoxy)phenyl)-8-(trifluoromethyl)-5H-[1]benzopyrano[4,3-c]quinolin-2-ol | 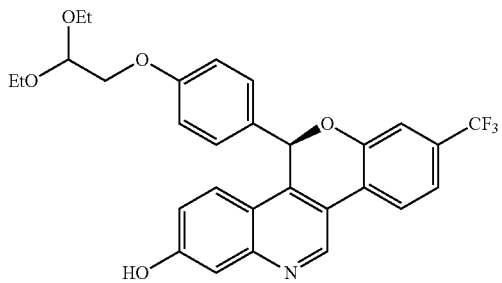 [SMILES: CCOC(COc1ccc([C@H]2Oc3cc(C(F)(F)F)ccc3-c3cnc4cc(O)ccc4c32)cc1)OCC] |

-continued

| | |
|---|---|
| (5R)-5-[4-(2,2-Dimethoxyethoxy)phenyl]-8-(trifluoromethyl)-5H-chromeno[4,3-c]quinolin-2-ol | 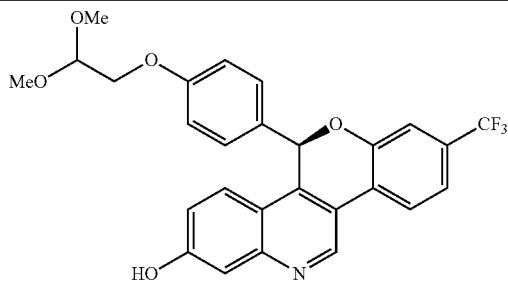 |
| (5R)-5-[4-(1,3-Dioxolan-2-ylmethoxy)phenyl]-8-(trifluoromethyl)-5H-chromeno[4,3-c]quinolin-2-ol | 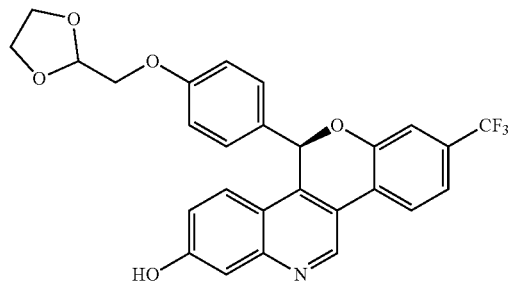 [SMILES: Oc1ccc2c3c(cnc2c1)-c1ccc(C(F)(F)F)cc1O[C@@H]3c1ccc(OCC2OCCO2)cc1] |
| (5R)-5-[4-(1,3-Dioxan-2-ylmethoxy)phenyl]-8-(trifluoromethyl)-5H-chromeno[4,3-c]quinolin-2-ol | 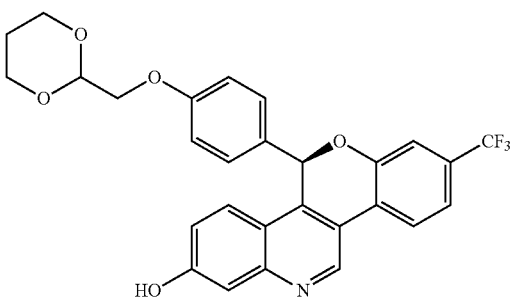 [SMILES: Oc1ccc2c3c(cnc2c1)-c1ccc(C(F)(F)F)cc1O[C@@H]3c1ccc(OCC2OCCCO2)cc1] |

The above compounds are also potential impurities in the compound of Formula B, where $R_7$ is H, $R_1$ is H and $R_2$ is $CF_3$.

Additional, potential impurities in the compounds of Formula B, wherein $R_7$ and $R_1$ are H and $R_2$ is $CF_3$, include the following:

| | |
|---|---|
| (5R)-5-[4-(2,2-Diethoxyethoxy)phenyl]-8-(trifluoromethyl)-11,12-dihydro-5H-chromeno[4,3-c]quinolin-2-ol | 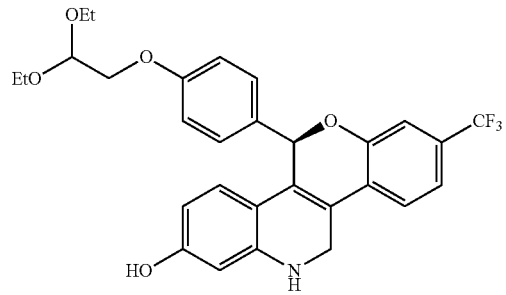 [SMILES: CCOC(COc1ccc([C@H]2Oc3cc(C(F)(F)F)ccc3C3=C2c2ccc(O)cc2NC3)cc1)OCC] |
| (5R)-5-[4-(2,2-Dimethoxyethoxy)phenyl]-8-(trifluoromethyl)-11,12-dihydro-5H-chromeno[4,3-c]quinolin-2-ol | 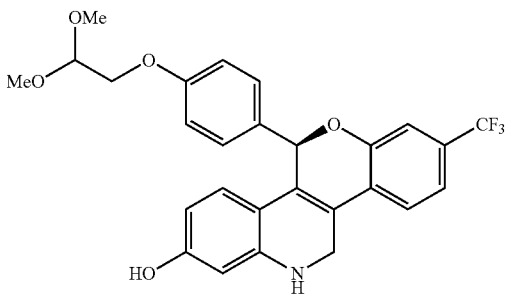 [SMILES: COC(COc1ccc([C@H]2Oc3cc(C(F)(F)F)ccc3C3=C2c2ccc(O)cc2NC3)cc1)OC] |

| | |
|---|---|
| (5R)-5-[4-(1,3-Dioxolan-2-ylmethoxy)phenyl]-8-(trifluoromethyl)-11,12-dihydro-5H-chromeno[4,3-c]quinolin-2-ol | 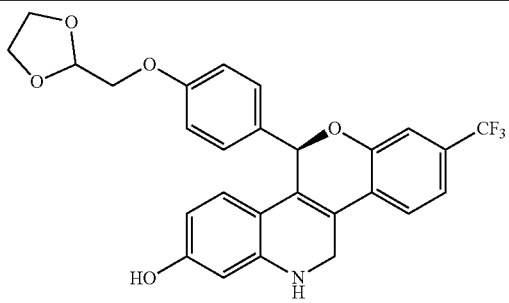 |
| (5R)-5-[4-(1,3-Dioxan-2-ylmethoxy)phenyl]-8-(trifluoromethyl)-11,12-dihydro-5H-chromeno[4,3-c]quinolin-2-ol | 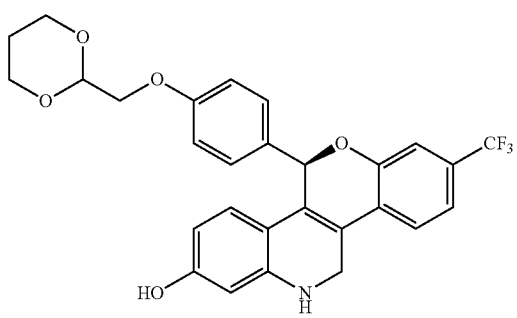 [SMILES: Oc1ccc2c(c1)NCC1=C2[C@@H](c2ccc(OCC3OCCCO3)cc2)Oc2cc(C(F)(F)F)ccc21] |
| 2-[4-[(5R)-2-Hydroxy-8-(trifluoromethyl)-11,12-dihydro-5H-chromeno[4,3-c]quinolin-5-yl]phenoxy]acetaldehyde | 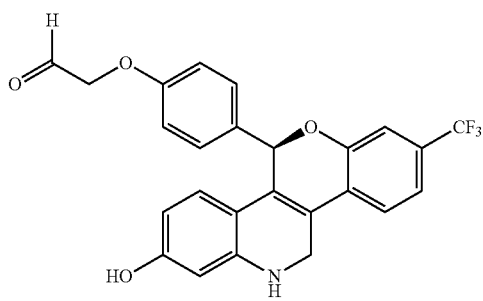 [SMILES: O=CCOc1ccc([C@H]2Oc3cc(C(F)(F)F)ccc3C3=C2c2ccc(O)cc2NC3)cc1] |

The above dihydroquinoline compounds are derived from the compounds 5B that were not oxidized to compounds 6B.

Still other, potential impurities in the compounds of Formula B, wherein $R_7$ and $R_1$ are H and $R_2$ is $CF_3$, include the following:

| | |
|---|---|
| (R)-2-(4-(2-Hydroxy-8-(trifluoromethyl)-5H-[1]benzopyrano[4,3-c]quinolin-5-yl)phenoxy)acetaldehyde | 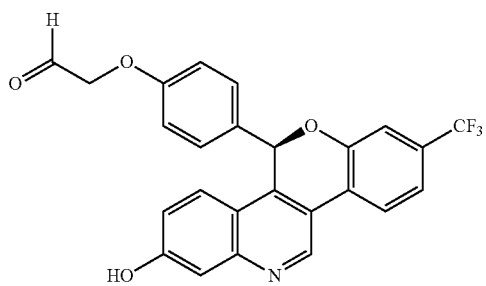 [SMILES: O=CCOc1ccc([C@H]2Oc3cc(C(F)(F)F)ccc3-c3cnc4cc(O)ccc4c32)cc1] |

| | |
|---|---|
| 2-[4-[2-Hydroxy-8-(trifluoromethyl)-5H-chromeno[4,3-c]quinolin-5-yl]phenoxy]acetic acid | 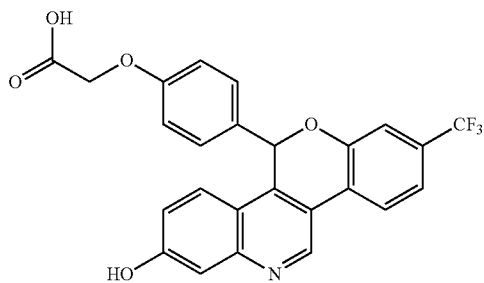 [SMILES: O=C(O)COc1ccc(C2Oc3cc(C(F)(F)F)ccc3-c3cnc4cc(O)ccc4c32)cc1] |
| (5R)-5-[4-[2-[[2-(Chloromethyl)-3-fluoro-propyl]amino]ethoxy]phenyl]-8-(trifluoromethyl)-5H-chromeno[4,3-c]quinolin-2-ol | 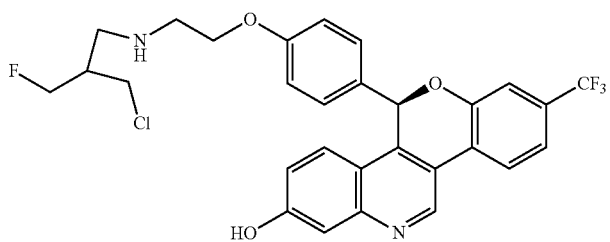 |
| (5R)-5-[4-[2-[[2-(Chloromethyl)-3-fluoro-propyl]amino]ethoxy]phenyl]-8-(trifluoromethyl)-11,12-dihydro-5H-chromeno[4,3-c]quinolin-2-ol | 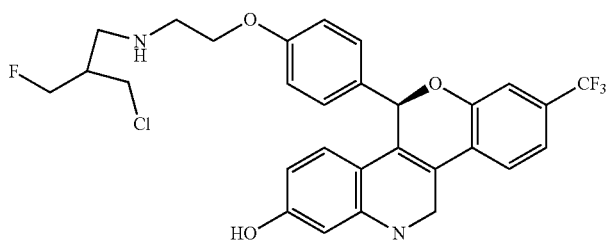 [SMILES: Oc1ccc2c(c1)NCC1=C2[C@@H](c2ccc(OCCNCC(CF)CCl)cc2)Oc2cc(C(F)(F)F)ccc21] |
| (5R)-5-[4-(2-Hydroxyethoxy)phenyl]-8-(trifluoromethyl)-5H-chromeno[4,3-c]quinolin-2-ol | 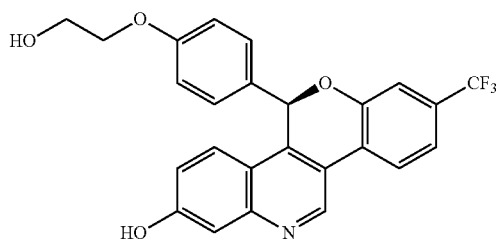 [SMILES: OCCOc1ccc([C@H]2Oc3cc(C(F)(F)F)ccc3-c3cnc4cc(O)ccc4c32)cc1] |
| (5R)-5-[4-(2-Hydroxyethoxy)cyclohexa-2,4-dien-1-yl]-8-(trifluoromethyl)-11,12-dihydro-5H-chromeno[4,3-c]quinolin-2-ol | 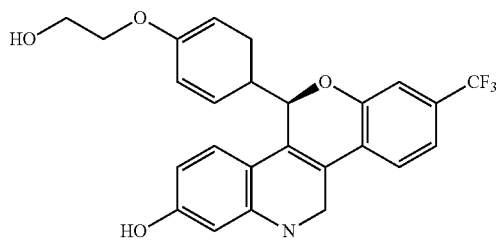 [SMILES: OCCOC1=CCC([C@H]2Oc3cc(C(F)(F)F)ccc3C3=C2c2ccc(O)cc2NC3)C=C1] |
| [4-(1,3-Dioxolan-2-ylmethoxy)phenyl]-[3-[2-fluoro-4-(trifluoromethyl)phenyl]-7-hydroxy-4-quinolyl]methanone | 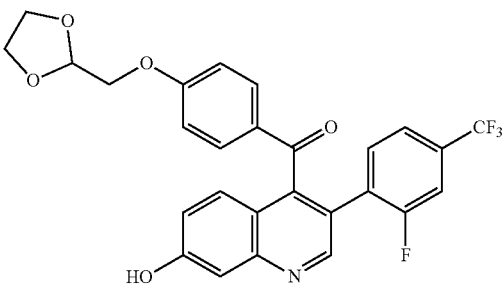 [SMILES: O=C(c1ccc(OCC2OCCO2)cc1)c1c(-c2ccc(C(F)(F)F)cc2F)cnc2cc(O)ccc12] |

| | |
|---|---|
| [4-(2,2-Dimethoxyethoxy)phenyl]-[3-[2-fluoro-4-(trifluoromethyl)phenyl]-7-hydroxy-4-quinolyl]methanone | 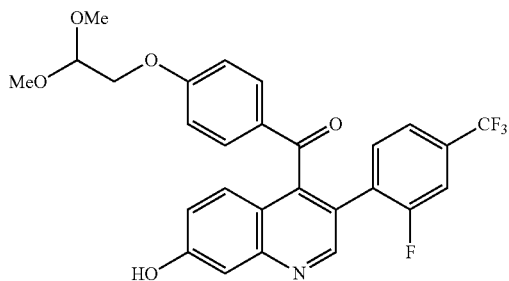 [SMILES: COC(COc1ccc(C(=O)c2c(-c3ccc(C(F)(F)F)cc3F)cnc3cc(O)ccc23)cc1)OC] |
| [4-(1,3-Dioxan-2-ylmethoxy)phenyl]-[3-[2-fluoro-4-(trifluoromethyl)phenyl]-7-hydroxy-4-quinolyl]methanone | 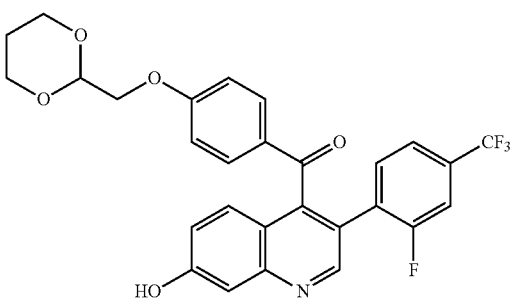 [SMILES: O=C(c1ccc(OCC2OCCCO2)cc1)c1c(-c2ccc(C(F)(F)F)cc2F)cnc2cc(O)ccc12] |
| (4-(2,2-Diethoxyethoxy)phenyl)(3-(2-fluoro-4-(trifluoromethyl)phenyl)-7-hydroxyquinolin-4-yl)methanone | 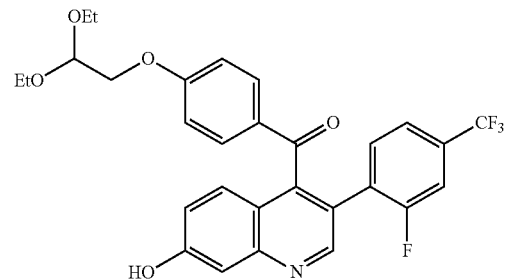 [SMILES: CCOC(COc1ccc(C(=O)c2c(-c3ccc(C(F)(F)F)cc3F)cnc3cc(O)ccc23)cc1)OCC] |
| (5R)-5-[4-[2-[3-(Fluoromethyl)azetidin-1-yl]ethoxy]phenyl]-8-(trifluoromethyl)-11,12-dihydro-5H-chromeno[4,3-c]quinolin-2-ol | 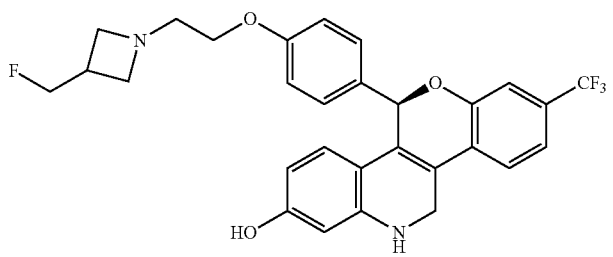 [SMILES: Oc1ccc2c(c1)NCC1=C2[C@@H](c2ccc(OCCN3CC(CF)C3)cc2)Oc2cc(C(F)(F)F)ccc21] |

Scheme 5 illustrates an alternate method for preparing compound 4. In Scheme 5, compound 1 is reacted with a —CH$_2$CH(OR$_5$)$_2$ synthon to form compound 15, which then undergoes a Suzuki coupling to form compound 4.

Scheme 5

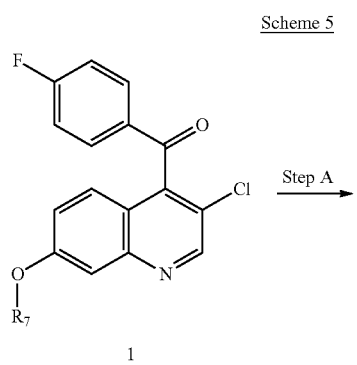

1

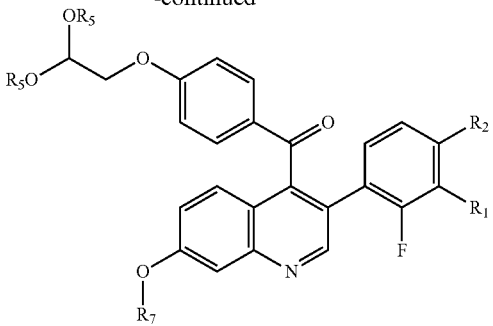

4

In Scheme 5, Step A may be carried out as described in Step B of Scheme 3, and Scheme 5, Step B may be carried out as described in Step A of Scheme 3. Such a re-ordering may require less catalyst and boronic acid which can result in a more economical process. The reordered reaction can provide similar quality and yield.

An alternate method for preparing compound 3 is illustrated in Scheme 6.

Scheme 6

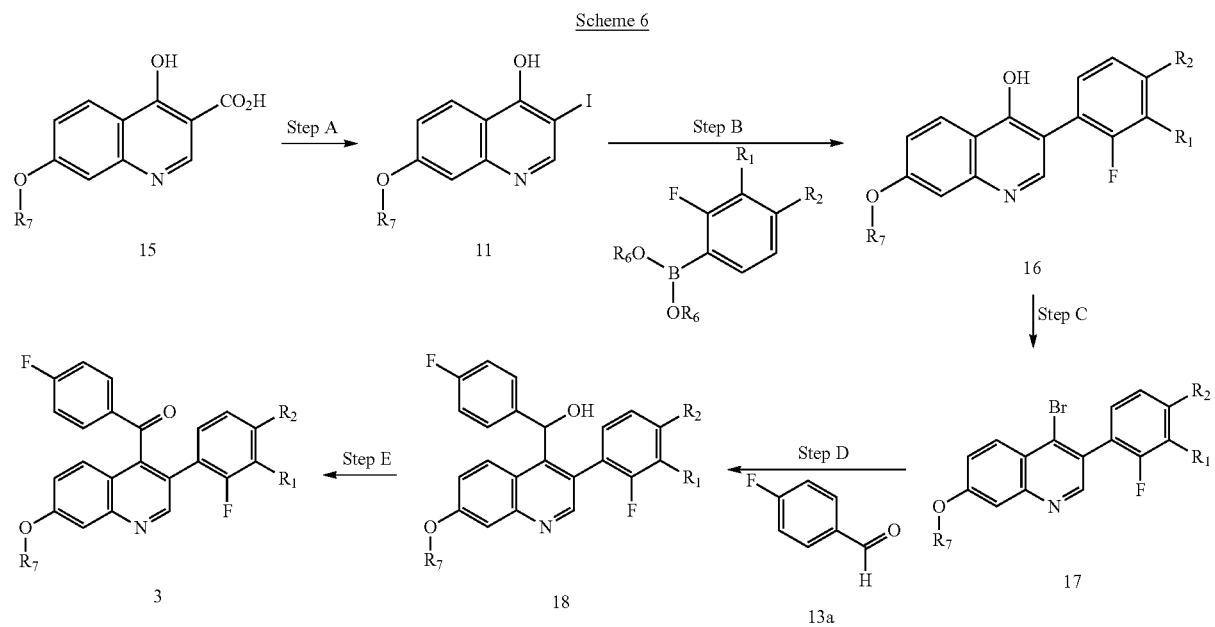

-continued

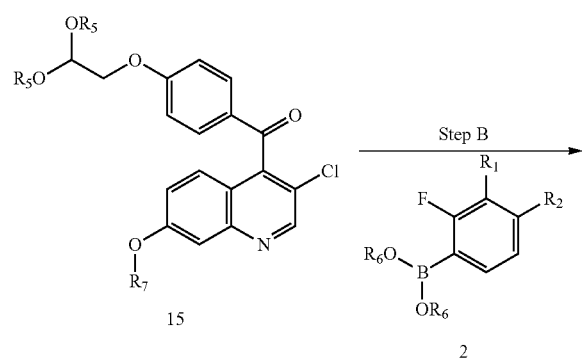

2

In Scheme 6, R$_7$ is a protecting group, or it is H. Step A is a decarboxylative iodination, which is carried out by reacting 7-methoxy-4-hydroxyquinoline, compound 15, with I$_2$ and K$_3$PO$_4$ in ACN with heating to about 50° C. The resulting product, 3-iodo-7-methoxyquinolin-4-ol, compound 11, is then cross coupled with compound 2, in Step B. This cross-coupling step may be carried out as described in Step A of Scheme 3. While various conditions can be used (see Step A of Scheme 3), suitable sets of conditions involve the use of either PEPPSI™-IPr or (Amphos)$_2$PdCl$_2$ as the catalyst, K$_2$CO$_3$ as the base, and tert-amyl alcohol/ACN/water or dioxane/water as the solvent.

The bromination in Step C may be carried out as described in Step B of Scheme 1. Compound 17, above, is shown as the bromide. While not shown in Scheme 6, the bromide could be replaced with chloride or iodide, using chlorination or iodination methods known in the art. While phosphorous tribromide or phosphorous oxybromide may be used in the bromination step, in one embodiment, phosphorous oxybromide is preferred. In an alternate embodiment, the bromination in Step C can be completed before the cross-coupling in Step B. In Step D, a Grignard addition can be completed as described in Scheme 1, Step C.

Alternatively, Compound 17 can be treated with a strong base to thereby generate an anion, which can react with aldehyde 13a to give compound 18. Examples of strong bases include tert-BuLi and n-BuLi. When n-BuLi is used as the strong base, 4-butyl-3-[2-fluoro-4-(trifluoromethyl)phenyl]-7-methoxy-quinoline and 3-methoxy-9-(trifluoromethyl)benzo[3,4]cyclobuta[1,2-c]quinoline may form as impurities (see structures in table below).

The oxidation of the benzylic alcohol of compound 18 (Step E) can be completed as described in Step D of Scheme 1. The deprotection of the hydroxy of compound 3 can occur at any step in the synthesis with a suitable reagent, for example, when PG is methyl, a suitable reagent is BBr$_3$.

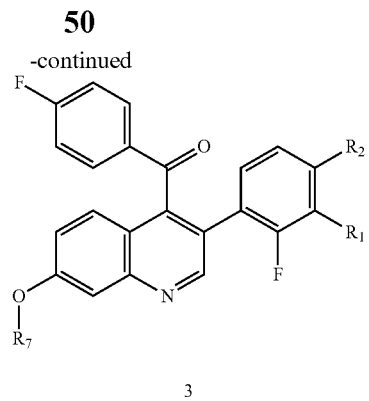

3

Scheme 7 illustrates an alternative method of preparing compound 3. In Scheme 7, compound 17, is reacted with compound 13, wherein R$_3$ is Cl, or N(OMe)R$_4$, where R$_4$ =C$_1$-C$_4$ alkyl and R$_7$ is a protecting group or H. This reaction affords the ketone 3, without the intermediacy of an alcohol.

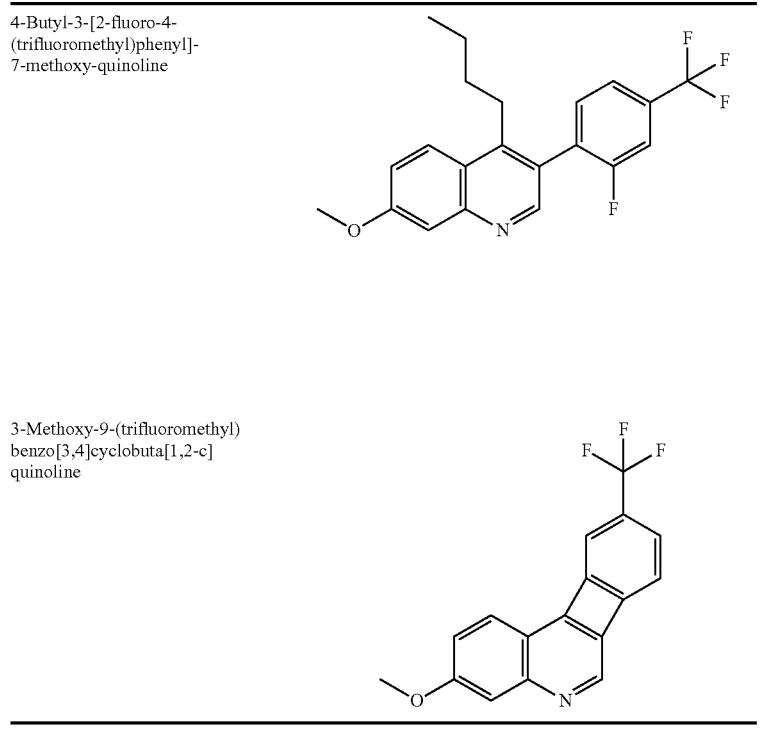

| | |
|---|---|
| 4-Butyl-3-[2-fluoro-4-(trifluoromethyl)phenyl]-7-methoxy-quinoline | |
| 3-Methoxy-9-(trifluoromethyl)benzo[3,4]cyclobuta[1,2-c]quinoline | |

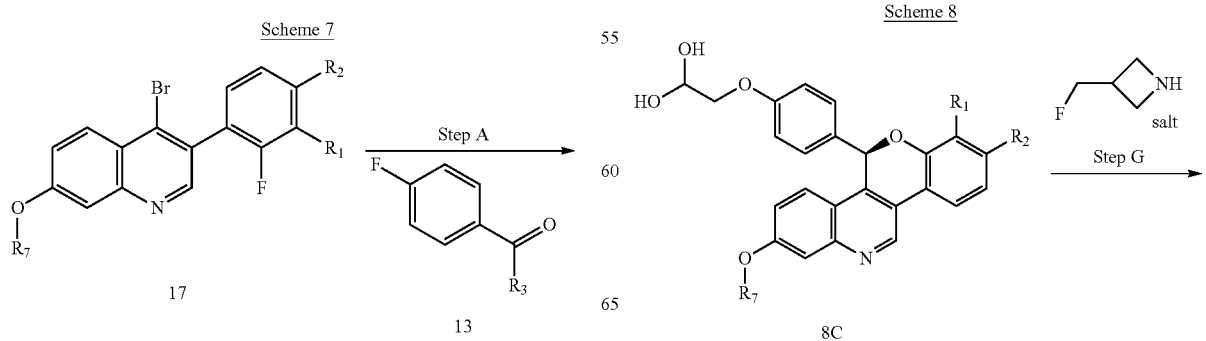

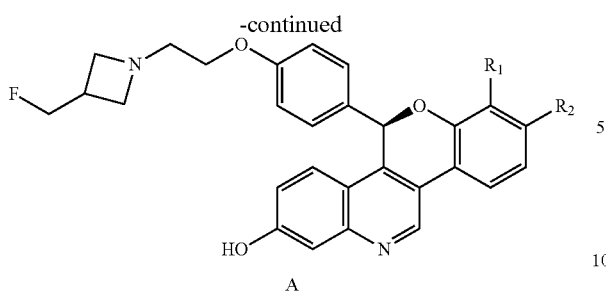

A

Scheme 8 illustrates an alternative method of preparing compound A. In Scheme 8, step G, $R_7$ is a protecting group, or it is H. In Step G, the aldehyde hydrate can be reacted in a similar fashion with an amine as outlined in Scheme 3, Step F to obtain Compound A.

In some embodiments, the compounds of Formula A, Formula B, or Formula C, have a purity of at least 98.1% area, 98.2% area, 98.3% area, 98.4% area, 98.5% area, 98.6% area, 98.7% area, 98.8% area, 98.9% area, 99.0% area, 99.1% area, 99.2% area, 99.3% area, 99.4% area, 99.5% area or 99.6% area.

In another embodiment, disclosed herein are compounds of Formula A

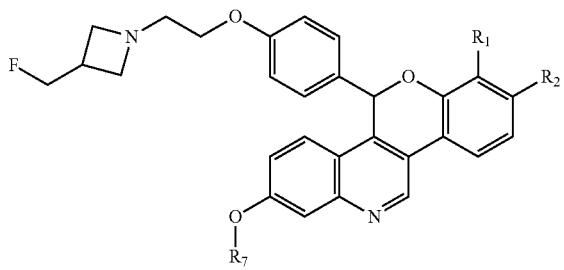

or a pharmaceutically acceptable salt thereof, wherein $R_1$ is H, $R_2$ is —$CF_3$, and $R_7$ is H, obtainable by reacting a compound of structure 8:

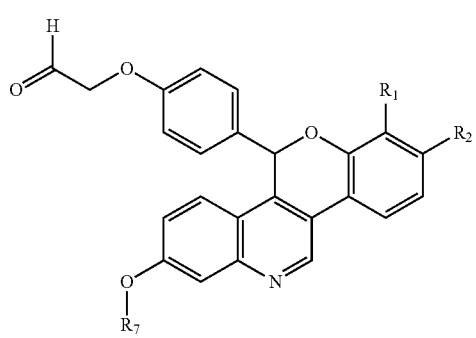

8 or a salt thereof, in a solvent with an amine of structure 9

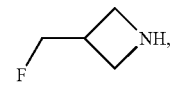

9 or a salt thereof, and a reducing agent. Suitable reducing reagents are disclosed elsewhere, in this application.

In a still another embodiment, disclosed herein are compounds of Formula A

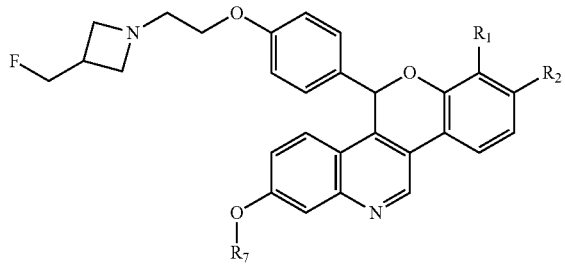

or a pharmaceutically acceptable salt thereof, wherein either $R_1$ or $R_2$ is independently Cl, F, —$CF_3$, or —$CH_3$, and the other is H; and $R_7$ is H or PG, wherein the compounds of Formula A are at least 98% area, as measured using HPLC. The compounds of Formula A are prepared using the methods disclosed herein.

In an embodiment, disclosed is a compound of Formula B

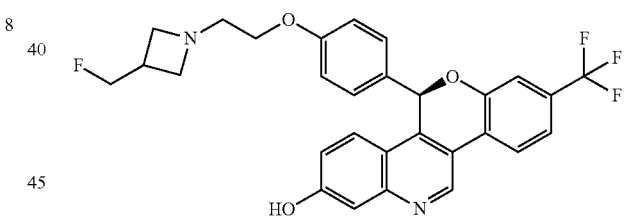

wherein $R_1$ is H, $R_2$ is —$CF_3$ and $R_7$ is H, obtainable by reacting the aldehyde of formula 8b or the hydrated form of the aldehyde 8b:

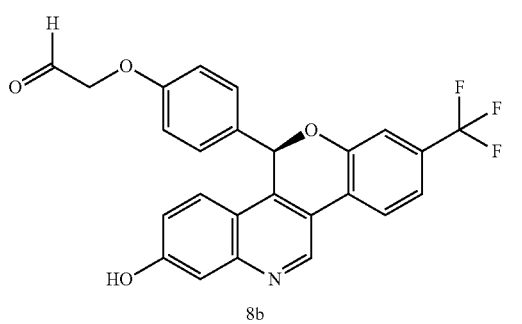

8b

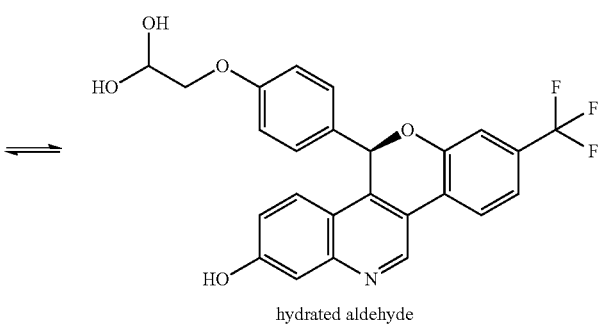

hydrated aldehyde or a salt thereof, in a solvent with an amine of structure 9

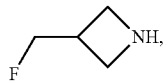

9 or a salt thereof, and a reducing agent. Suitable reducing reagents are disclosed elsewhere, in this application. In an embodiment, the compound of Formula B is at least 98% area, as measured using HPLC. In another embodiment, the compound of Formula B is at least 92% enantiomeric excess, as measured using HPLC. In yet another embodiment, the compound of Formula B contains dimer and/or dimer 2. In still yet another embodiment, the compound of Formula B contains (5R)-5-[4-(2-hydroxyethoxy)phenyl]-8-(trifluoromethyl)-5H-chromeno[4,3-c]quinolin-2-ol. In another embodiment, the compound of Formula B contains (5R)-5-[4-[2-[3-(chloromethyl)azetidin-1-yl]ethoxy]phenyl]-8-(trifluoromethyl)-5H-chromeno[4,3-c]quinolin-2-ol. In an embodiment, the compound of Formula B contains (5R)-5-[4-[2-[[2-(chloromethyl)-3-fluoro-propyl]amino]ethoxy]phenyl]-8-(trifluoromethyl)-5H-chromeno[4,3-c]quinolin-2-ol. In yet another embodiment, the compound of Formula B contains less than 1% of dihydroquinoline and quinoline based impurities, as determined using HPLC. In an embodiment, the compound of Formula B contains less than 1% of dihydroquinoline based impurities, as determined using HPLC. In yet another embodiment, the compound of Formula B contains less than 1% of quinoline based impurities, as determined using HPLC.

In another embodiment, disclosed is a compound of Formula B

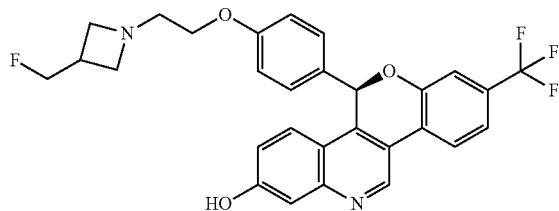 [SMILES: Oc1ccc2c3c(cnc2c1)-c1ccc(C(F)(F)F)cc1O[C@@H]3c1ccc(OCCN2CC(CF)C2)cc1]

or a pharmaceutically acceptable salt thereof, wherein at least one of the following applies:
  the compound of Formula B is at least 98% area, as measured using HPLC;
  the compound of Formula B is at least 92% enantiomeric excess, as measured using HPLC;
  the compound of Formula B contains dimer and/or dimer 2;
  the compound of Formula B contains (5R)-5-[4-(2-hydroxyethoxy)phenyl]-8-(trifluoromethyl)-5H-chromeno[4,3-c]quinolin-2-ol;
  the compound of Formula B contains (5R)-5-[4-[2-[3-(chloromethyl)azetidin-1-yl]ethoxy]phenyl]-8-(trifluoromethyl)-5H-chromeno[4,3-c]quinolin-2-ol;
  the compound of Formula B contains (5R)-5-[4-[2-[[2-(chloromethyl)-3-fluoro-propyl]amino]ethoxy]phenyl]-8-(trifluoromethyl)-5H-chromeno[4,3-c]quinolin-2-ol;
  the compound of Formula B contains less than 1% of dihydroquinoline and quinoline based impurities, as determined using HPLC;
  the compound of Formula B contains less than 1% of dihydroquinoline based impurities, as determined using HPLC; and
  the compound of Formula B contains less than 1% of quinoline based impurities, as determined using HPLC.

In another embodiment, disclosed herein are compounds of Formula A

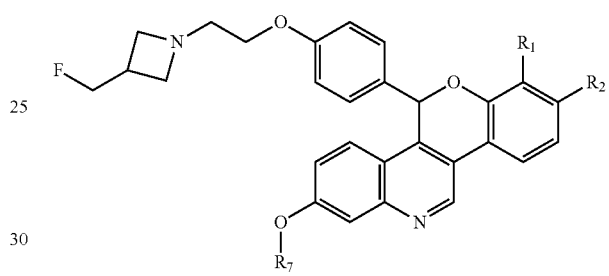

or a pharmaceutically acceptable salt thereof, wherein either $R_1$ or $R_2$ is independently Cl, F, —$CF_3$, or —$CH_3$, and the other is H; and $R_7$ is H or PG, obtainable by reacting a compound of structure 8:

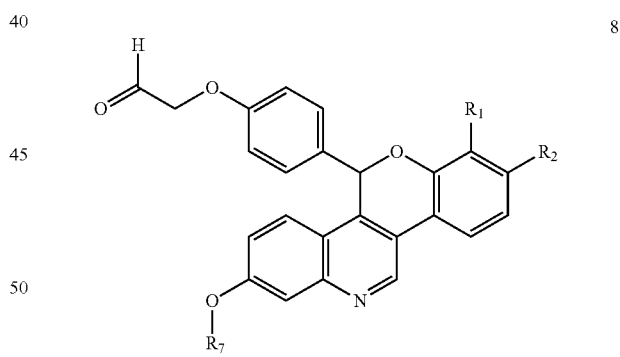

8 or a salt thereof, in a solvent with an amine of structure 9

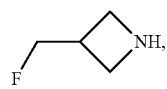

9 or a salt thereof, and a reducing agent, wherein the compounds of Formula A, B, and C have an enantiomeric excess of at least about 92%. Suitable reducing agents are disclosed elsewhere, in this application.

In an embodiment, disclosed herein are compounds of Formula A

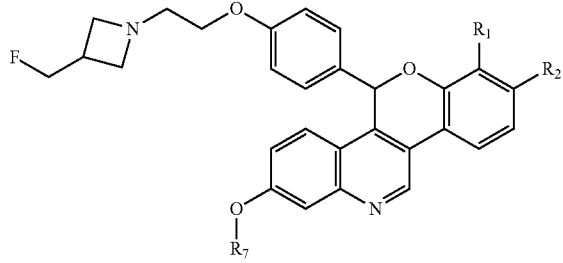

or a pharmaceutically acceptable salt thereof, wherein either $R_1$ or $R_2$ is independently Cl, F, —$CF_3$, or —$CH_3$, and the other is H; and $R_7$ is H or PG, which contain a $C_3$-$C_7$ alcohol. The compounds of Formula A are prepared using the methods disclosed herein. The presence and quantity of a $C_3$-$C_7$ alcohol is determined using gas chromatography.

In some embodiments, the $C_3$-$C_7$ alcohol is a $C_3$-$C_4$ alcohol or a $C_3$-$C_5$ alcohol or a $C_3$-$C_6$ alcohol, or a $C_4$-$C_5$ alcohol, or a $C_4$-$C_6$ alcohol, or a $C_4$-$C_7$ alcohol or a $C_5$-$C_6$ alcohol, or a $C_5$-$C_7$ alcohol, or a $C_6$-$C_7$ alcohol. In an additional embodiment, the $C_3$-$C_7$ alcohol is a $C_3$ alcohol, or it is a $C_4$ alcohol, or it is a $C_5$ alcohol, or it is a $C_6$ alcohol, or it is a $C_7$ alcohol. A $C_3$ alcohol is isopropanol; a $C_4$ alcohol is tert-butanol, and a $C_5$ alcohol is tert-amyl alcohol. In one embodiment, the $C_3$-$C_7$ alcohol comprises isopropanol, tert-butanol and/or tert-amyl alcohol. In an embodiment, the compounds of Formula A contain isopropanol. In an embodiment, the compounds of Formula A contain tert-butanol. In an embodiment, the compounds of Formula A contain tert-amyl alcohol.

When the compounds of Formula A, B, and C contain a $C_3$-$C_7$ alcohol, the $C_3$-$C_7$ alcohol is present in an amount of no more than 1% by weight or less than or no more than 0.9% by weight or no more than 0.8% by weight or less than or no more than 0.7% by weight or no more than 0.6% by weight or less than or no more than 0.5% by weight or no more than 0,4% by weight or less than or no more than 0.3% by weight or no more than 0.2% by weight or less than or no more than 0.1% by weight.

Disclosed herein is a compound of Formula A

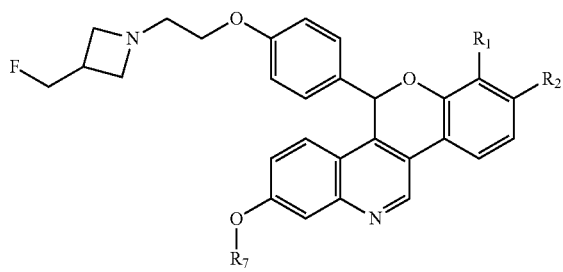

or a pharmaceutically acceptable salt thereof, wherein $R_1$ is H, $R_2$ is —$CF_3$, and $R_7$ is H, which contain (5R)-5-[4-(2-hydroxyethoxy)phenyl]-8-(trifluoromethyl)-5H-chromeno[4,3-c]quinolin-2-ol. The compounds of Formula A can be prepared using the methods disclosed herein. When present, the (5R)-5-[4-(2-hydroxyethoxy)phenyl]-8-(trifluoromethyl)-5H-chromeno[4,3-c]quinolin-2-ol is present at levels of 0.5% or 0.4% or 0.3% or below, as measured by HPLC.

Disclosed herein is a compound of Formula A

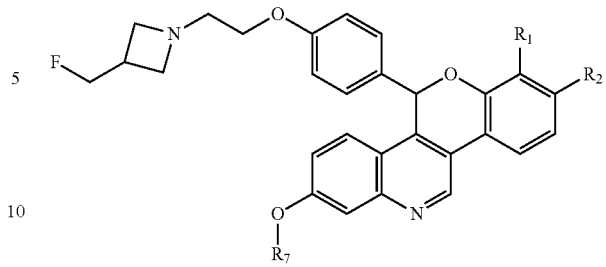

or a pharmaceutically acceptable salt thereof, wherein $R_1$ is H, $R_2$ is —$CF_3$, and $R_7$ is H, obtainable by reacting a compound of structure 8:

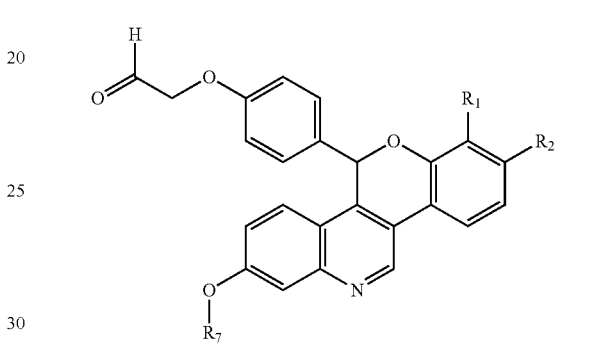

or a salt thereof, in a solvent with an amine of structure 9

9

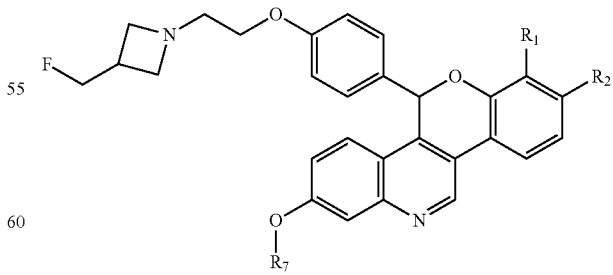

or a salt thereof, and a reducing agent, wherein the compound of Formula A contains (5R)-5-[4-(2-hydroxyethoxy)phenyl]-8-(trifluoromethyl)-5H-chromeno[4,3-c]quinolin-2-ol. When present, the (5R)-5-[4-(2-hydroxyethoxy)phenyl]-8-(trifluoromethyl)-5H-chromeno[4,3-c]quinolin-2-ol is present at levels of about 0.5% or about 0.4% or about 0.3% or below, as measured by HPLC.

Disclosed herein is a compound of Formula A

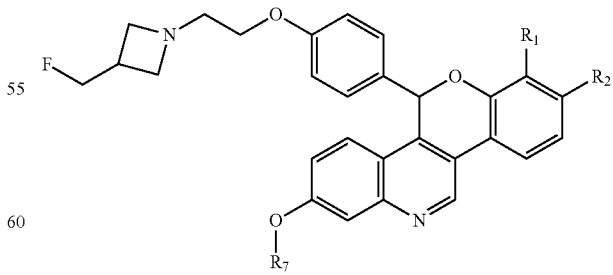

or a pharmaceutically acceptable salt thereof, wherein $R_1$ is H, $R_2$ is —$CF_3$, and $R_7$ is H, which contain (5R)-5-[4-[2-[3-(chloromethyl)azetidin-1-yl]ethoxy]phenyl]-8-(trifluoromethyl)-5H-chromeno[4,3-c]quinolin-2-ol. The compounds of Formula A can be prepared using the methods disclosed herein. When present, the (5R)-5-[4-[2-[3-(chloromethyl)azetidin-1-yl]ethoxy]phenyl]-8-(trifluoromethyl)-5H-chromeno[4,3-c]quinolin-2-ol is present at levels from 0.05% to 0.5%, as determined using HPLC.

Disclosed herein is a compound of Formula A

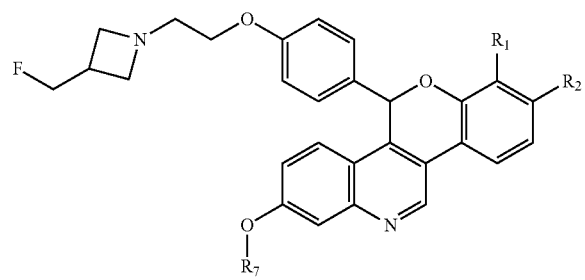

or a pharmaceutically acceptable salt thereof, wherein $R_1$ is H, $R_2$ is —$CF_3$, and $R_7$ is H, obtainable by reacting a compound of structure 8:

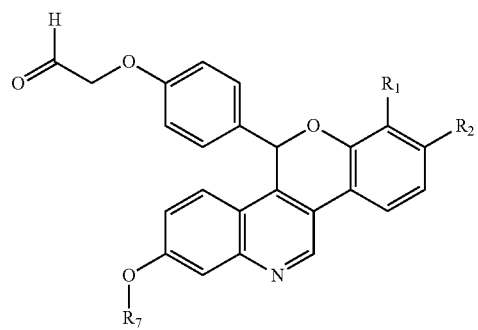

8 or a salt thereof, in a solvent with an amine of structure 9

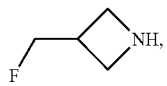

9

Or a salt thereof, and a reducing agent, wherein the compound of Formula A contains (5R)-5-[4-[2-[3-(chloromethyl)azetidin-1-yl]ethoxy]phenyl]-8-(trifluoromethyl)-5H-chromeno[4,3-c]quinolin-2-ol. When present, the (5R)-5-[4-[2-[3-(chloromethyl)azetidin-1-yl]ethoxy]phenyl]-8-(trifluoromethyl)-5H-chromeno[4,3-c]quinolin-2-ol present at levels from about 0.05% to about 0.5%, as determined using HPLC.

Disclosed herein is a compound of Formula A

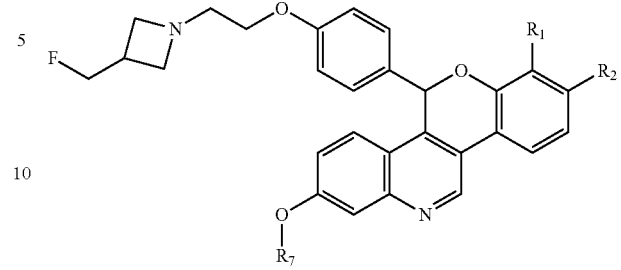

or a pharmaceutically acceptable salt thereof, wherein $R_1$ is H, $R_2$ is —$CF_3$, and $R_7$ is H, which contains (5R)-5-[4-[2-[[2-(chloromethyl)-3-fluoro-propyl]amino]ethoxy]phenyl]-8-(trifluoromethyl)-5H-chromeno[4,3-c]quinolin-2-ol. The compounds of Formula A can be prepared using the methods disclosed herein. When present, the (5R)-5-[4-[2-[[2-(chloromethyl)-3-fluoro-propyl]amino]ethoxy]phenyl]-8-(trifluoromethyl)-5H-chromeno[4,3-c]quinolin-2-ol is present at levels from 0.01% to 0.5%, as determined using HPLC.

Disclosed herein is a compound of Formula A

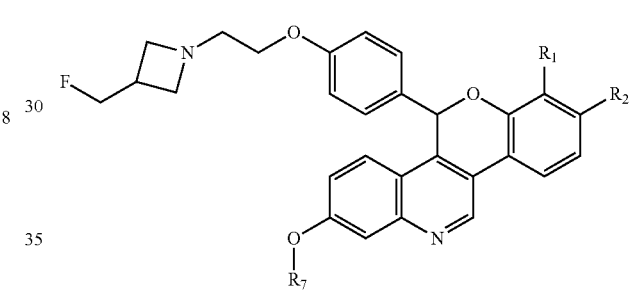

or a pharmaceutically acceptable salt thereof, wherein $R_1$ is H, $R_2$ is —$CF_3$, and $R_7$ is H, obtainable by reacting a compound of structure 8:

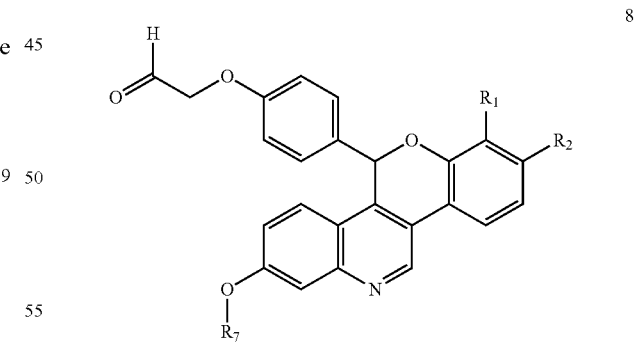

8 or a salt thereof, in a solvent with an amine of structure 9

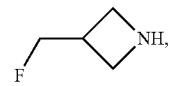

9

Or a salt thereof, and a reducing agent, wherein the compound of Formula A contains (5R)-5-[4-[2-[[2-(chloromethyl)-3-fluoro-propyl]amino]ethoxy]phenyl]-8-(trifluoromethyl)-5H-chromeno[4,3-c]quinolin-2-ol. When present, the (5R)-5-[4-[2-[[2-(chloromethyl)-3-fluoro-propyl]amino]ethoxy]phenyl]-8-(trifluoromethyl)-5H-chromeno[4,3-c]quinolin-2-ol is present at levels from about 0.01% to about 0.5%, as determined using HPLC.

Disclosed herein is a compound of Formula A

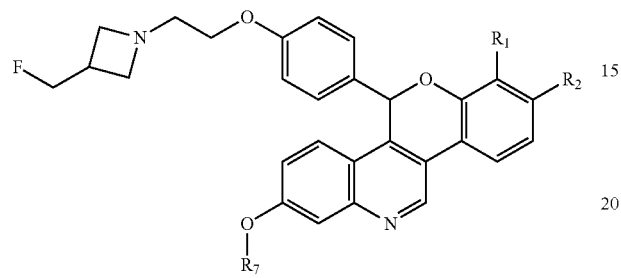

or a pharmaceutically acceptable salt thereof, wherein $R_1$ is H and $R_2$ is —$CF_3$, and $R_7$ is H which contains the following dimer:

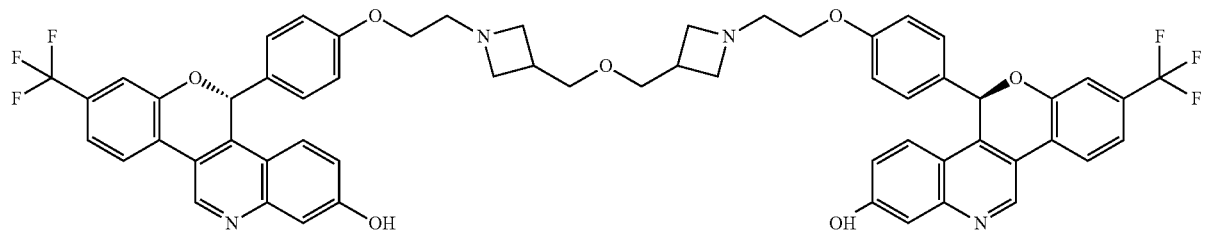 [SMILES: Oc1ccc2c3c(cnc2c1)-c1ccc(C(F)(F)F)cc1O[C@@H]3c1ccc(OCCN2CC(COCC3CN(CCOc4ccc([C@H]5Oc6cc(C(F)(F)F)ccc6-c6cnc7cc(O)ccc7c65)cc4)C3)C2)cc1]

The compound of Formula A can be prepared using the methods disclosed herein. When present, the dimer is present at levels from about 0.01% to about 0.5%, as determined using HPLC. The dimer may form during the jet milling of the compound of Formula A, i.e., the dimer forms after the compound of Formula A is isolated.

Also disclosed herein is a compound of Formula A

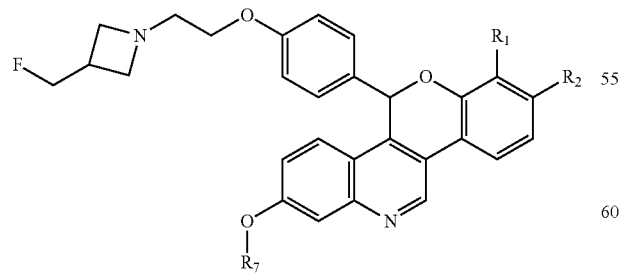

or a pharmaceutically acceptable salt thereof, wherein $R_1$ is H, $R_2$ is —$CF_3$, and $R_7$ is H, which contain dimer 2:

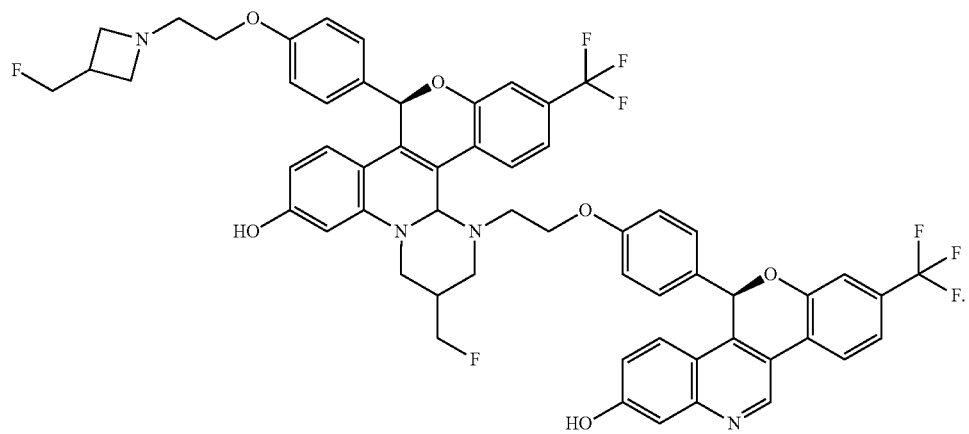 [SMILES: Oc1ccc2c(c1)N1CC(CF)CN(CCOc3ccc([C@H]4Oc5cc(C(F)(F)F)ccc5-c5cnc6cc(O)ccc6c54)cc3)C1C1=C2[C@@H](c2ccc(OCCN3CC(CF)C3)cc2)Oc2cc(C(F)(F)F)ccc21]

The compounds of Formula A can be prepared using the methods disclosed herein. When present, dimer 2 is present at levels from about 0.01% to about 0.5%, as determined using HPLC. Dimer 2 may form during the jet milling of the compound of Formula A, i.e., the dimer forms after the compound of Formula A is isolated.

In some embodiments, the compound of Formula A may contain the dimer, dimer 2 or mixtures thereof. Preferably, the amount of dimer and/or dimer 2 in the compound of Formula A is minimized. More preferably, the amount of dimer and/or dimer 2 in the compound of Formula A is undetectable or even more preferably zero, as measured using HPLC.

Without wishing to be bound to a theory, it is believed that dimer and dimer 2 form from or through interactions with amorphous (i.e., non-crystalline) Formula A. Jet milling appears to increase the formation of dimer and/or dimer 2, because it increases the amorphous Formula A content. Upon 6 months of storage in stressed conditions, 40° C. at 75% relative humidity, about 0.2% by HPLC of dimer and about 0.2% by HPLC of dimer 2 were identified in the compound of Formula A. If dimer and/or dimer 2 form pre-storage, they are present in amounts less than about 0.05%, as measured by HPLC. Reducing the amorphous Formula A content should reduce the amount of dimer and dimer 2 that form.

Disclosed herein is a compound of Formula A

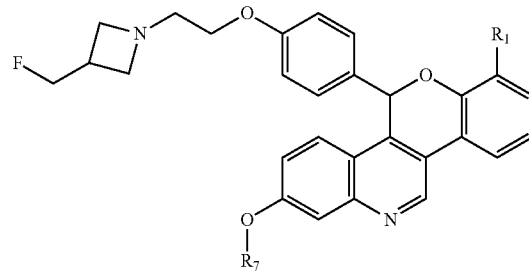

or a pharmaceutically acceptable salt thereof, wherein $R_1$ is H, $R_2$ is —$CF_3$, and $R_7$ is H, obtainable by reacting a compound of structure 8:

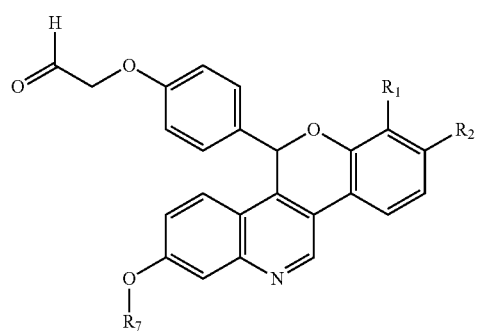

or a salt thereof, in a solvent with an amine of structure 9

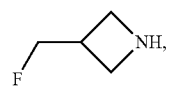

Or a salt thereof, and a reducing agent, wherein the compound of Formula A contains 4-Butyl-3-[2-fluoro-4-(trifluoromethyl)phenyl]-7-methoxy-quinoline. When present, the 4-Butyl-3-[2-fluoro-4-(trifluoromethyl)phenyl]-7-methoxy-quinoline is present at levels less than about 0.5%, as determined using HPLC.

Disclosed herein is a compound of Formula A or a pharmaceutically acceptable salt thereof, wherein $R_1$ is H, $R_2$ is —$CF_3$, and $R_7$ is H, obtainable by reacting a compound of structure 8:

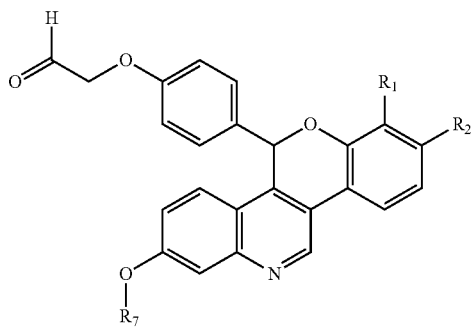

or a salt thereof, in a solvent with an amine of structure 9

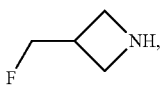

Or a salt thereof, and a reducing agent, wherein the compound of Formula A contains 3-Methoxy-9-(trifluoromethyl)benzo[3,4]cyclobuta[1,2-c]quinoline. When present, the 3-Methoxy-9-(trifluoromethyl)benzo[3,4]cyclobuta[1,2-c]quinoline is present at levels less than about 0.5%, as determined using HPLC.

Disclosed herein is a compound of Formula A

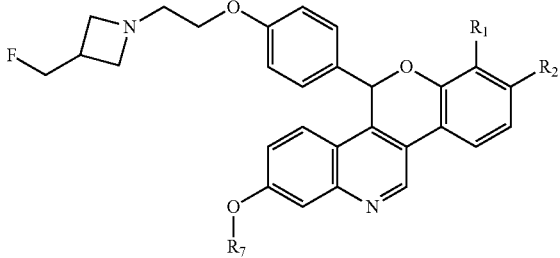

or a pharmaceutically acceptable salt thereof, wherein $R_1$ is H and $R_2$ is —$CF_3$, and $R_7$ is H which contain 3-Methoxy-9-(trifluoromethyl)benzo[3,4]cyclobuta[1,2-c]quinoline in an amount less than about 0.5%, as determined using HPLC.

Disclosed herein is a compound of Formula A

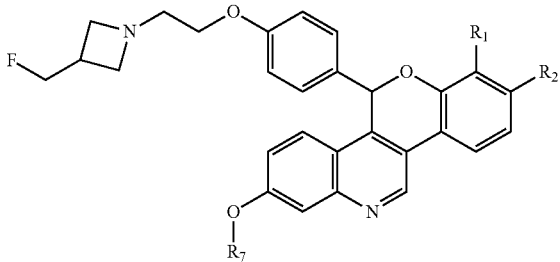

or a pharmaceutically acceptable salt thereof, wherein $R_1$ is H and $R_2$ is —$CF_3$, and $R_7$ is H which contain 4-Butyl-3-[2-fluoro-4-(trifluoromethyl)phenyl]-7-methoxy-quinoline in an amount less than about 0.5%, as determined using HPLC.

All of the methods disclosed herein can be used to prepare enantiomerically enriched compounds of Formula A. Preferably, when enantiomerically enriched compounds of Formula A are prepared to afford compounds of Formula B and Formula C, the compounds of Formula B and Formula C have an enantiomeric excess of at least about 90%. Enantiomeric excess can be determined using chiral chromatography (such as chiral HPLC) or other methods known in the art. More preferably, the compounds have an enantiomeric excess of at least about 91% or at least about 92% or at least about 93% or at least about 94% or at least about 95% or at least about 96% or at least about 97% or at least about 97.5% or at least about 98% or at least about 98.5% or at least about 99% or at least about 99.1%.

In an embodiment, in any of the previously disclosed compounds of Formula A, $R_7$ is H.

In another embodiment, all of the previously disclosed compounds of Formula A have the R-enantiomeric form.

In yet another embodiment, in any of the previously disclosed compounds of Formula A, $R^1$ is H.

In still yet another embodiment, in any of the previously disclosed compounds of Formula A, $R^2$ is $CF_3$.

In an embodiment, in any of the previously disclosed compounds of Formula A, $R_7$ is PG. In some occurrence, PG is methyl.

In an embodiment, in any of the previously disclosed compounds of Formula A,

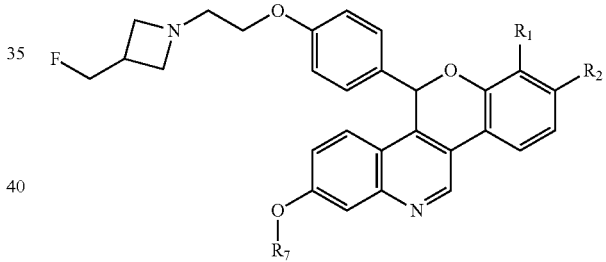

or a pharmaceutically acceptable salt thereof, wherein either $R_1$ or $R_2$ is independently Cl, F, —$CF_3$, or —$CH_3$, and the other is H; and $R_7$ is H or PG, containing less than 0.15% area of one or more dihydroquinoline or quinoline based impurities. Dihydroquinoline or quinoline based impurities are compounds that contain a dihydroquinoline and/or quinoline ring system that were used to make the compounds of Formula A. Intermediates used to prepare/made during the synthesis of the compounds of Formula A, using the methods disclosed herein, are examples of dihydroquinoline and quinoline based impurities, as are impurities derived from the intermediates. In some embodiments, the total amount of dihydroquinoline or quinoline impurities present is less than 1.0% area, or less than 0.9% area, less than 0.8% area, or less than 0.7% area, 1.0% area, or less than 0.9% area, less than 0.8% area, or less than 0.7% area, less than 0.6% area, or less than 0.5% area, less than 0.4% area, or less than 0.3% area, or less than 0.2% area or less than 0.15% area or less than 0.1% area.

In an embodiment, the chiral reduction of the ketone group in compound 4 is performed using the CBS protocol, which comprises using diphenyl-[(2R)-pyrrolidin-2-yl]methanol, trimethyl borate and borane N,N-diethylaniline.

In a further embodiment, the chiral reduction is performed in a solvent that comprises at least one of THF and 2-MeTHF. Preferably, the resulting chiral alcohol is at least 95% ee, as measured using chiral chromatography.

Also disclosed herein are methods of preparing pyridine borane, the process comprising: reacting a pyridinium salt and sodium borohydride in a solvent. While various pyridinium salts may be used, in one embodiment, pyridinium p-tosylate is preferred. Solvents that may be used in the preparation of pyridine borane include aprotic solvents. Examples of aprotic solvents include, but are not limited to ethers. Preferred ethers include tetrahydrofuran and 2-methyltetrahydrofuran. The formation of the pyridine borane is typically performed at a temperature of about 15-30° C. or 19-25° C. In an embodiment, the reaction is performed at room temperature, which is about 19 to about 21° C. The reaction time may vary, but is typically from about 1 to about 24 hours. In some embodiments, the reaction time is about 2 to about 12 hours. Once completed, the reaction may be filtered through a filtrant, such as diatomaceous earth. The product may be used without purification or it may be purified using methods known in the art.

The following preparations and examples further illustrate the invention. Reference standards and $^1$H NMR can be used to determine purity. 1,3,5-trimethoxy benzene can be used as an $^1$H NMR reference internal standard.

Preparation 1

3-Chloro-7-methoxyquinolin-4-ol

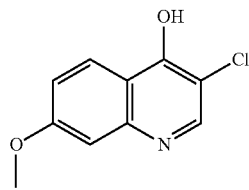

Scheme 1, Step A: Add DMF (1240 L, 8.0 L/kg) and 7-methoxyquinolin-4-ol (155.04 kg, 885.03 mol) together. Stir at 27.5° C. for 30 min. Adjust the temperature to 30° C. Add NCS (118.18 kg, 885.03 mol) portionwise, maintaining a reaction temperature under 45° C. Adjust the temperature to 40° C. Stir for 24 h. Cool to 15° C. Add water (4651 L, 30 L/kg). Mix at 25° C. for 1 h, then filter and wash the product with water (775 L, 5 L/kg). Dry under reduced pressure at 65° C. to provide the title compound as a pale brown solid (153.34 kg, 82.6% yield).

Preparation 2

4-Bromo-3-chloro-7-methoxyquinoline

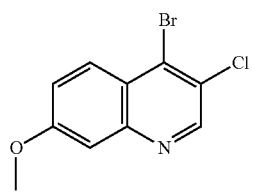

Scheme 1, Step B: Combine 3-chloro-7-methoxyquinoline-4-ol (154.32 kg, 736.2 mol) and toluene (1543 L, 10 L/kg). Stir at 27.5° C. for 30 min. Add P(O)Br$_3$ (253.3 kg, 883.39 mol) maintaining the temperature under 40° C. Heat to 100° C. for 3 h. Cool to 5° C., then add a solution of NaOH (104.94 kg, 2623.6 mol) in water (1312 L, 8.5 L/kg). Concentrate to 8.5 L/kg under reduced pressure, while keeping the temperature below 70° C. Add water (308.6 L, 2.0 L/kg). Concentrate to 8.5 L/kg under reduced pressure below 70° C. Add water (308.6 L, 2.0 L/kg). Concentrate to 8.5 L/kg under reduced pressure below 70° C. Cool to 27.5° C. Add water (1543 L, 10 L/kg). Cool to 5° C. Filter and wash product with water (308.6 L, 2.0 L/kg). Add a solution of NaOH (15.43 kg, 385.8 mol) in water (771.6 L, 5.0 L/kg) and stir at 30° C. for 5 min. Filter and wash solids with water (463.0 L, 3.0 L/kg). Dry under reduced pressure at 65° C. to provide the title compound as a brown solid (174.20 kg, 86.8% yield).

Alternative Preparation 2

4-Bromo-3-chloro-7-methoxyquinoline

Scheme 1, Step B: Add 3-chloro-7-methoxyquinoline-4-ol (25.0 g, 119 mmol) and DMF (225 mL, 9 mL/g) together. Cool to 0° C. Add PBr$_3$ maintaining a temperature below 10° C. Heat to 47.5° C. Stir for 3 h. Cool to 25° C. Add a solution of 20 w/w % Na$_2$CO$_3$ (250 mL). Filter and wash the solids with water (125 mL). Dry under reduced pressure to provide the title compound as a brown solid (29.0 g, 89% yield).

Preparation 3

3-Iodo-7-methoxyquinolin-4-ol

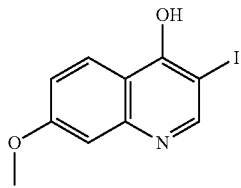

Scheme 6, Step A: Add together 4-hydroxy-7-methoxyquinoline-3-carboxylic acid (10.00 g, 43.34 mmol), K$_3$PO$_4$ (11.3 g, 52.2 mmol), and ACN (100 mL). Add iodine (22.0 g, 86.7 mmol) and heat to 50° C. for 16 h. Filter the product, wash with ACN and dry under reduced pressure at 40° C. to give the title compound (9.70 g, 72.1% yield). $^1$H NMR (400 MHz, d$_6$-DMSO) δ 11.98 (s, 1H), 8.48-8.35 (m, 1H), 8.07-7.95 (m, 1H), 7.01-6.94 (m, 2H), 3.86 (s, 3H). $^{13}$C NMR (101 MHz, d$_6$-DMSO) δ 172.97, 162.36, 144.76, 141.78, 127.89, 117.41, 114.75, 99.55, 81.11, 55.98.

Preparation 4

3-(2-Fluoro-4-(trifluoromethyl)phenyl)-7-methoxy-quinolin-4-ol

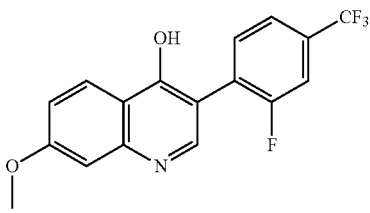 [SMILES: COc1ccc2c(O)c(-c3ccc(C(F)(F)F)cc3F)cnc2c1]

Scheme 6, Step B: Add 3-iodo-7-methoxy-quinolin-4-ol (5.00 g, 16.6 mmol), 2-fluoro-4-(trifluoromethyl)phenylboronic acid (7.27 g, 33.2 mmol), [1,3-bis(2,6-diisopropylphenyl)imidazol-2-ylidene](3-chloropyridyl)palladium(II) dichloride (0.289 g, 0.416 mmol), potassium carbonate (4.87 g, 34.9 mmol). Degas with nitrogen, then add tert-amyl alcohol (50 mL) and water (10 mL). Heat to 70° C. for 3 h, then add additional 2-fluoro-4-(trifluoromethyl)phenylboronic acid (1.82 g, 8.32 mmol), [1,3-bis(2,6-diisopropylphenyl)imidazol-2-ylidene](3-chloropyridyl)palladium(II) dichloride (0.058 g, 0.083 mmol) and stir for 1 h. Cool to 22° C. then filter and wash with 1:5 water: tert-amyl alcohol then water. Dry under reduced pressure at 45° C. to give the title compound (4.26 g, 66.2% yield).

Preparation 5

(3-Chloro-7-methoxyquinolin-4-yl)(4-fluorophenyl)methanone

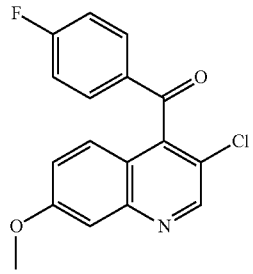 [SMILES: COc1ccc2c(C(=O)c3ccc(F)cc3)c(Cl)cnc2c1]

Scheme 1, Step D: Add isopropyl magnesium chloride 2.0 M in THF (239 m, 477 mmol) slowly to a stirred solution of 4-bromo-3-chloro-7-methoxyquinoline (100 g, 367 mmol) in THF (1.5 L) at −25° C., maintaining the temperature below −20° C. Stir at −25° C. for 1 h. Add 4-fluorobenzaldehyde (54.65 g, 440 mmol) slowly, maintaining the temperature below −5° C. Stir at −10° C. for 2 h. Add water (500 mL) and EtOAc (500 mL). Stir 30 min at 27.5° C. Add aqueous 1 M HCl solution (500 mL). Stir 30 min at 27.5° C. Separate the organic layer and wash with an aqueous 5% NaCl solution (500 mL) and an aqueous 5% NaHCO$_3$ solution (500 mL). Distill under reduced pressure below 50° C. until 4.5 mL/g remain. Add EtOAc (500 mL) and distill under reduced pressure below 50° C. until 5.5 mL/g remain. Add EtOAc (1200 mL). After 30 min at 27.5° C., add water (500 mL) and KBr (8.73 g, 0.073 mol), followed by TEMPO (2.81 g, 0.18 mol). After 30 min at 27.5° C., cool to −2.5° C. and add an aqueous solution of sodium hypochlorite, prepared by the mixing of sodium hypochlorite (500 mL, 74.44 mmol) with a solution of NaHCO$_3$(25.0 g in 500 mL of water). Stir the mixture for 1 h at −2.5° C., warm the solution to 27.5° C., Separate the organic layer and extract the aqueous layer with EtOAc (500 mL). Wash the combined organics with water (2×500 mL), treat with activated neutral charcoal (grade PF-33N, 5 g, 0.05 w/w) and filter through Hyflo bed. Distill under reduced pressure below 50° C. until 4.5 mL/g remain. Exchange solvent to EtOH by adding EtOH (500 mL) and distill until 4.5 mL/g remain (repeated co-distillation/concentration 1×). Heat to 75° C. and stir for 30 min. Cool to 12.5° C. slowly. Stir for 30 min, filter and wash the solids with EtOH (100 mL). Dry under reduced pressure at 42.5° C. to provide the title compound as a brown solid (78 g, 67.8% yield).

Alternative Preparation 5

(3-Chloro-7-methoxyquinolin-4-yl)(4-fluorophenyl)methanone

Scheme 2 Step C: Add isopropyl magnesium chloride 2.0 M in THF (119 mL, 0.238 mol) dropwise to a stirred solution of 4-bromo-3-chloro-7-methoxyquinoline (50 g, 0.183 mol) in THF (750 mL) at −25° C., maintaining the temperature below −15° C. Stir at −22.5° C. for 2 h. Add bis[2-(N,N-dimethylamino)ethyl] ether (35.28 g, 0.220 mol) and stir 30 min. Add 4-fluorobenzoyl chloride (34.8 g, 0.220 mol) slowly, maintaining the temperature below −5° C. Stir at −7.5° C. for 1 h. Filter through diatomaceous earth and wash with EtOAc (250 mL). Wash the combined filtrates with 1 M aqueous HCl (250 mL) followed by 5% aqueous NaCl (250 mL). Treat with activated neutral charcoal (grade PF-33N, 5 g, 0.05 w/w) and filter through diatomaceous earth. Distill under reduced pressure below 50° C. until 4.5 mL/g remain. Exchange solvent to EtOH by adding EtOH (500 mL) and distilling until 4.5 mL/g remain (repeated co-distillation/concentration 1×). Heat to 75° C. and stir for 30 min. Cool to 12.5° C. slowly and stir for 30 min, filter, and wash the solids with EtOH (100 mL). Dry under reduced pressure at 42.5° C. to provide the title compound as a brown solid (38 g, 66% yield).

Preparation 6

(3-Chloro-7-methoxy-4-quinolyl)-(2,3,5,6-tetradeuterio-4-fluoro-phenyl)methanone

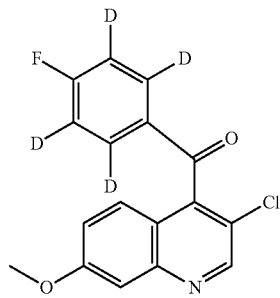 [SMILES: [2H]c1c([2H])c(C(=O)c2c(Cl)cnc3cc(OC)ccc23)c([2H])c([2H])c1F]

Add 2 M isopropylmagnesium chloride in THF (2.8 mL, 5.6 mmol) to a solution of 4-bromo-3-chloro-7-methoxyquinoline (0.74 g, 2.7 mmol) in THF (12 mL) at −40° C. and stir 1 h. Add a solution of 2,3,5,6-tetradeuterio-4-fluorobenzoyl chloride (0.97 g, 5.97 mmol) in THF (1.5 mL) and stir the mixture at −40° C. for 30 min and then warmed to RT for 30 min. Add a 2 to 1 mixture of water and saturated NH₄Cl (3 mL) to the reaction. Dilute the mixture with water (40 mL) and extract with DCM (3×20 mL). Combine the organic layers and wash with saturated brine (10 mL), dry over sodium sulfate and filter. Concentrate the filtrate onto silica gel (8 g) and purify by silica chromatography, eluting with a gradient of 10 to 30% EtOAc in hexanes to give the title compound (0.48 g, 55% yield) as a yellow solid. $^1$H NMR (400 MHz, DMSO-$d_6$) δ 8.98 (s, 1H), 7.57 (d, J=2.6 Hz, 1H), 7.40 (d, J=9.2 Hz, 1H), 7.31 (dd, J=9.2, 2.6 Hz, 1H), 3.95 (s, 3H).

Preparation 7 (3-Chloro-7-hydroxyquinolin-4-yl)(4-fluorophenyl)methanone

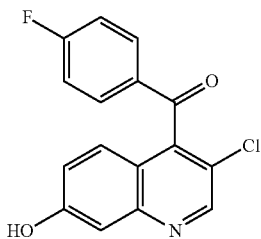 [SMILES: O=C(c1ccc(F)cc1)c1c(Cl)cnc2cc(O)ccc12]

Cleaving the methyl ether: Add 1 M BBr₃ in DCM (112.0 g, 0.45 mol) to a stirred solution of (3-chloro-7-methoxyquinolin-4-yl)(4-fluorophenyl)methanone (47.0 g, 0.15 mol) in DCM (494 mL) at 15° C. maintaining the temperature below 30° C. Warm to 35° C. and stir for 50-68 h. Quench the reaction with water (47 mL) and adjust the pH to 11-12 using 2 M NaOH (aq). Separate the layers and adjust the pH of the aqueous layer to 7-8 using 2 M HCl (aq) for precipitation of the product. Filter the solids and wash with water and DCM, then dry at reduced pressure to give the title compound (39.4 g, 85.4% yield).

Alternative Preparation 7

(3-Chloro-7-hydroxyquinolin-4-yl)(4-fluorophenyl)methanone

Cleaving the methyl ether: Add (3-chloro-7-methoxyquinolin-4-yl)(4-fluorophenyl)methanone (80 g, 0.25 mol), HBr 48% (800 mL) and acetic acid (400 mL). Stir at 30° C. for 30 min. Heat to 110° C. for 48 h. Cool to 90° C. and distill under reduced pressure below 100° C. until 7.5 mL/g remain. Cool to 5° C. and add water (800 mL) maintaining the temperature below 25° C. Stir for 2 h at 5° C., then filter and wash with water (80 mL). Treat the solids with NaHCO₃ (aq) (24 g, 0.30 w/w in 1200 mL, 15 mL/g water) for 30 min at 25° C. Filter and wash the solids with water (160 mL). Dry under reduced pressure at 60° C. to provide the title compound as a brown solid (72 g, 94.2% yield, 98.92% purity as determined by the following assay conditions: Shimadzu LC-20A HPLC system, Agilent Bonus RP column (75 mm*4.6 mm, 3.5 mm), column temperature 30° C., eluting with a gradient of 75% A (0.05% TFA in water)/25% B (0.05% TFA in AcCN) to 40% A/60% B over 20 min then 5% A/95% B over 2 min with a flow rate of 1.5 mL/min, UV 245 nm.)

Preparation 8

(3-Chloro-7-hydroxy-4-quinolyl)-(2,3,5,6-tetradeuterio-4-fluoro-phenyl)methanone

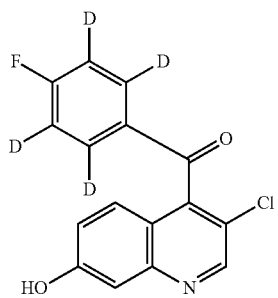 [SMILES: [2H]c1c([2H])c(C(=O)c2c(Cl)cnc3cc(O)ccc23)c([2H])c([2H])c1F]

Add 1 M boron tribromide in DCM (10 mL, 10 mmol, 3.3 equiv) to a solution of (3-chloro-7-methoxy-4-quinolyl)-(2,3,5,6-tetradeuterio-4-fluoro-phenyl)methanone (0.96 g, 3.0 mmol) in DCM (24 mL) and heat at 35° C. for 24 h. Add a second aliquot of 1 M boron tribromide in DCM (10 mL, 10 mmol) and heat at 35° C. for two days. Cool to RT, pour into saturated sodium bicarbonate (60 mL) and extract with DCM (2×60 mL). Dry the combined organic layers over sodium sulfate, filter, and concentrate onto silica gel. Purify by silica chromatography, eluting with a gradient of 0 to 8% MeOH in DCM to give the title compound (0.84 g, 92% yield) as a tan solid. $^1$H NMR (400 MHz, DMSO-$d_6$) δ 10.55 (s, 1H), 8.89 (s, 1H), 7.39 (d, J=2.4 Hz, 1H), 7.35 (d, J=9.0 Hz, 1H), 7.21 (dd, J=9.1, 2.5 Hz, 1H).

Preparation 9

(3-(2-Fluoro-4-(trifluoromethyl)phenyl)-7-hydroxyquinolin-4-yl)(4-fluorophenyl)methanone

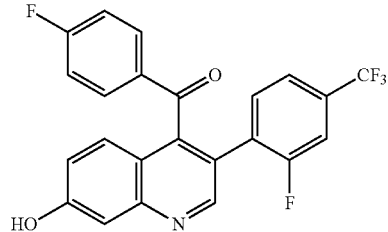 [SMILES: O=C(c1ccc(F)cc1)c1c(-c2ccc(C(F)(F)F)cc2F)cnc2cc(O)ccc12]

Scheme 3, Step A: Under a nitrogen atmosphere, combine (3-chloro-7-hydroxy-4-quinolyl)-(4-fluorophenyl)methanone (500.0 g, 1.66 mol), 2-fluoro 4-(trifluoromethyl) phenylboronic acid (447.9 g, 2.15 mol), NaHCO₃(210.0 g, 2.49 mol), THF (3 L), and water (750 mL). Degas the mixture with nitrogen, and add Pd-XPhos-G2 (13.0 g, 16.6 mmol), followed by heating the reaction mixture at 65° C. for 18.0 h. Cool the mixture to 20-30° C., filter through diatomite (~50 g), and rinse the filter cake with EtOAc (1.5 L). Separate the combined organic layer and concentrate while adding EtOAc (3×1.5 L) to give an EtOAc solution (2.5 L); wash with 7% aq. NaHCO₃(2 L) and 25% aq. NaCl (2 L). Treat the organic layer with silica thiol (50 g) at 55° C. for 2 h. Filter the mixture through diatomite (~50 g), wash with EtOAc (1.5 L), concentrate to 1.5 L, cool to 25° C., and add n-heptane (7.5 L) over 2 h. Cool the resulting mixture to 5° C., stir for 1 h, filter, wash with n-heptane (1.5 L), and dry at 45° C. for 18.0 h to provide the title compound as an off-white solid (660.0 g, 88.0% yield, 94.9% purity, as determined by the assay described in Alternative Preparation 7). $^1$H NMR (500 MHz, d$_6$-DMSO) δ 10.60 (s, 1H), 8.89 (d, J=1.3 Hz, 1H), 7.74-7.66 (m, 3H), 7.59-7.44 (m, 4H), 7.29-7.20 (m, 3H). $^{13}$C NMR (126 MHz, d$_6$-DMSO) δ 193.97, 165.61 (d, J=255.4 Hz), 159.66, 159.01 (d, J=247.8 Hz), 150.91, 149.34, 143.11, 133.40 (d, J=2.8 Hz), 132.78 (d, J=2.6 Hz), 132.33 (d, J=9.9 Hz), 130.91 (qd, J=33.1, 8.1 Hz), 128.39 (d, J=16.0 Hz), 126.62, 123.08 (qd, J=272.1, 2.4 Hz), 121.97, 121.35 (m), 121.10 (d, J=2.9 Hz), 117.63, 116.27 (d, J=22.3 Hz), 113.22 (dq, J=25.8, 3.8 Hz), 110.70.

Preparation 10

[3-[2-Fluoro-4-(trifluoromethyl)phenyl]-7-hydroxy-4-quinolyl]-(2,3,5,6-tetradeuterio-4-fluoro-phenyl)methanone

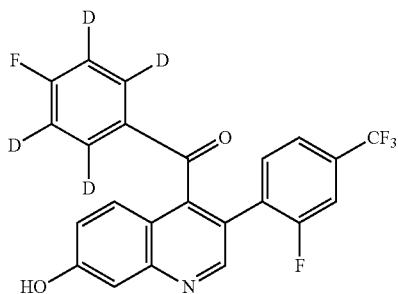 [SMILES: [2H]c1c([2H])c(C(=O)c2c(-c3ccc(C(F)(F)F)cc3F)cnc3cc(O)ccc23)c([2H])c([2H])c1F]

Vacuum degas and backfill with nitrogen (3×) a solution of (3-chloro-7-hydroxy-4-quinolyl)-(2,3,5,6-tetradeuterio-4-fluoro-phenyl)methanone (0.83 g, 2.6 mmol), [2-fluoro-4-(trifluoromethyl)phenyl]boronic acid (0.82 g, 3.9 mmol), XPhos Pd G2 (82 mg, 4 mol %), potassium carbonate (1.08 g, 7.8 mmol), water (5 mL) and tert-amyl alcohol (15 mL). Heat at 80° C. for 1 h, cool to RT, dilute with water (40 mL) and extract with EtOAc (2×40 mL). Combine the organic layers and wash with saturated brine (20 mL), dry over sodium sulfate, filter and concentrate under reduced pressure. Dissolve the residue in DCM and concentrated onto silica gel. Purify on silica gel chromatography, eluting with a gradient of 20 to 25% EtOAc in hexanes to give the title compound (0.96 g, 85% yield) as a solid. $^1$H NMR (400 MHz, DMSO-d$_6$) δ 10.59 (s, 1H), 7.71 (dd, J=10.0, 1.7 Hz, 1H), 7.61-7.49 (m, 2H), 7.49-7.41 (m, 2H), 7.23 (dd, J=9.1, 2.5 Hz, 1H), $^{19}$F NMR (376 MHz, DMSO-d$_6$) δ-61.30 (s), −103.61 (s), −111.80 (m).

Preparation 11

(3-Chloro-7-hydroxyquinolin-4-yl)(4-(2,2-diethoxy-ethoxy)phenyl)methanone

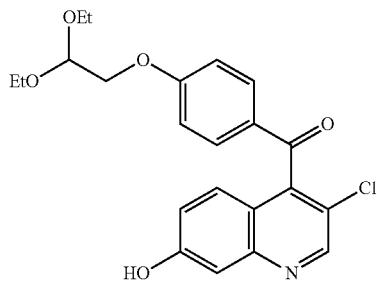 [SMILES: CCOC(COc1ccc(C(=O)c2c(Cl)cnc3cc(O)ccc23)cc1)OCC]

Scheme 5, Step A: Under a nitrogen atmosphere, add 20% potassium tert-butoxide in THF solution (92.98 g, 165.7 mmol) over 40 min to a solution of 2,2-diethoxyethanol (11.56 g, 86.2 mmol) and THF (60 mL) at 5° C. and stir for 0.5 h. Add to another reactor (3-chloro-7-hydroxy-4-quinolyl)-(4-fluorophenyl)methanone (20 g, 66.3 mmol) and THF (160 mL), and add the resulting solution to the potassium tert-butoxide/2,2-diethoxyethanol/THF mixture at 5° C. After 16.0 h, add aqueous 20% citric acid (60 mL) and aqueous 20% NaCl (60 mL) to the reaction, separate the organic phase and circulate through activated charcoal (1.5 g) at 25° C. for 0.5 h. Concentrate the organic phase while adding MTBE (3×100 mL) to give an MTBE (160 mL) solution, and wash with aqueous 20% NaCl (60 mL). Concentrate the resulting organic layer to 60 mL, heat to 40° C., and add n-heptane (80 mL) over 1 h. Stir the resulting slurry at 40° C. for 1 h, cool to 5° C. over 2 h, and stir for a further 16.0 h. Filter the solids, wash with n-heptane (40 mL), and dry at 45° C. to give the title compound as an off-white solid (21.0 g, 76.2% yield). $^1$H NMR (500 MHz, d$_6$-DMSO) δ 10.55 (s, 1H), 8.85 (s, 1H), 7.73 (d, J=8.5 Hz, 2H), 7.41 (d, J=2.5 Hz, 1H), 7.34 (d, J=9.0 Hz, 1H), 7.21 (dd, J=9.1, 2.5 Hz, 1H), 7.10 (d, J=8.6 Hz, 2H), 4.80 (t, J=5.1 Hz, 1H), 4.06 (d, J=5.2 Hz, 2H), 3.64 (dq, J=9.5, 7.0 Hz, 2H), 3.53 (dq, J=9.5, 7.0 Hz, 2H), 1.10 (t, J=7.1 Hz, 6H)

Alternate Preparation 11

(3-Chloro-7-hydroxyquinolin-4-yl)(4-(2,2-diethoxy-ethoxy)phenyl)methanone

Scheme 5, Step A: To the reactor, added (3-chloro-7-hydroxyquinolin-4-yl)(4-(2,2-diethoxyethoxy)phenyl)methanone (992.7 g, 2.39 mol), (2-fluoro-4-(trifluoromethyl)phenyl)boronic acid (650 g, 3.10 mol), NaHCO$_3$(304 g, 3.58 mol), THF (6.0 L), water (1.5 L). Degas the solution with nitrogen. Add PdXPHos G2 (14.40 g, 17.9 mmol). Stir at 65° C. for 16 h. Cool to 30° C. and add water (1.0 L). Filter through diatomaceous earth and wash with THF (3.0 L). Add water (2.0 L) and heptane (2.0 L). Separate the organic layer, treat with CUNO (activated carbon filter media), and crystallize with heptane to give the title product (1177 g, 89.54% yield, 98.54% purity as determined using the following HPLC conditions: Shimadzu LC-20A HPLC system, Agilent Bonus RP column (75 mm*4.6 mm; 3.5 mm), column temperature 30° C., eluting with a gradient of 75% A (0.05% TFA in water)/25% B (0.05% TFA in AcCN)

to 40% A/60% B over 20 and then to 5% A/95% B over 2 min with a flow rate of 1.5 mL/min, UV 245 nm).

Preparation 12

(4-(2,2-Diethoxyethoxy)phenyl)(3-(2-fluoro-4-(trifluoromethyl)phenyl)-7-hydroxyquinolin-4-yl)methanone

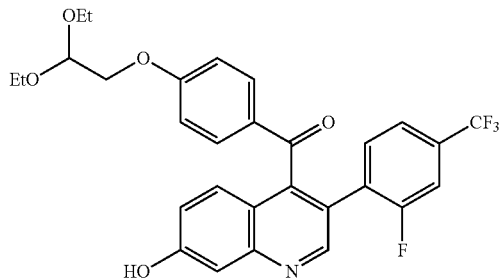 [SMILES: CCOC(COc1ccc(C(=O)c2c(-c3ccc(C(F)(F)F)cc3F)cnc3cc(O)ccc23)cc1)OCC]

Scheme 3, Step B: Under a nitrogen atmosphere, add 1 M potassium tert-butoxide in THF (291 mL, 0.29 mol) to a solution of 2,2-diethoxyethanol (20.3 g, 0.15 mol) in THF (150 mL) over 1.0 h at 5° C. In a separate reactor, dissolve (3-(2-fluoro-4-(trifluoromethyl)phenyl)-7-hydroxyquinolin-4-yl)(4-fluorophenyl)methanone (50.0 g, 0.12 mol) in THF (200 mL) and add the resulting solution to the potassium tert-butoxide/2,2-diethoxyethanol/THF mixture over 40 min at 5° C. After 16.0 h, add 20% citric acid (150 mL) to the reaction mixture, and wash the organic phase with 25% aq. NaCl (150 mL). Circulate the organic layer through activated charcoal (1.5 g) at 25° C. for 2.0 h, and then concentrate to remove THF while adding MTBE (2×250 mL) to give an MTBE solution with a final volume of 400 mL. Wash the MTBE solution with 20% brine (150 mL), concentrate to final volume of 150 mL, heat to 40° C., and add n-heptane (400 mL) over 2.0 h. Stir the resulting slurry at 40° C. for 1.0 h, cool to 5° C. over 3.0 h, and stir for 16.0 h. Filter the solids, wash with n-heptane (100 mL), and dry at 55° C. for 16.0 h to give the title compound as a yellow solid (51.1 g, 80.7% yield, 94.3% purity, as determined using the following HPLC conditions: Shimadzu LC-20A HPLC system, Agilent Bonus RP column (75 mm*4.6 mm; 3.5 mm), column temperature 30° C., eluting with a gradient of 65% A (0.05% TFA in water)/35% B (0.05% TFA in AcCN:MeOH=70:30 (v/v)) to 25% A/75% B over 20 and then to 5% A/95% B over 5 min with a flow rate of 1.5 mL/min, UV 245 nm. $^1$H NMR (500 MHz, d$_6$-DMSO) δ 10.65 (s, 1H), 8.89 (d, J=1.5 Hz, 1H), 7.73-7.67 (m, 1H), 7.61-7.49 (m, 4H), 7.49-7.42 (m, 2H), 7.22 (dd, J=9.1, 2.5 Hz, 1H), 7.01-6.96 (m, 2H), 4.77 (t, J=5.1 Hz, 1H), 4.01 (d, J=5.2 Hz, 2H), 3.64 (dq, J=9.6, 7.0 Hz, 2H), 3.52 (dq, J=9.6, 7.0 Hz, 2H), 1.09 (t, J=7.0 Hz, 6H). $^{13}$C NMR (126 MHz, d$_6$-DMSO) δ 193.48, 163.20, 159.70, 159.04 (d, J=248.5 Hz), 150.77, 149.02, 144.13, 133.38 (d, J=3.0 Hz), 131.71, 131.36-130.31 (m), 129.18, 128.50 (d, J=16.0 Hz), 126.78, 123.06 (qd, J=272.5, 2.3 Hz), 121.43-121.14 (m), 121.03, 120.92, 117.90, 114.97, 113.25 (dq, J=25.4, 3.6 Hz), 110.44, 99.65, 68.31, 62.02, 15.19. HRMS (ESI) m/z: [M+H]+ calcd for $C_{29}H_{26}F_4NO_5$: 544.1681, found 544.1669.

Alternate Preparation 12

(4-(2,2-Diethoxyethoxy)phenyl)(3-(2-fluoro-4-(trifluoromethyl)phenyl)-7-hydroxyquinolin-4-yl)methanone Scheme 5, Step B: Under a nitrogen atmosphere, combine (3-chloro-7-hydroxyquinolin-4-yl)(4-(2,2-diethoxyethoxy)phenyl)methanone (10.0 g, 24.1 mmol) with [2-fluoro-4-(trifluoromethyl)phenyl]boronic acid (6.5 g, 31.3 mmol), NaHCO$_3$ (3.0 g, 36.1 mmol), THF (60 mL), and water (15 mL). Degas the resulting mixture with nitrogen, add PdXPhos-G2 (0.2 g, 0.24 mmol), and heat to 65° C. for 16.0 h. Cool the mixture to 25° C., filter through diatomite (10 g) and rinse with EtOAc (30 mL). Concentrate the combined organic streams while adding EtOAc (3×50 mL) to give a 50 mL EtOAc solution, then wash with 7% aq. NaHCO$_3$ (30 mL) and 25% aq. NaCl (40 mL). Treat the organic layer with silica thiol (1 g, 5-10% w/w) at 60° C. for 16.0 h. Cool the mixture to 25° C., filter through diatomite (10 g) and rinse with EtOAc (30 mL). Combine the organic streams and concentrate while adding MTBE (2×50 mL) to provide a 30 mL MTBE solution. Add n-heptane (80 mL) at 40° C. over 0.5 h to form a slurry, cool to 5° C. and stir for 1.0 h. Filter the solids, wash with n-heptane (20 mL), and dry at 50° C. to give the title compound as an off-white solid (11.0 g, 84% yield).

Preparation 13

(R)-4-((4-(2,2-Diethoxyethoxy)phenyl)(hydroxy)methyl)-3-(2-fluoro-4-(trifluoromethyl)phenyl)quinolin-7-ol

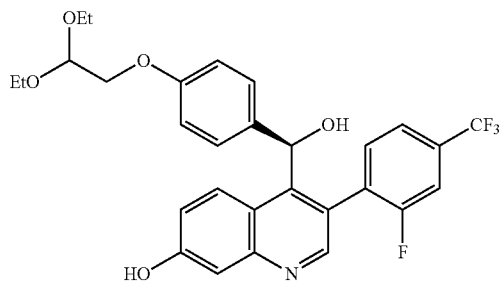 [SMILES: CCOC(COc1ccc([C@@H](O)c2c(-c3ccc(C(F)(F)F)cc3F)cnc3cc(O)ccc23)cc1)OCC]

Scheme 4, Step C: Under a nitrogen atmosphere, combine (4-(2,2-diethoxyethoxy)phenyl)(3-(2-fluoro-4-(trifluoromethyl)phenyl)-7-hydroxyquinolin-4-yl)methanone (100.0 g, 0.18 mol), diphenyl-[(2R)-pyrrolidin-2-yl]methanol (14.0 g, 55 mmol), trimethyl borate (6.7 g, 64.0 mmol) and THF (1.0 L). Stir the resulting mixture at 25° C. for 1.0 h. Add to the mixture 10 M BH$_3$-Me$_2$S solution (56.0 g, 0.74 mol), then warm to 45° C. for 2.0 h. After cooling to 25° C., add MeOH (100 mL) over 0.5 h, then add ethanolamine (23.5 g, 0.37 mol) and heat to 70° C. for 16.0 h. Concentrate the mixture to 500 mL, add MTBE (500 mL), and wash the mixture with 25% aq. NaCl (2×300 mL). Concentrate the organic layer under vacuum at 40° C. while adding THF (3×300 mL) to give a 1.0 L THF solution. Add MnO$_2$ (32.0 g, 0.36 mol) to the THF solution, and heat to 60° C. for 16.0 h. Remove the solids by filtration through diatomite (20 g) and rinse the cake with THF (500 mL). Circulate the combined organic solution through activated charcoal (1.5 g) for 2 h at 25° C. Concentrate the resulting solution under vacuum at 50° C.

while adding ACN (3×300 mL) to give the title compound as a ACN solution (332.5 g ACN solution containing 96.0 g of the title compound, 96% yield, 97.3% ee). Chiral analysis conditions: Agilent 1260 HPLC system, Chiralpak IG (250 mm*4.6 mm, 5 m), column temperature 45° C., eluting with 55% water and 45% ACN at 40° C. over 25 min with a flow rate of 1.0 mL/min, UV 230 nm, t(R) 16.2 min. NMR data collected at 100° C. to produce more coalesced resonances of atropisomers: $^1$H NMR (500 MHz, $d_6$-DMSO, 100° C.) δ 8.63 (s, 1H), 8.24 (d, J=9.3 Hz, 1H), 7.79-7.64 (m, 3H), 7.39-7.36 (m, 1H), 7.12 (d, J=8.4 Hz, 2H), 7.09-7.03 (m, 1H), 6.84 (d, J=8.7 Hz, 2H), 6.03 (s, 1H), 4.77 (t, J=5.1 Hz, 1H), 3.94 (dd, J=5.0, 1.6 Hz, 2H), 3.83-3.45 (m, 4H), 1.32-0.83 (m, 6H). $^{13}$C NMR (126 MHz, $d_6$-DMSO, 100° C.) δ 159.62 (d, J=247.3 Hz), 158.41, 157.30, 150.93, 150.62, 146.46, 136.15, 133.78, 130.81 (qd, J=33.1, 7.7 Hz), 130.36 (d, J=16.8 Hz), 128.96, 126.67, 123.58, 123.32 (qd, J=272.4, 2.7 Hz), 121.43-120.60 (m), 119.62, 118.80, 114.48, 113.03 (dd, J=26.0, 3.9 Hz), 110.84, 100.24, 70.30, 68.93, 61.93, 15.12. MS (ESI) m/z: [M+H]+ 546.2.

Alternate Preparation 13

(R)-4-((4-(2,2-Diethoxyethoxy)phenyl)(hydroxy)methyl)-3-(2-fluoro-4-(trifluoromethyl)phenyl)quinolin-7-ol Scheme 4, Step C: Add diphenyl-[(2R)-pyrrolidin-2-yl]methanol (47 mg, 0.186 mmol), THF (10 mL), trimethyl borate (1.26 mL, 11.1 mmol). Heat to 35° C. for 1 h. Cool to 25° C. and add borane N,N-diethylaniline (2.70 mL, 14.7 mmol). Add a solution of [4-(2,2-diethoxyethoxy)phenyl]-[3-[2-fluoro-4-(trifluoromethyl)phenyl]-7-hydroxy-4-quinolyl]methanone (2.00 g, 3.68 mmol) in THF (10 mL). Heat to 55° C. for 80 min. Cool to 0° C., then add MeOH (3.00 mL). Heat to 60° C. for decomplexation. Obtain the title compound in 98.22% ee. Chiral analysis conditions: Chiralpak IG (250 mm×4.6 mm, 5 m), column temperature 45° C., eluting with a gradient of 63% to 60% water in ACN over 55 min at 40° C. with a flow rate of 1.0 mL/min, UV 230 nm, $t_{(R)}$37.76 min.

Preparation 14

[3-[2-Fluoro-4-(trifluoromethyl)phenyl]-7-hydroxy-4-quinolyl]-[2,3,5,6-tetradeuterio-4-[2-[3-(fluoromethyl)azetidin-1-yl]ethoxy]phenyl]methanone

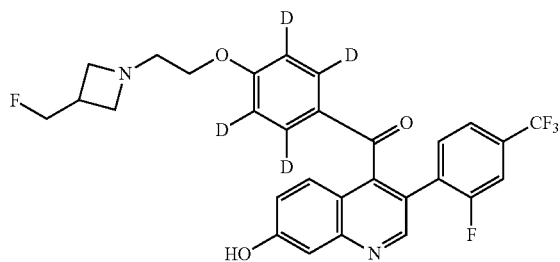 [SMILES: [2H]c1c([2H])c(C(=O)c2c(-c3ccc(C(F)(F)F)cc3F)cnc3cc(O)ccc23)c([2H])c([2H])c1OCCN1CC(CF)C1]

Add TEA (1.8 mL, 12.9 mmol) to a suspension of 2-[3-(fluoromethyl)azetidin-1-yl]ethanol. HCl (1.15 g, 6.7 mmol, 3.3 equiv) in MeOH (10 mL) and stir for 15 min then dilute with THF (20 mL). Concentrate the mixture under reduced pressure. Suspend the residue in THF (20 mL), filter, and wash the solids with THF (5 mL). Concentrate the filtrate under reduced pressure. Dilute the residue with THF (25 mL) and filter through a cellulose syringe filter. Treat the filtrate with potassium tert-butoxide (1.55 g, 13.8 mmol) and stir for 10 min. Add a solution of [3-[2-fluoro-4-(trifluoromethyl)phenyl]-7-hydroxy-4-quinolyl]-(2,3,5,6-tetradeuterio-4-fluoro-phenyl)methanone (0.88 g, 2.0 mmol) in THF (15 mL) and stir the mixture at RT overnight. Dilute the reaction with DCM (100 mL) and wash with a half saturated ammonium chloride (50 mL). Extract the aqueous wash with DCM (2×25 mL). Wash the combined organic layers with saturated brine (25 mL), dry over sodium sulfate, filter, and concentrate onto silica gel. Purify on silica gel, eluting with a gradient of 0 to 6% MeOH in DCM to give the title compound (0.66 g, 60% yield) as a yellow solid. $^1$H NMR (400 MHz, DMSO-$d_6$) δ 10.54 (s, 1H), 8.86 (d, J=1.6 Hz, 1H), 7.72 (dd, J=10.1, 1.7 Hz, 1H), 7.59-7.54 (m, 1H), 7.51 (t, J=7.6 Hz, 1H), 7.45-7.39 (m, 2H), 7.20 (dd, J=9.0, 2.6 Hz, 1H), 4.54 (d, J=6.2 Hz, 1H), 4.42 (d, J=6.2 Hz, 1H), 3.96 (t, J=5.5 Hz, 2H), 3.28 (dd, J=7.7, 1.5 Hz, 2H), 2.97 (dd, J=7.3, 5.9 Hz, 2H), 2.78-2.62 (m, 3H), $^{19}$F NMR (376 MHz, DMSO-$d_6$) δ 17.28 (m), −61.24(s), −111.93 (t, J=8.6 Hz).

Preparation 15

3-[2-Fluoro-4-(trifluoromethyl)phenyl]-4-[hydroxy-[2,3,5,6-tetradeuterio-4-[2-[3-(fluoromethyl)azetidin-1-yl]ethoxy]phenyl]methyl]quinolin-7-ol Add sodium borohydride (0.20 g, 5.2 mmol) to a solution of [3-[2-fluoro-4-(trifluoromethyl)phenyl]-7-hydroxy-4-quinolyl]-[2,3,5,6-tetradeuterio-4-[2-[3-(fluoromethyl)azetidin-1-yl]ethoxy]phenyl]methanone (0.28 g, 0.51 mmol) in a one to one mixture of THF and 2-propanol (24 mL). Add further sodium borohydride after 24 h (0.20 g, 5.2 mmol) and 72 h (0.20 g, 5.2 mmol). After six days dilute the reaction with 1 M HCl (20 mL) and DCM (50 mL), then stir for 10 min. Dilute the mixture with saturated sodium bicarbonate (50 mL). Separate the layers were separated and extract the aqueous layer with DCM (2×50 mL). Combine the organic layers and concentrate under reduced pressure. Dissolve the residue in MeOH (20 mL), add 12 M HCl (2 mL) and heat at 60° C. for 2 h. Cool the mixture, adjust the pH to basic with saturated sodium bicarbonate (50 mL) and extract with DCM (3×50 mL). Dry the combined organic layers over sodium sulfate, filter and concentrate onto silica gel. Purify on silica gel, eluting with a gradient of 3 to 8% MeOH in DCM to give the title compound (0.17 g, 63%) as a yellow solid.

Preparation 16

(R)-4-((4-(2,2-Diethoxyethoxy)phenyl)(hydroxy)methyl)-3-(2-fluoro-4-(trifluoromethyl)phenyl)quinolin-7-ol HCl

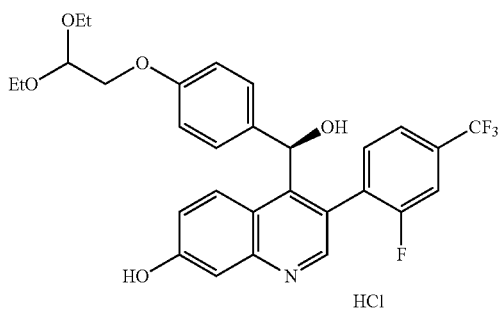 [SMILES: CCOC(COc1ccc([C@@H](O)c2c(-c3ccc(C(F)(F)F)cc3F)cnc3cc(O)ccc23)cc1)OCC ; Cl]

Dissolve (R)-4-((4-(2,2-diethoxyethoxy)phenyl)(hydroxy)methyl)-3-(2-fluoro-4-(trifluoromethyl)phenyl)quinolin-7-ol (236 mg, 43 mmol) in EtOAc (3 mL) with stirring at 500 rpm to give a yellow solution. Add HCl (500 µL, 1 M in EtOAc) to give a clear solution. Stir at 150 rpm for 30 min to give a thick slurry after 15 min. Filter and collect the off-white precipitate to give the title compound (230 mg, 91.4% yield).

X-Ray Powder Diffraction (XRPD) of Crystalline Forms

The XRPD patterns of crystalline solids are obtained on a Bruker D8 Endeavor X-ray powder diffractometer, equipped with a CuKα (1.5418A) source and a Linxeye detector, operating at 40 kV and 40 mA. The sample is scanned between 4 and 42 2θ°, with a step size of 0.009 2θ° and a scan rate of 0.5 seconds/step, and using 0.3° primary slit opening, and 3.9° PSD opening. The dry powder is packed on a quartz sample holder and a smooth surface is obtained using a glass slide. The crystal form diffraction patterns are collected at ambient temperature and relative humidity. Crystal peak positions are determined in MDI-Jade after whole pattern shifting based on an internal NIST 675 standard with peaks at 8.853 and 26.774 2θ°. It is well known in the crystallographic art that, for any given crystal form, the relative intensities of the diffraction peaks may vary due to preferred orientation resulting from factors such as crystal morphology and habit. Where the effects of preferred orientation are present, peak intensities are altered, but the characteristic peak positions of the polymorph are unchanged. See, e.g. The United States Pharmacopeia #23, National Formulary #18, pages 1843-1844, 1995. Furthermore, it is also well known in the crystallography art that for any given crystal form the angular peak positions may vary slightly. For example, peak positions can shift due to a variation in the temperature at which a sample is analyzed, sample displacement, or the presence or absence of an internal standard. In the present case, a peak position variability of ±0.2 2θ° is presumed to take into account these potential variations without hindering the unequivocal identification of the indicated crystal form. Confirmation of a crystal form may be made based on any unique combination of distinguishing peaks.

A prepared sample of (R)-4-((4-(2,2-diethoxyethoxy)phenyl)(hydroxy)methyl)-3-(2-fluoro-4-(trifluoromethyl)phenyl)quinolin-7-ol HCl form is characterized by an XRPD pattern using CuKα radiation as having diffraction peaks (2-theta values) as described in Table 1, and in particular having a peak at 5.6 in combination with one or more of the peaks selected from the group consisting of 11.1, 20.2, and 22.2.

TABLE 1

XRPD peaks of crystalline (R)-4-((4-(2,2-Diethoxyethoxy)phenyl)(hydroxy)methyl)-3-(2-fluoro-4-(trifluoromethyl)phenyl)quinolin-7-ol•HCl Form

| Peak | Angle (°2-Theta) +/− 0.2° | Relative Intensity (% of most intense peak) |
|---|---|---|
| 1 | 5.6 | 100.0% |
| 2 | 11.1 | 25.6% |
| 3 | 13.3 | 9.7% |
| 4 | 14.2 | 13.4% |
| 5 | 20.2 | 26.3% |
| 6 | 20.7 | 24.4% |
| 7 | 21.3 | 21.4% |
| 8 | 22.2 | 31.5% |
| 9 | 25.4 | 23.6% |
| 10 | 26.7 | 16.4% |

Preparation 17

(R)-5-4-(2,2-Diethoxyethoxy)phenyl)-8-(trifluoromethyl)-5H-[1]benzopyrano[4,3-c]quinolin-2-ol

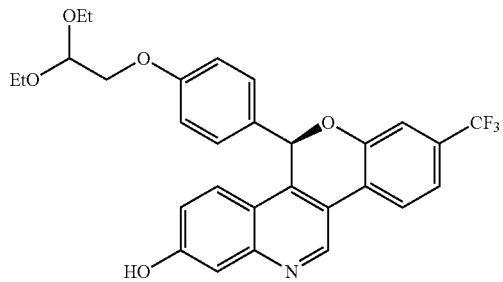 [SMILES: CCOC(COc1ccc([C@H]2Oc3cc(C(F)(F)F)ccc3-c3cnc4cc(O)ccc4c32)cc1)OCC]

Scheme 4, Step D: Under a nitrogen atmosphere, combine a ACN solution of (R)-4-((4-(2,2-diethoxyethoxy)phenyl)(hydroxy)methyl)-3-(2-fluoro-4-(trifluoromethyl)phenyl)quinolin-7-ol (332.5 g total weight=96.0 g of Preparation 13 compound; 94.6% ee; 176.0 mmol, about 400 mL) with Cs₂CO₃ (230.0 g, 706.0 mmol) and ACN (560 mL), and degas the resulting mixture with nitrogen. Stir the reaction mixture at 85° C. for 3 h and cool to 25° C., filter through diatomite (40 g), and rinse the cake through with ACN (300 mL). Combine the filtrate, rinse, and circulate through activated charcoal (1.5 g) for 2.0 h at 2θ° C. Concentrate the mixture and add 2-MeTHF (3×500 mL) during the concentration to give a 2-MeTHF solution (800 mL final volume). Wash with 1 M KHSO₄ (2×500 mL) and 10% aq. NaCl (300 mL). Concentrate the resulting organic layer to a final volume of 200 mL, and warm the resulting mixture to 40° C. Add n-heptane (100 mL) to the mixture dropwise and stir for 1 h, then add further n-heptane (1.4 L) slowly. Cool the resulting slurry to 5° C. over 3 h and stir for 18 h. Filter the solids and wash with n-heptane (300 mL), followed by drying under vacuum at 45° C. for 24.0 h to provide the title compound as a yellow solid (102.3 g, 95.2% ee; 86.6% yield, 78.3% w/w purity). Purity was determined using the following HPLC conditions: Shimadzu LC-20A HPLC system, Agilent Bonus RP column (75 mm*4.6 mm, 3.5 mM), column temperature 30° C., eluting with a gradient of 65% A (0.05% TFA in H2O)/35% B (0.05% TFA in MeOH) to 5% A/95% B over 30 min with a flow rate of 1.5 mL/min, UV 260 nm. Chiral analysis conditions: Shimadzu LC-20A HPLC system, Chiralpak IG (250 mm*4.6 mm, 5 m), column temperature 45° C., eluting with a gradient of 55-75% ACN in water over 23 min with a flow rate of 1.2 mL/min, UV 268 nm, to give the title compound, $t_{(R)}$ 15.9 min, $^1$H NMR (500 MHz, $d_6$-DMSO) δ 11.38 (s, 1H), 9.71 (s, 1H), 8.40 (d, J=8.1 Hz, 1H), 7.99 (d, J=9.3 Hz, 1H), 7.65 (d, J=2.3 Hz, 1H), 7.47-7.27 (m, 3H), 7.25 (d, J=1.8 Hz, 1H), 7.17-7.10 (m, 2H), 6.86-6.79 (m, 2H), 4.70 (t, J=5.2 Hz, 1H), 3.89-3.80 (m, 2H), 3.58 (dq, J=9.5, 7.0 Hz, 2H), 3.47 (dq, J=9.5, 7.0 Hz, 2H), 1.05 (td, J=7.0, 0.9 Hz, 6H). $^{13}$C NMR (126 MHz, $d_6$-DMSO) δ 161.88, 159.18, 151.76, 144.86, 143.32, 141.77, 130.92 (q, J=32.3 Hz), 129.83, 129.68, 126.75, 125.13 (d, J=2.7 Hz), 123.60, 122.56, 119.34, 118.79, 118.44, 115.21, 107.11, 100.21, 74.12, 68.38, 62.21, 15.63. HRMS (ESI) m/z: [M+H]+ Calcd for $C_{29}H_{27}F_3NO_5$ 526.1763; found 526.1777.

Alternate Preparation 17

(R)-5-4-(2,2-Diethoxyethoxy)phenyl)-8-(trifluoromethyl)-5H-[1]benzopyrano[4,3-c]quinolin-2-ol Combine (R)-4-((4-(2,2-diethoxyethoxy)phenyl)(hydroxy)methyl)-3-(2-fluoro-4-(trifluoromethyl)phenyl)quinolin-7-ol (2 g) and tert-amyl alcohol. Add sodium tert-pentoxide (0.85 g and maintain temperature at 20-30° C. for 19 h. Add further sodium tert-pentoxide (0.2 g) and stir at 20-30° C. for 4 h to give the crude title compound.

Alternate Preparation 17a (R)-5-4-(2,2-Diethoxyethoxy)phenyl)-8-(trifluoromethyl)-5H-[1]benzopyrano[4,3-c]quinolin-2-ol Bubble Nitrogen through a solution of (R)-4-((4-(2,2-diethoxyethoxy)phenyl)(hydroxy)methyl)-3-(2-fluoro-4-(trifluoromethyl)phenyl)quinolin-7-ol (18.4 g 34.8 mmol, 96.3% ee) and sodium tert-pentoxide (11.3 g, 102.6 mmol) in 2-MeTHF (100 mL) for about 30 min to 1 h at 25° C. Stir for 16 h at 25° C. Wash with NaHSO4 (1 M, 60 mL), followed by 7% NaHCO3 (60 mL), and then water (60 mL). Concentrate the solution to about 60 mL and crystallize the material by heptane addition. Filter the precipitated solid, wash with 2-MeTHF/heptane solution, and dry under vacuum to give the title compound (14.1 g, 77% yield, 95.6% ee). Chiral analysis conditions for the title compound and the starting material come from preparation 17 and preparation 13 respectively.

Preparation 18

(R)-2-(4-(2-Hydroxy-8-(trifluoromethyl)-5H-[1] benzopyrano[4,3-c]quinolin-5-yl)phenoxy)acetaldehyde and (R)-2-(4-(2-hydroxy-8-(trifluoromethyl)- 5H-chromeno[4,3-c]quinolin-5-yl)phenoxy)ethane-1, 1-diol

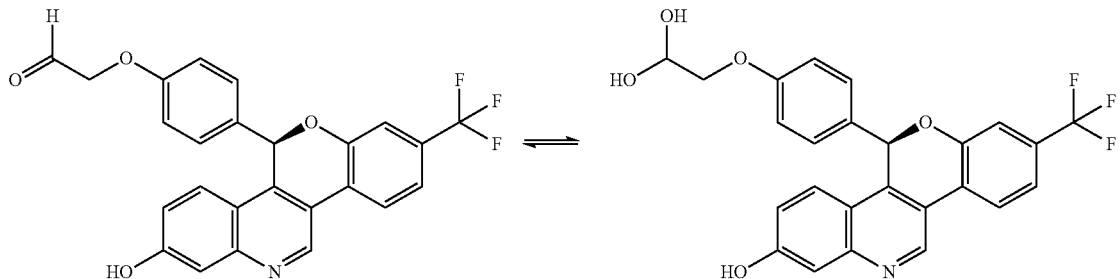 [SMILES: O=CCOc1ccc([C@H]2Oc3cc(C(F)(F)F)ccc3-c3cnc4cc(O)ccc4c32)cc1 ; Oc1ccc2c3c(cnc2c1)-c1ccc(C(F)(F)F)cc1O[C@@H]3c1ccc(OCC(O)O)cc1]

Scheme 4, Step E: It should be noted that the aldehyde form can be in equilibrium with the hydrated aldehyde form, as illustrated above.

Under a nitrogen atmosphere, combine (R)-5-4-(2,2-diethoxyethoxy)phenyl)-8-(trifluoromethyl)-5H-[1]benzopyrano[4,3-c]quinolin-2-ol (248.1 g, 80.6% purity=200.0 g; 92.4% ee; 381.0 mmol; purity analysis conditions are as described in Preparation 17) with ACN (1.0 L) and aqueous 1 N HCl (350 mL). Stir the resulting mixture at 60° C. for 2 h, cool to 25° C., and circulate through activated charcoal (1.5 g) for 1.0 h. Add a 7% aqueous solution of NaHCO3 (350 mL) over 1.0 h to adjust the pH to 3 while maintaining the temperature between 20 to 30° C. Concentrate the resulting mixture under vacuum to 1.4 L at 35 to 45° C. Add water (2 L) over 3.0 h and adjust the pH to 5.9 with 7% NaHCO3 (140 mL) at 25° C. Stir the mixture at 25° C. for 2 h, and then at 5° C. for 48 h. Filter the resulting solids, wash with water (400 mL), suspend the solids and add ACN (600 mL) at 45° C. for 2.0 h, then stir at 5° C. for 2.0 h. Filter the resulting solids, wash with ACN (400 mL), and dry under vacuum at 50° C. for 16 h to give the title compound as a yellow solid (157.8 g; 99.6% ee; 87.2% purity; 80.1% yield). Purity analysis conditions: Shimadzu LC-20A HPLC system, Waters Cortecs C18+ column (100 mm*4.6 mm; 2.7 mM), column temperature 45° C., eluting with a gradient of 80% A (0.1% TFA in H2O)/20% B (0.1% TFA in AcCN) to 30% A/70% B over 17 min then to 5% A/95% B over 2 min with a flow rate of 1.0 mL/min, UV 270 nM. Chiral analysis conditions: Agilent 1290 UPLC system, Chiralpak IG (250 mm*4.6 mm, 5 m), column temperature 45° C., eluting with a gradient of 25-55% ACN (0.1% TFA) in water (0.1% TFA) over 30 min with a flow rate of 0.3 mL/min, UV 270 nm, $t_{(R)}$ 24.2 min. Aldehyde form: (~50% mole in $d_6$-DMSO solution): $^1$H NMR (500 MHz, $d_6$-DMSO) δ 10.54 (s, 1H), 9.61 (s, 1H), 9.52 (s, 1H), 8.35 (d, J=7.7 Hz, 1H), 7.84 (dd, J=9.19, 7.00 Hz, 1H), 7.39 (m, 1H), 7.38 (m, 1H), 7.32 (d, J=5.62 Hz, 1H), 6.48 (dd, J=6.48, 1.81 Hz, 1H), 7.21 (dt, J=9.1, 2.5 Hz, 1H), 7.11 (d, J=8.9, 7.3 Hz, 2H), 6.81 (dd, J=8.8, 6.4 Hz, 2H), 4.78 (s, 2H). $^{13}$C NMR (126 MHz, $d_6$-DMSO) δ 198.76, 159.38, 157.97, 151.41, 149.09, 145.83, 136.80, 130.22, 129.80 (J 31.8 Hz), 129.19, 125.53, 124.24, 123.98, 123.7 (q, J=272.8 Hz), 120.52, 118.73 (m), 117.51, 117.13, 114.71, 114.6 (m), 110.70, 73.61, 72.40. HRMS (ESI) m/z: [M+H]*Calcd for $C_{25}H_{17}F_3NO_4$ 452.1031; found 452.1025. Hydrated Aldehyde form from $d_6$-DMSO: (~50% mole in $d_6$-DMSO solution): $^1$H NMR (500 MHz, $d_6$-DMSO) δ 10.54 (s, 1H), 9.52 (s, 1H), 8.35 (d, J=7.7 Hz, 1H), 7.84 (dd, J=9.19, 7.00 Hz, 1H), 7.39 (m, 1H), 7.38 (m, 1H), 7.32 (d, J=5.62 Hz, 1H), 6.48 (dd, J=6.48, 1.81 Hz, 1H), 7.21 (dt, J=9.1, 2.5 Hz, 1H), 7.11 (dd, J=8.9, 7.3 Hz, 2H), 6.81 (dd, J=8.8, 6.4 Hz, 2H), 6.03 (br, 1H), 5.00 (t, J=5.1 Hz, 1H), 3.70 (dd, J=5.1, 1.1 Hz, 2H). $^{13}$C NMR (126 MHz, $d_6$-DMSO) δ 159.38, 158.85, 151.43, 149.09, 145.83, 136.88, 130.22, 129.80 (J 31.8 Hz), 129.19, 125.53, 124.24, 123.98, 123.7 (q, J=272.8 Hz), 120.52, 118.73 (m), 117.51, 117.13, 114.71, 114.6 (m), 110.70, 87.97, 73.73, 71.58. HRMS (ESI) m/z: [M+H]*Calcd for $C_{25}H_{18}F3NO_5$ 469.40932; found 470.1288.

Alternate Preparation 18

(R)-2-(4-(2-Hydroxy-8-(trifluoromethyl)-5H-[1]benzopyrano[4,3-c]quinolin-5-yl)phenoxy)acetaldehyde Combine (R)-5-4-(2,2-diethoxyethoxy)phenyl)-8-(trifluoromethyl)-5H-[1]benzopyrano[4,3-c]quinolin-2-ol (0.99 g, 1.9 mmol) and formic acid (4 mL). Stir at RT overnight. Add over 5 min a solution of 28 mass % ammonium hydroxide (2 mL, 14 mmol) in water (15 mL). Filter the solution, wash with ACN (2 mL), and dry in a vacuum oven at 40° C. to give the title compound (0.79 g, 92% yield).

Alternate Preparation 18a (R)-2-(4-(2-Hydroxy-8-(trifluoromethyl)-5H-[1]benzopyrano[4,3-c]quinolin-5-yl)phenoxy)acetaldehyde Combine (R)-5-4-(2,2-diethoxyethoxy)phenyl)-8-(trifluoromethyl)-5H-[1]benzopyrano[4,3-c]quinolin-2-ol (5 g, 9.5 mmol), ACN (15 mL), water (10 mL), and TsOH. water (2.2 g, 11.4 mol). Heat the solution to 70° C. for 5 h, cool to RT. Adjust the pH to 5.0-5.5 with 7% NaHCO$_3$(aq, 3.4 mL) and stir at about 25° C. for 30 min with a precipitate forming in about 10 min. Filter the resulting precipitate, wash with water and dry under vacuum to give the title compound, (4.29 g, 98.2% purity, 99.7 ee, 87% yield). Purity analysis conditions for this product described in Preparation 18.

Preparation 18b

4-[(R)-(4-{2-[3-(Fluoromethyl)azetidin-1-yl]ethoxy}phenyl)(hydroxy)methyl]-3-[2-fluoro-4-(trifluoromethyl)phenyl]quinolin-7-ol

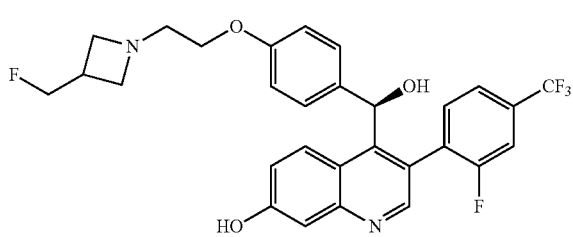 [SMILES: Oc1ccc2c([C@H](O)c3ccc(OCCN4CC(CF)C4)cc3)c(-c3ccc(C(F)(F)F)cc3F)cnc2c1]

Prepare the title compound as described in U.S. Pat. No. 10,654,866 for the racemic compound and purify the compound as described for Isomer 1 to give the title compound.

Preparation 19

(R)-5-(4-(2-(3-(Fluoromethyl)azetidin-1-yl)ethoxy)phenyl)-8-(trifluoromethyl)-5H-[1]benzopyrano[4,3-c]quinolin-2-ol

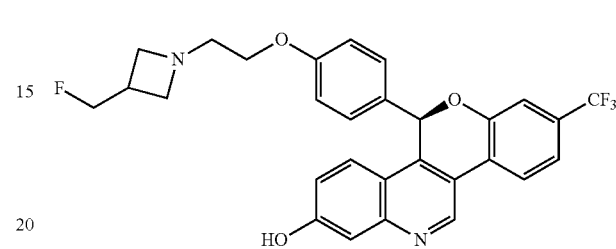

Scheme 4, Step F: Under a nitrogen atmosphere, combine 3-(fluoromethyl)azetidine tosylate (37.6 g, 143.9 mmol) with absolute EtOH (250 mL) and TEA (11.2 g, 110.7 mmol). Stir the resulting mixture at RT to give a clear solution. In a separate reactor, cool a mixture of (R)-2-(4-(2-hydroxy-8-(trifluoromethyl)-5H-[1]benzopyrano[4,3-c]quinolin-5-yl)phenoxy)acetaldehyde (57.5 g, 87% % purity, 110.8 mmol; purity analysis conditions described in Preparation 18) and absolute EtOH (250 mL) to 0-10° C. and add STAB (47.0 g, 221.5 mmol). Add the 3-(fluoromethyl)azetidine mixture, TEA, and EtOH solution to the (R)-2-(4-(2-hydroxy-8-(trifluoromethyl)-5H-[1]benzopyrano[4,3-c]quinolin-5-yl)phenoxy)acetaldehyde mixture, at 0-10° C. over 1 h and stir the mixture at 5-15° C. for 1 h. With continued stirring, add aqueous 10% NH$_4$Cl solution (250 mL) to the reaction mixture, followed by concentration to a final volume of about 375 mL. Add DCM (500 mL) to the resulting mixture and separate the organic phase. Wash the organic layer with 10% aq. Na$_2$CO$_3$ (250 mL) and 10% aq. NaCl (250 mL) and circulate through activated charcoal (1.5 g) for 30 min to give the title compound as a solution in DCM (500 mL) (58.7 g in DCM solution, 99.5% ee, 100% yield. Chiral analysis conditions: Shimadzu LC-20A HPLC system, Chiralpak IC (250 mm*4.6 mm, m), column temperature 40° C., eluting with 90% hexane (0.1% DEA)/10% EtOH over 30 min with a flow rate of 1.0 mL/min, UV 270 nm, $t_{(R)}$ 14.2 min.

Solid State NMR (R)-5-(4-(2-(3-(Fluoromethyl)azetidin-1-yl)ethoxy)phenyl)-8-(trifluoromethyl)-5H-[1]benzopyrano[4,3-c]quinolin-2-ol Solid state NMR is obtained on Bruker Avance III HD with a Bruker Ultrashield 400WB Plus magnet operating at a frequency of 100.6 MHz. The probe employed is a Bruker MAS 4 BL CP BB DVT N-P/H. Acquisitional parameters are as follows: 7776 scans, 34 ms acquisition time, 8.5 s interpulse delay, 10 kHz MAS frequency, 1.5 ms contact time, and a SPINAL64 decoupling scheme. The data are externally referenced to adamantane at 29.5 ppm. $^{13}$C Solid state NMR (101 MHz) δ 161.2, 159.0, 153.2, 151.3, 146.5, 135.1, 132.0, 130.8, 130.0, 125.2, 123.7, 122.6, 118.8, 117.9, 117.2, 114.7, 111.3, 84.9, 83.2, 74.8, 62.8, 57.8, 56.0, 53.3, 28.0.

Alternate Preparation 19

(R)-5-(4-(2-(3-(Fluoromethyl)azetidin-1-yl)ethoxy) phenyl)-8-(trifluoromethyl)-5H-[1]benzopyrano[4,3-c]quinolin-2-ol Prepare the title compound as described in U.S. Pat. No. 10,654,866 and separate the enantiomers to give isomer 2, which is the title compound of preparation 19.

Alternate Preparation 19a (R)-5-(4-(2-(3-(fluoromethyl)azetidin-1-yl)ethoxy) phenyl)-8-(trifluoromethyl)-5H-chromeno[4,3-c] quinolin-2-ol

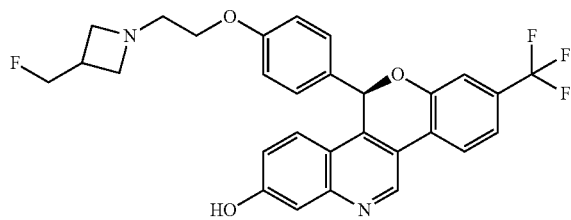 [SMILES: Oc1ccc2c3c(cnc2c1)-c1ccc(C(F)(F)F)cc1O[C@@H]3c1ccc(OCCN2CC(CF)C2)cc1]

A 100 mL flask was charged with (R)-2-(4-(2-hydroxy-8-(trifluoromethyl)-5H-chromeno[4,3-c]quinolin-5-yl)phenoxy)ethane-1,1-diol (10 g, 20.2 mmol). This intermediate is assumed to have 95% potency and contains 5 wt % water. A stir bar and THF (50 mL) were added to the flask and the flask was fitted with a septum and the reaction blanketed with nitrogen gas. Added water (135 mL) to adjust the water content to 10 wt %. The reaction was stirred at rt for 2 h to obtain a clear orange brown solution.

A separate 250 mL jacketed reactor equipped with mechanical stirring and a positive nitrogen atmosphere is charged with 3-(fluoromethyl)azetidine tosylate (5.6 g, 21.3 mmol), THF (48 mL), and triethylamine (1.4 mL). The jacket temperature is set to 0° C. and the reaction stirred for 30 min at 0° C. Sodium triacetoxyborohydride (8.15 g, 38.5 mmol) was added in one portion. The prepared THF solution of (R)-2-(4-(2-hydroxy-8-(trifluoromethyl)-5H-chromeno [4,3-c]quinolin-5-yl)phenoxy)ethane-1,1-diol was added to a syringe pump and added dropwise to the jacketed reactor over 2 h maintaining the reaction temperature at 0° C. After addition was complete, the reaction was allowed to stir an additional 2 h at 0° C. Reaction was analyzed for completion. If the amount of the 1,1-diol is <1% vs (R)-5-(4-(2-(3-(fluoromethyl)azetidin-1-yl)ethoxy)phenyl)-8-(trifluoromethyl)-5H-chromeno[4,3-c]quinolin-2-ol then the reaction was worked up. If the amount of the 1,1-diol is higher than 1%, the reaction was stirred another 2 to 8 h at 0° C. until complete.

The completed reaction was treated with 15% aqueous KHCO₃ (57 mL) over >10 min at 0° C. The jacket temperature on the reaction was raised to 20° C. to 30° C. and the reaction stirred for >2 h. Stirring was stopped and the reaction allowed to settle for >1 h. The aqueous layer was drained and the reaction charged again with 15% aqueous KHCO₃ (57 mL). The jacket temperature was raised to 40° C. to 50° C. and the reaction stirred at that temperature for 2 h. Stirring was stopped and the reaction allowed to settle at 20° C. to 30° C. Reaction was analyzed for completion. If the tosylate peak was >1% vs (R)-5-(4-(2-(3-(fluoromethyl)azetidin-1-yl)ethoxy)phenyl)-8-(trifluoromethyl)-5H-chromeno[4,3-c]quinolin-2-ol, washes with 15% aqueous KHCO₃ were continued as described until the tosylate peak is <1%.

The aqueous layer was drained and the reaction treated with heptane (4.5 mL) and water (38 mL). The reaction was stirred at 20° C. to 30° C. for >30 min and stirring stopped and the reaction allowed to stand for >1 h and the aqueous layer drained.

The reaction was concentrated at a bath temperature below 70° C. under a slight vacuum (−0.05 MPa target) to between 60 mL and 100 mL total volume. THF (95 mL) was added and the reaction concentrated at a bath temperature below 70° C. under slight vacuum (−0.05 MPa target) to between 30 mL and 50 mL total volume. If the reaction contained more than 1% water by KF analysis, the distillation steps above were repeated.

The solvent volume of the reaction was adjusted to 60 mL with THF and stirred at 40° C. for 1 h. MeCN was added via syringe pump over 1 h at 40° C. and then the reaction was seeded with (R)-5-(4-(2-(3-(fluoromethyl)azetidin-1-yl) ethoxy)phenyl)-8-(trifluoromethyl)-5H-chromeno[4,3-c] quinolin-2-ol (70 mg) and the reaction allowed to stir at 40° C. for 4 h. Added MeCN (38 mL) via syringe pump over 2 h and stirred an additional 2 h at 40° C. Added MeCN (57 mL) via syringe pump over 3 h and stirred an additional 1 h at 40° C. Adjusted the temperature to 0° C. to 10° C. over 3 h and stirred an additional 2 h at 0° C. Removed the solid by filtration and rinsed with MeCN/THF (29 mL of a 2:1 solution). The solid was dried in the vacuum at 30° C. for 5 h and at 45° C. for 11 h to give the title compound (7.7 g, 70%).

Preparation 20

5-[2,3,5,6-tetradeuterio-4-[2-[3-(fluoromethyl)azetidin-1-yl]ethoxy]phenyl]-8-(trifluoromethyl)-5H-chromeno[4,3-c]quinolin-2-ol

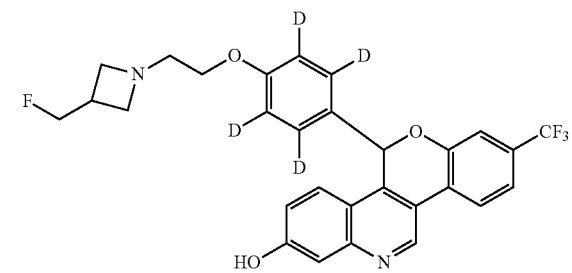 [SMILES: [2H]c1c([2H])c(C2Oc3cc(C(F)(F)F)ccc3-c3cnc4cc(O)ccc4c32)c([2H])c([2H])c1OCCN1CC(CF)C1]

Add a 60% dispersion of NaH in mineral oil (0.10 g, 2.5 mmol) to a solution of 3-[2-fluoro-4-(trifluoromethyl)phenyl]-4-[hydroxy-[2,3,5,6-tetradeuterio-4-[2-[3-(fluoromethyl)azetidin-1-yl]ethoxy]phenyl]methyl]quinolin-7-ol (0.17 g, 0.31 mmol) in THF (12 mL) and heat at 50-60° C. overnight. Cool the reaction to RT and sequentially dilute with saturated ammonium chloride (10 mL) and saturated sodium bicarbonate (20 mL). Extract the mixture with DCM (2×50 mL) and wash the combined organic layers with saturated brine (10 mL), dry over sodium sulfate and concentrate onto silica gel. Purify on silica gel, eluting with a gradient of 3 to 8% MeOH in DCM to give the title compound (0.09 g, 55%) as a yellow solid. Two batches prepared essentially the same were combined in MeOH and DCM and dried under vacuum overnight to give the final material. $^1$H NMR (400 MHz, DMSO-d$_6$) δ 10.41 (s, 1H), 9.49 (s, 1H), 8.46-8.26 (m, 1H), 7.81 (d, J=9.2 Hz, 1H), 7.39 (ddd, J=8.1, 1.9, 0.8 Hz, 1H), 7.34 (d, J=2.5 Hz, 1H), 7.30 (s, 1H), 7.23 (d, J=1.9 Hz, 1H), 7.17 (dd, J=9.1, 2.5 Hz, 1H), 4.51 (d, J=6.2 Hz, 1H), 4.40 (d, J=6.3 Hz, 1H), 3.84-3.75 (m, 2H), 3.25 (td, J=7.6, 1.5 Hz, 2H), 2.97-2.88 (m, 2H), 2.75-2.57 (m, 3H). $^{19}$F NMR (376 MHz, DMSO-d$_6$) δ 17.40 (td, J=47.6, 46.8, 18.1 Hz), −61.16 (s). $^{13}$C NMR (101 MHz, DMSO) δ 159.62, 151.93, 150.03, 146.57, 136.91, 129.85, 125.94, 124.85, 124.39, 120.78, 117.89, 117.49, 111.54, 85.90, 84.28, 74.12, 66.70, 57.61, 56.50, 56.42, 40.66, 40.45, 40.24, 40.03, 39.82, 39.61, 39.40, 31.25, 31.06.

Example 1

(R)-5-(4-(2-(3-(Fluoromethyl)azetidin-1-yl)ethoxy)phenyl)-8-(trifluoromethyl)-5H-[1]benzopyrano[4,3-c]quinolin-2-ol, 4-methylbenzenesulfonic acid

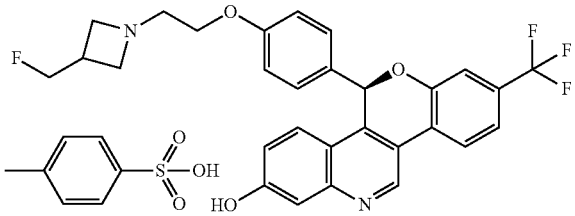

Combine (R)-5-(4-(2-(3-(fluoromethyl)azetidin-1-yl)ethoxy)phenyl)-8-(trifluoromethyl)-5H-[1]benzopyrano[4,3-c]quinolin-2-ol (100 mg, 0.19 mmol) in MeOH (2 mL) and heat to 50° C. to give a dark yellow solution. Dissolve 4-methylbenzenesulfonic acid (0.39 mg, 0.58 mmol) in MeOH (1 mL). Combine the 2 solutions and remove the heat source. Stir the mixture overnight at RT. Filter the resulting precipitate, wash with MeOH (1 mL) and air dry over vacuum for 20 min to give the title compound (0.81 g, 61%).

Alternate Example 1

(R)-5-(4-(2-(3-(Fluoromethyl)azetidin-1-yl)ethoxy)phenyl)-8-(trifluoromethyl)-5H-[1]benzopyrano[4,3-c]quinolin-2-ol, 4-methylbenzenesulfonic acid Scheme 4, Step F: Add 3-(fluoromethyl)azetidine tosylate (0.79 g, 0.300 mmol) and IPA (5 mL) and stir the mixture. Add pyridine borane (200 μL, 2.0 mmol) to the mixture. In a separate vessel, add (R)-2-(4-(2-hydroxy-8-(trifluoromethyl)-5H-[1]benzopyrano[4,3-c]quinolin-5-yl)phenoxy)acetaldehyde (1.00 g, 2.21 mmol) in DMSO (2.5 mL) and add dropwise to the tosylate mixture over about 5 min. Stir for 3 h. Add IPA (15 mL) dropwise. Filter the resulting solid, wash the wet cake with IPA (2×5 mL) and dry the solid in a vacuum oven to give the title compound (1.09 g, 68% yield). Complete essentially the same procedure using DMAC as the solvent to give the title compound (1.06 g, 66% yield)

Alternate Example 1a (R)-5-(4-(2-(3-(Fluoromethyl)azetidin-1-yl)ethoxy)phenyl)-8-(trifluoromethyl)-5H-[1]benzopyrano[4,3-c]quinolin-2-ol, 4-methylbenzenesulfonic acid Scheme 4, Step F: Combine pyridinium p-tosylate (0.5021 g, 2.0 mmol), sodium borohydride (76.0 mg, 2.01 mmol) and THF (10 mL). Stir for 3 h and filter through diatomaceous earth. Add 3-(fluoromethyl)azetidine tosylate (766.1 mg, 2.9 mmol) in tert-amyl alcohol (15 mL) and stir the mixture for 1 h. Add a solution (R)-2-(4-(2-hydroxy-8-(trifluoromethyl)-5H-[1]benzopyrano[4,3-c]quinolin-5-yl)phenoxy)acetaldehyde (1.01 g, 2.2 mmol) in THF (5 mL) over 2 h via syringe pump and stir the mixture overnight. Filter the mixture, wash the wet cake with IPA (1.5 mL), and dry in a 40° C. vacuum oven to give the title compound (1.16 g, 68% yield). $^1$H NMR (600 MHz, ACN-d$_3$/D20, 25° C.) δ 9.31 (s, 1H), 8.10 (d, J=8.1 Hz, 1H), 7.65 (d, J=9.1 Hz, 1H), 7.61-7.57 (m, 2H), 7.39 (d, J=2.5 Hz, 1H), 7.33 (dd, J=8.2, 1.8 Hz, 1H), 7.19-7.12 (m, 4H), 7.12-7.08 (m, 2H), 7.07 (s, 1H), 6.77-6.72 (m, 2H), 4.48 (dd, J=47.0, 3.8 Hz, 2H), 4.26-4.19 (m, 2H), 4.05-3.99 (m, 4H), 3.44 (m, 2H), 3.22-3.04 (m, 1H), 2.29 (s, 3H).

Alternate Example 1b (R)-5-(4-(2-(3-(Fluoromethyl)azetidin-1-yl)ethoxy)phenyl)-8-(trifluoromethyl)-5H-[1]benzopyrano[4,3-c]quinolin-2-ol, 4-methylbenzenesulfonic acid Scheme 4, Step F: Combine (R)-2-(4-(2-hydroxy-8-(trifluoromethyl)-5H-[1]benzopyrano[4,3-c]quinolin-5-yl)phenoxy)acetaldehyde (2.0 g, 4.3 mmol) and THF (20 mL). Stir for 30 min. In a separate vessel, combine sodium triacetoxy borohydride (2.0 g, 9.5 mmol), THF (20 mL), and 3-(fluoromethyl)azetidine tosylate (1.2 g, 2.3 mmol). Add the THF solution of (R)-2-(4-(2-hydroxy-8-(trifluoromethyl)-5H-[1]benzopyrano[4,3-c]quinolin-5-yl)phenoxy)acetaldehyde dropwise over 1 h. Stir an additional 1 h. Quench with 10% aq. KHSO$_4$ (10 mL) and stir 30 min. Filter and wash the organic layer with 10% aq. NaHCO$_3$ (10 mL) and saturated NaCl. Concentrate the organic layer, crystallize the residue from THF/ACN, filter the precipitated solid, and dry the solid in a vacuum oven to give the title compound (1.02 g, 41% yield).

Solid State NMR, Example 1b

Solid State NMR is acquired as in Preparation 19 with 7.5 s interpulse delay, $^{13}$C Solid state NMR (101 MHz) δ 162.0, 158.6, 152.2, 148.9, 143.6, 143.1, 141.7, 139.0, 138.5, 131.1, 129.1, 128.1, 126.9, 125.3, 123.3, 121.8, 121.0, 118.6, 117.9, 116.9, 116.2, 110.1, 108.4, 84.2, 82.6, 81.1, 72.2, 61.4, 57.4, 55.6, 54.8, 30.9, 29.0, 20.9.

Example 2

(R)-5-(4-(2-(3-(Fluoromethyl)azetidin-1-yl)ethoxy)phenyl)-8-(trifluoromethyl)-5H-[1]benzopyrano[4,3-c]quinolin-2-ol, benzene sulfonic acid

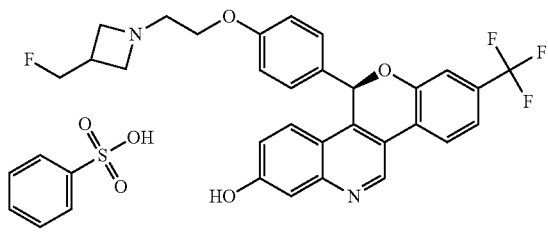 [SMILES: O=S(=O)(O)c1ccccc1 ; Oc1ccc2c3c(cnc2c1)-c1ccc(C(F)(F)F)cc1O[C@@H]3c1ccc(OCCN2CC(CF)C2)cc1]

Combine (R)-5-(4-(2-(3-(fluoromethyl)azetidin-1-yl)ethoxy)phenyl)-8-(trifluoromethyl)-5H-[1]benzopyrano[4,3-c]quinolin-2-ol (293 mg, 0.56 mmol) in ACN (6 mL) and water (0.3 mL) heat to 50° C. with stirring to give a yellow solution. Dissolve benzenesulfonic acid (0.108 mg, 0.68 mmol) in ACN (1 mL) and add to the (R)-5-(4-(2-(3-(fluoromethyl)azetidin-1-yl)ethoxy)phenyl)-8-(trifluoromethyl)-5H-[1]benzopyrano[4,3-c]quinolin-2-ol solution to give a bright yellow solution. Allow to stir at 50° C. for 2 h and then cool to RT. Filter the resulting precipitate over vacuum and allow to air dry without vacuum over weekend to give the title compound (0.157 g, 41%). Solid State NMR is acquired as in Preparation 19 with 8.0 s interpulse delay, $^{13}C$ Solid state NMR (101 MHz) δ 161.9, 159.1, 158.4, 151.8, 149.1, 146.8, 146.4, 142.8, 138.0, 131.5, 130.4, 129.7, 128.2, 127.5, 126.6, 125.1, 122.9, 122.3, 121.5, 120.8, 118.5, 117.8, 117.0, 116.3, 110.4, 109.2, 108.5, 84.2, 83.0, 82.5, 81.4, 71.9, 65.0, 64.3, 62.0, 61.7, 61.0, 60.4, 60.0, 58.2, 57.9, 57.2, 56.8, 56.4, 55.2, 54.5, 54.0, 53.6, 52.6, 31.6, 31.0, 30.3, 29.6.

Example 3

(5R)-5-[4-(2-Hydroxyethoxy)phenyl]-8-(trifluoromethyl)-5H-chromeno[4,3-c]quinolin-2-ol

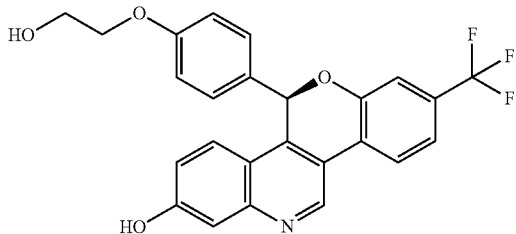 [SMILES: OCCOc1ccc([C@H]2Oc3cc(C(F)(F)F)ccc3-c3cnc4cc(O)ccc4c32)cc1]

The final bond forming step, i.e., the reductive amination, in the synthesis of (R)-5-(4-(2-(3-(fluoromethyl)azetidin-1-yl)ethoxy)phenyl)-8-(trifluoromethyl)-5H-[1]benzopyrano[4,3-c]quinolin-2-ol, 4-methylbenzenesulfonic acid is key for controlling the purity of the final compound. The most important aspect is that the use of triethylamine in the reductive amination limits the formation of (5R)-5-[4-(2-hydroxyethoxy)phenyl]-8-(trifluoromethyl)-5H-chromeno[4,3-c]quinolin-2-ol to 0.3% or below, as measured by HPLC. $^1$H NMR (500 MHz, DMF-d7Rt, 25° C.) δ 10.72 (s, 1H), 9.61 (s, 1H), 8.49-8.44 (m, 1H), 7.95 (d, J=9.1 Hz, 1H), 7.50 (d, J=2.5 Hz, 1H), 7.46 (m, 1H), 7.38 (s, 1H), 7.32-7.26 (m, 2H), 7.23 (d, J=8.8 Hz, 2H), 6.87 (d, J=8.8 Hz, 2H), 4.89 (t, J=5.7 Hz, 1H), 3.99 (dd, J=5.4, 4.6 Hz, 2H), 3.78 (td, J=5.7, 4.5 Hz, 2H). MS ES+m/z 454 [M+H]*. Purity analysis conditions: Agilent 1260 HPLC system, Waters Cortecs $C_{18}$+ column (100 mm×4.6 mm, 2.7 mm), column temperature 45° C., eluting with a gradient of 75% A (0.1% TFA in water:ACN:MeOH=90:2:8, v/v/v)/25% B (ACN:MeOH=20:80, v/v) to 10% A/90% B over 30 min with a flow rate of 0.8 mL/min, UV 270 nm. Rt=14.661 min.

Example 4

3-(Chloromethyl)azetidine, 4-methylbenzenesulfonic acid

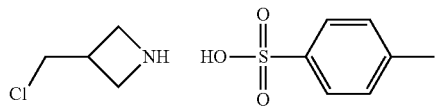

3-(Chloromethyl)azetidine 4-methylbenzenesulfonic acid is an impurity that may be present in 3-(fluoromethyl)azetidine 4-methylbenzenesulfonic acid. When present, it is typically between 0.05% and 0.5% as determined using HPLC. $^1$H NMR (500 MHz, DMSO) δ 8.71 (s, 2H), 7.57 (d, J=8.1 Hz, 2H, counterion), 7.16 (d, J=8.1 Hz, 2H, counterion), 4.05 (dd, 2H), 3.84 (d, J=6.8 Hz, 2H), 3.81 (dd, 2H), 3.18 (m, 1H), 2.33 (s, 3H, counterion).

Example 5

(5R)-5-[4-[2-[3-(Chloromethyl)azetidin-1-yl]ethoxy]phenyl]-8-(trifluoromethyl)-5H-chromeno[4,3-c]quinolin-2-ol

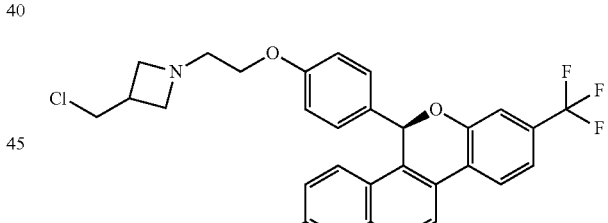

If 3-(chloromethyl)azetidine 4-methylbenzenesulfonic acid is present during the synthesis of imlunestrant, then the title compound above may be formed. This compound may be present at levels from 0.05% to 0.5%. MS ES+m/z 541 [M+H]+. $^1$H NMR (500 MHz, DMSO-$d_6$) δ 10.50 (s, 1H), 9.50 (s, 1H), 8.34 (d, J=8.1 Hz, 1H), 7.81 (d, J=9.2 Hz, 1H), 7.37 (dd, J=8.1, 1.6 Hz, 1H), 7.37 (d, J=2.5 Hz, 1H), 7.28 (s, 1H), 7.21 (d, J=1.6 Hz, 1H), 7.18 (dd, J=9.2, 2.5 Hz, 1H), 7.09 (d, 8.8 Hz, 2H), 6.76 (d, 8.8 Hz, 2H), 3.79 (m, 2H), 3.71 (d, J=7.5 Hz, 2H), 3.26 (dd, J=7.3 Hz, 2H), 2.88 (dd, J=7.4, 6.2 Hz, 2H), 2.63 (dd, J=7, 4, 5.7 Hz, 2H), 2.63 (m, 1H). Purity analysis conditions: Agilent 1260 HPLC system, Waters Cortecs C18+ column (100 mm×4.6 mm, 2.7 mm), column temperature 45° C., eluting with a gradient of 75% A (0.1% TFA in water:ACN:MeOH=90:2:8, v/v/v)/25% B (ACN:MeOH=20:80, v/v) to 10% A/90% B over 30 min with a flow rate of 0.8 mL/min, UV 270 nm.

Example 6

(5R)-5-[4-[2-[[2-(Chloromethyl)-3-fluoro-propyl]amino]ethoxy]phenyl]-8-(trifluoromethyl)-5H-chromeno[4,3-c]quinolin-2-ol

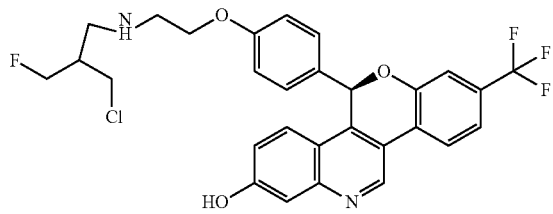 [SMILES: Oc1ccc2c3c(cnc2c1)-c1ccc(C(F)(F)F)cc1O[C@@H]3c1ccc(OCCNCC(CF)CCl)cc1]

The compound above was present as an impurity found in samples of (R)-5-(4-(2-(3-(fluoromethyl)azetidin-1-yl)ethoxy)phenyl)-8-(trifluoromethyl)-5H-[1]benzopyrano[4,3-c]quinolin-2-ol, 4-methylbenzenesulfonic acid. It is believed that this compound is formed when any free chloride ions that are present react with the cyclobutyl group. MS ES+m/z 561 [M+H]+. $^1$H NMR (500 MHz, DMSO-$d_6$) δ 10.43 (s, 1H), 9.50 (s, 1H), 8.36 (d, J=8.2 Hz, 1H), 7.82 (d, J=9.2 Hz, 1H), 7.40 (dd, J=8.2, 2.1 Hz, 1H), 7.36 (d, J=2.5 Hz, 1H), 7.31 (s, 1H), 7.24 (d, J=2.1 Hz, 1H), 7.18 (dd, J=9.2, 2.5 Hz, 1H), 7.10 (d, 8.8 Hz, 2H), 6.82 (d, 8.8 Hz, 2H), 4.49 (m, 2H), 3.91 (m, 2H), 3.70 (m, 2H), 2.82 (dd, J=11.2 Hz, 2H), 2.61 (d, J=6.7 Hz, 2H), 2.18 (m, 1H)

Example 7

(5R)-5-[4-[2-[3-[[1-[2-[4-[(5R)-2-Hydroxy-8-(trifluoromethyl)-5H-chromeno[4,3-c]quinolin-5-yl]phenoxy]ethyl]azetidin-3-yl]methoxymethyl]azetidin-1-yl]ethoxy]phenyl]-8-(trifluoromethyl)-5H-chromeno[4,3-c]quinolin-2-ol

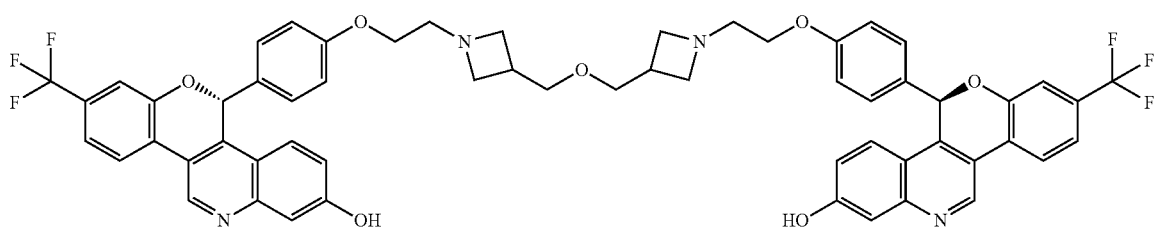 [SMILES: Oc1ccc2c3c(cnc2c1)-c1ccc(C(F)(F)F)cc1O[C@@H]3c1ccc(OCCN2CC(COCC3CN(CCOc4ccc([C@H]5Oc6cc(C(F)(F)F)ccc6-c6cnc7cc(O)ccc7c65)cc4)C3)C2)cc1]

Example 8

(5R)-13-(Fluoromethyl)-5-(4-(2-(3-(fluoromethyl)azetidin-1-yl)ethoxy)phenyl)-11-(2-(4-((R)-2-hydroxy-8-(trifluoromethyl)-5H-chromeno[4,3-c]quinolin-5-yl)phenoxy)ethyl)-8-(trifluoromethyl)-5,10c,11,12,13,14-hexahydrochromeno[4,3-c]pyrimido[1,2-a]quinolin-2-ol

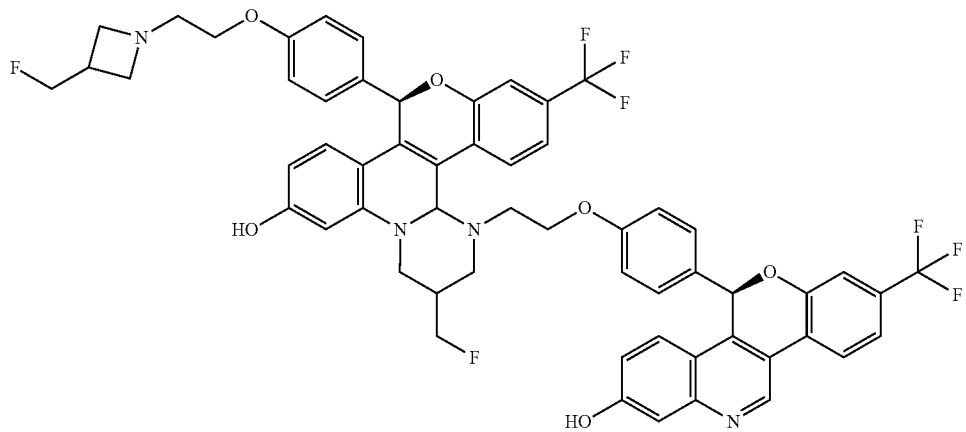 [SMILES: Oc1ccc2c(c1)N1CC(CF)CN(CCOc3ccc([C@H]4Oc5cc(C(F)(F)F)ccc5-c5cnc6cc(O)ccc6c54)cc3)C1C1=C2[C@@H](c2ccc(OCCN3CC(CF)C3)cc2)Oc2cc(C(F)(F)F)ccc21]

MS ES+m/z 1050 [M+H]+.

Chromatographic Methods

Compare compounds of Preparation 18b, Preparation 19, and Alternate Preparation 19 using two different chromatography protocols: HPLC Method 1 and HPLC Method 2, which are described below.

HPLC Method 1 utilizes the following conditions: Agilent 1260 HPLC system with UV detector at 245 nm with an Agilent Bonus RP 4.6×75 mm, 3.5 µm column with a column temperature of 30° C. with a flow rate of 1.0 mL/min and injector volume of 5 µl. Mobile phase A consists of 0.05% TFA in water and Mobile phase B consists of 0.05% TFA in ACN. Elute samples with a gradient of 10% B to 50% B at 20 min to 95% B at 25 min. For system 1, prepare a 0.8 mg/mL of standard solution by dissolving 40 mg of sample and dilute to 50 mL with the diluent of 60 ACN/40 water.

HPLC Method 2 utilizes the following conditions: Agilent 1260 HPLC system with UV detector at 270 nm with a Waters Cortecs C18+, 4.6×100 mm, 2.7 µm column with a column temperature of 45° C. with a flow rate of 0.8 mL/min and injector volume of 2 µl. Mobile phase A consists of 0.1% TFA in water:ACN:MeOH=90:2:8, v/v/v with an example being mix water (1800 mL) and mobile phase B (200 mL). Accurately transfer TFA (2.0 mL) and mix well. Mobile phase B consists of ACN:MeOH=20:80, v/v with an example being mix well ACN (400 mL) and MeOH (1600 mL) and degas by ultrasonication. Elute samples with a gradient of 75% A and 25% B to 10% A and 90% B over 30 min. For system 2, prepare the compounds in a 0.5 mg/mL solution by dissolving 50 mg of sample and dilute with a 1/1 solution of ACN/water to 100 mL.

HPLC Method 1 and HPLC Method 2 can be used to determine the percent area (% area) of the compounds of Formula A, Formula B, or Formula C, as well as the dihydroquinoline or quinoline based impurities. As used herein, "% area" refers to the percent area obtained using HPLC Method 1 or HPLC Method 2, or both. For the avoidance of doubt, the % area of the compounds of Formula A plus the % area of any contaminants or impurities is always less than or equal to 100% area; the % area of the compounds of Formula B plus the % area of any contaminants or impurities is always less than or equal to 100% area; and the % area of the compounds of Formula C plus the % area of any contaminants or impurities is always less than or equal to 100% area.

Figure 2:
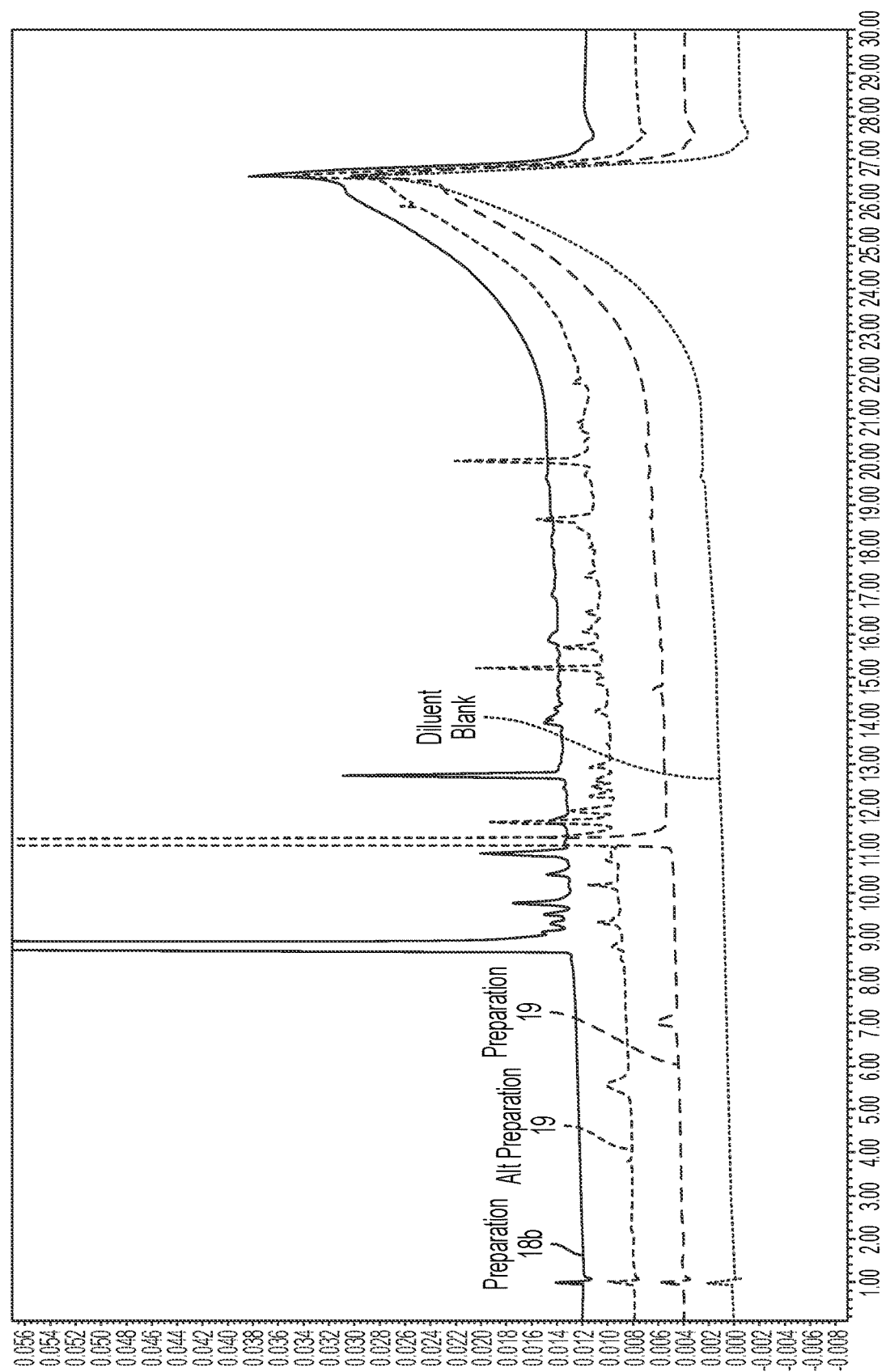
FIG. 2 is expanded version of FIG. 1.

FIGS. 1 and 2 show a peak at about 8.8 min for Preparation 18b and also in Alternate Preparation 19 utilizing chromatography system 1. This peak is the main product of the Preparation 18b reaction. The peak at about 8.8 min is not seen in Preparation 19 sample. The % area of the peak at 8.8 min in the Alternate Preparation 19 is 0.23%.

Figure 3:
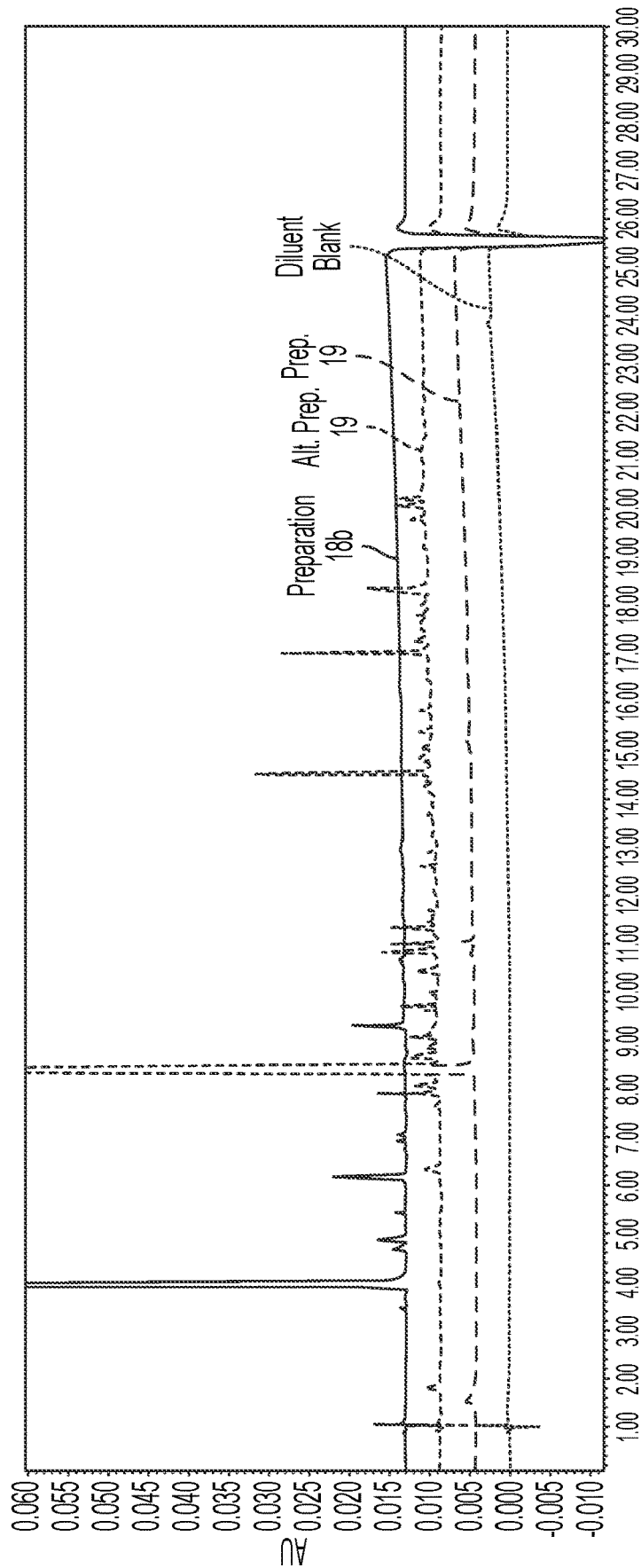
FIG. 3 is chromatography overlay of Preparation 18b, Preparation 19, and Alternate Preparation 19 utilizing chromatography system 2.

FIG. 3 shows a peak at about 5.2 min for Preparation 18b and barely visible in Preparation 19 utilizing chromatography system 2. The area of the peak at about 5.2 min is not seen in Preparation 19 sample. The % area of the peak at 5.2 min in the Alternate Preparation 19 is <0.05% area, which is below the limit of quantitation, for the method described herein. The differences in the % area for the different systems can be explained by the differences in response factors of the compounds for UV 245 nm in system 1 vs UV 270 nm in system 2.

Preparation 19 was used to synthesize several batches of (R)-5-(4-(2-(3-(fluoromethquinolinedin-1-yl)ethoxy)phenyl)-8-(trifluoromethyl)-5H-[1]benzopyrano[4,3quinolinelin-2-ol having the following purity (% area).

| Batch No. | Purity (% area) |
|---|---|
| 1 | 99.7% |
| 2 | 98.8% |
| 3 | 99.3% |
| 4 | 99.2% |
| 5 | 99.5% |

In one embodiment, a compound of formula B or a pharmaceutically acceptable salt thereof, is at least 98.5% area, at least 98.6% area, at least 98.7% area, at least 98.8% area, at least 98.9% area, at least 99.0% area, at least 99.1% area, at least 99.2% area, at least 99.3% area, at least 99.4% area, at least 99.5% area, at least 99.6% area, at least 99.7% area, or at least 99.8% area. In an embodiment, the pharmaceutically acceptable salt is the tosylate salt.

Biological Assays

ERα Degradation High Content Imaging Assays in MCF7 Cells

Cells were fixed by adding 14% paraformaldehyde (10 µL) for 30 min at RT. The cells were washed once with PBS (20 µL) and incubated with PBS (20 µL per well) containing 0.5% (v/v) TWEEN® 20 for 1 h. Cells were washed with PBS containing 0.05% TWEEN® 20 (2×) and blocked with 3% BSA in PBS containing 0.05% TWEEN® and 0.1% TRITON™ X-100 (20 µL/well) for 1 h at RT. A 1:500 dilution of Primary antibody (20 µL) (ERα (Clone SP1) monoclonal rabbit antibody #RM-9101-S, Thermo Scientific) in 1% BSA in PBS containing 0.05% TWEEN® 20 was added, the plates were sealed and incubated overnight at 4° C. The following day the cells were washed with PBS containing 0.05% TWEEN® 20 (2×) and incubated with secondary antibody (20 L/well) (1:1000 dilution, Goat anti-rabbit IgM ALEXA FLUOR™ 488) in PBS 1% BSA for 105 min at RT. After incubation plates were washed with PBS (2×20 µL), and PBS (20 µL) containing RNase (Sigma) (50 µg/mL) and 1:1000 propidium iodide dilution was added per well. Plates were sealed and incubated 1 h at RT (preserved from light). The plates were scanned with ACUMEN EXPLORER™ [Laser-scanning fluorescence microplate cytometer manufactured by TTP LABTECH LTD] to measure ERa. Image analysis was based on cellular fluorescent signals for identifying positive cells. Estrogen receptor positive cells were identified by mean intensity. Total intensity at 575-640 nm from propidium iodide/DNA was used to identify individual cells. Assay output was % estrogen receptor positive cells. The $IC_{50}$ was determine by curve fitting to a four-parameter logistic for each output using GENE DATA™. Raw data (FLU) were plotted as nonlinear regression through GENEDATA SCREENER© tool. Data was analyzed using a 4-parameter nonlinear logistic equation (four-parameter logistic concentration-response curve): Y=bot+[(top-bot)/1+(x/$IC_{50}$) slope] where Y=% inhibition, x=concentration yielding y % inhibition, Bottom=minimum value of y attained by curve, Top=maximum value of y attained by curve and Slope=steepness of curve at $IC_{50}$. % Inh=[(median Max−x/median Max−median Min)]×100. The results are shown in Table 2 of the SERD contaminants and comparable compounds of the synthesis to Formula A indicate that intermediates in the process of Formula A are not active SERD compounds at the concentration tested. In Table 2, compounds having a Relative IC50 of >2.00 µM are inactive.

TABLE 2

Rel IC$_{50}$ values in ERα degradation High Content Imaging assays in MCF7 ESR1 Wild Type cells
hERα Degradation Cell Assay in MCF7 Cells

| Compound | Relative IC$_{50}$ (μM) |
| --- | --- |
| Example 1 | 0.00321 ± 0.00138, n = 9* |
| Preparation 12 | >2.00, n = 2 |
| A-1 | 0.126 ± 0.0442, n = 4 |
| A-2 where R$_1$ = H and R$_2$ = CF$_3$ | 0.00216 + 0.00096, n = 15 |

TABLE 2-continued

Rel IC$_{50}$ values in ERα degradation High Content Imaging assays in MCF7 ESR1 Wild Type cells
hERα Degradation Cell Assay in MCF7 Cells

| Compound | Relative IC$_{50}$ (μM) |
| --- | --- |
| Preparation 13, racemic | >2.00, n = 2 |
| 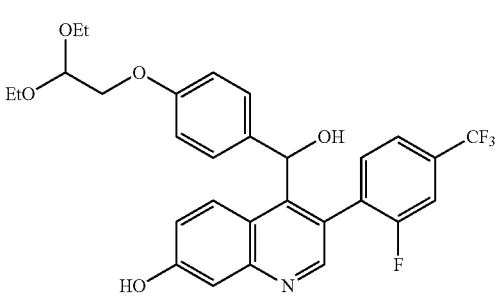 | |
| Preparation 15, racemic | 0.278 ± 0.126, n = 5 |
| 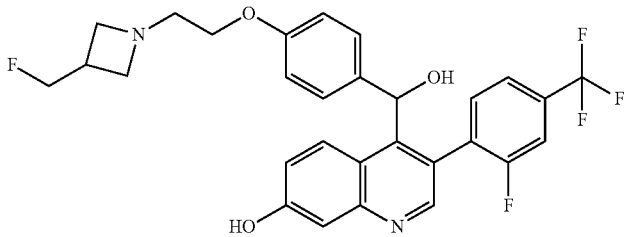 | |
| Preparation 17, racemic | >2.00, n = 2 |
| 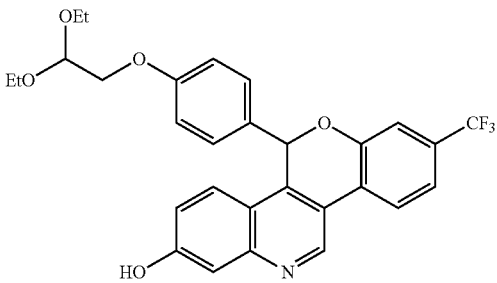 | |
| Preparation 18, racemic | >2.00, n = 2 |
| 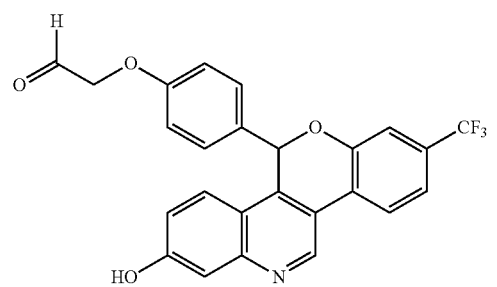 | |

*Relative IC$_{50}$ (μM) for the non-salt compound was reported in U.S. Pat. No. 10,654,866 as 0.003088 + 0.001523, n = 19.

OTHER EMBODIMENTS

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

All patents and publications mentioned in this specification are herein incorporated by reference to the same extent as if each independent patent and publication was specifically and individually indicated to be incorporated by reference.

What is claimed is:

1. A process for preparing a compound of Formula A:

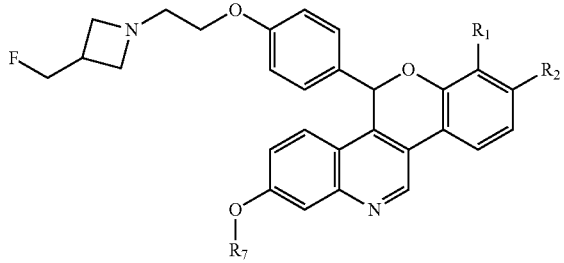

or a pharmaceutically acceptable salt thereof, wherein either $R_1$ or $R_2$ is independently Cl, F, —$CF_3$, or —$CH_3$, and the other is H; and $R_7$ is H or PG, wherein the process comprises reacting a compound of structure 8:

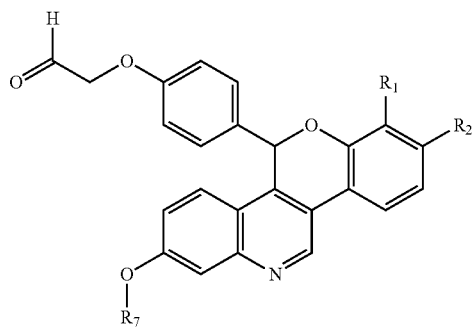

or a salt thereof, wherein $R_7$ is PG or H; wherein PG is an alcohol protecting group, in a solvent with an amine of structure 9

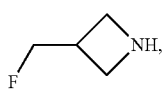

or a salt thereof, and a reducing agent.

2. The process of claim 1, wherein the reducing agent is STAB, $LiBH_4$, $NaBH_4$, $NaBH_3CN$ or pyridine borane.

3. The process of claim 1, comprising preparing a compound of structure 8, or a salt thereof, the process comprising reacting a compound of structure 7

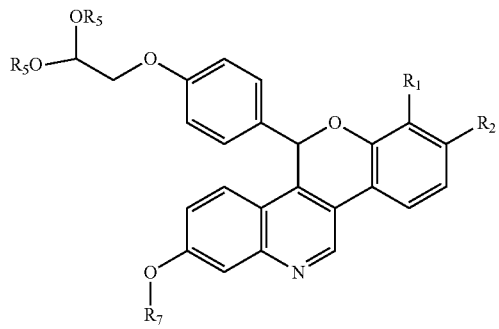

with an acid, wherein each $R_5$ is independently $C_1$-$C_6$ alkyl or the two $R_5$ groups combined are —$CH_2CH_2$— or —$CH_2CH_2CH_2$—.

4. The process of claim 3, wherein the acid comprises HCl, $H_2SO_4$, p-TsOH, methanesulfonic acid, trifluoromethanesulfonic acid, acetic acid, or trichloroacetic acid.

5. The process of claim 3, wherein the reaction is performed in a solvent and the solvent comprises water.

6. The process according to claim 3 comprising preparing a compound of structure 7, or a salt thereof, the process comprising reacting a compound of structure 6

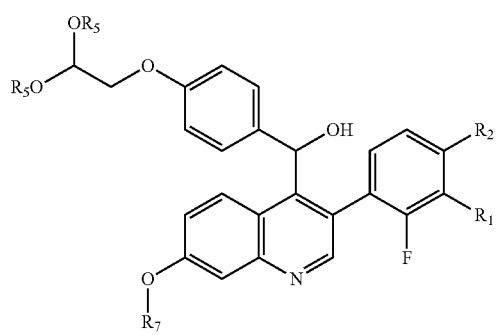

with a base.

7. The process of claim 6, wherein the base comprises $Cs_2CO_3$, NaH, sodium tert-butoxide, NaOH, LiOH, KOH, sodium tert-pentoxide, potassium tert-pentoxide, or DBU.

8. The process according to claim 6 comprising preparing a compound of structure 6, or a salt thereof, the process comprising reacting a compound of structure 4

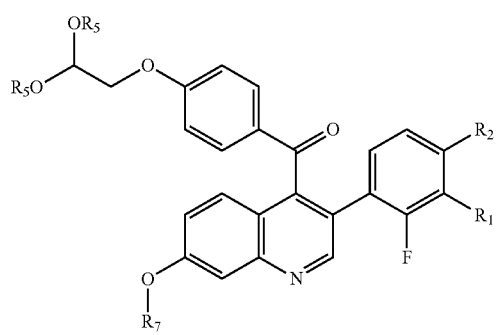

with a reducing agent.

9. The process according to claim 8, wherein the ketone reducing agent comprises $LiA_1H_4$, $NaBH_4$, or borane-ligand, where the ligand is THF, $Me_2S$, catechol, or N,N-diethylaniline.

10. The process according to claim 8, comprising preparing a compound of structure 4, or salt thereof, the process comprising reacting a compound of structure 3

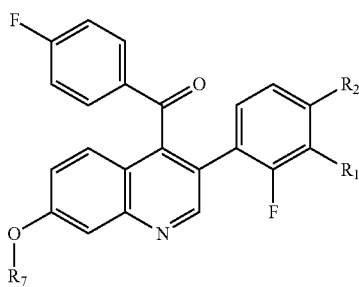

with HOCH$_2$CH(OR$_5$)$_2$.

11. The process according to claim 10, comprising preparing a compound of structure 3, or salt thereof, the process comprising a cross-coupling reaction between a compound of structure 1

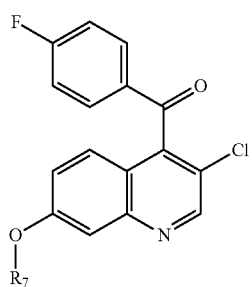

and a compound of structure 2

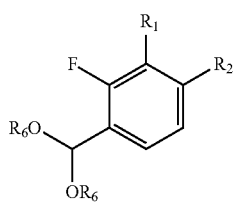

wherein R$_6$ can be hydrogen or alkyl or a structure where the two R$_6$ groups are joined by at least two carbons, to form dioxaborolanes or dioxaborinanes, in the presence of a catalyst.

12. The process of claim 11, wherein the catalyst comprises a transition metal catalyst.

13. The process of claim 12, wherein the transition metal catalyst comprises a Pd catalyst.

14. The process according to claim 1, wherein the compound of structure 8 is the compound of structure 8B:

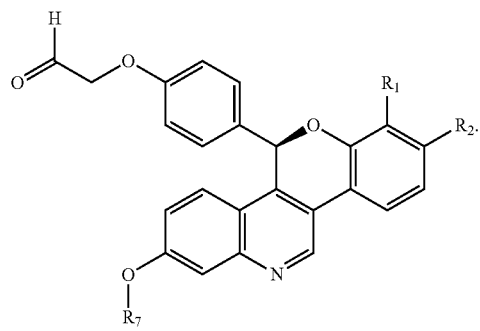

15. The process according to claim 3, wherein the compound of structure 7 is the compound of structure 7B:

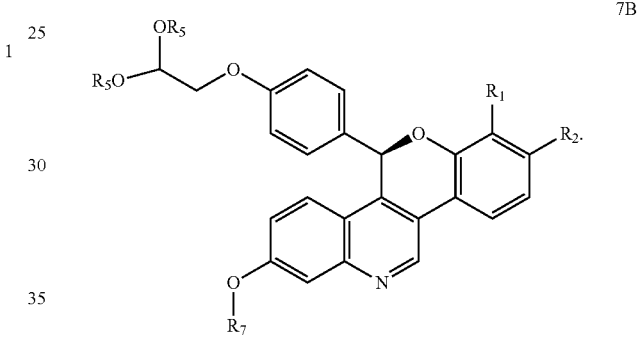

16. The process according to claim 6, wherein the compound of structure 6 is the compound of structure 6B:

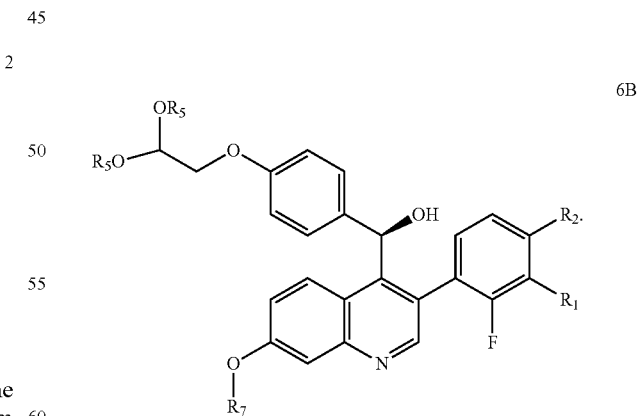

17. The process according to claim 1, wherein the compound of Formula A or the pharmaceutically acceptable salt thereof is a compound of Formula B

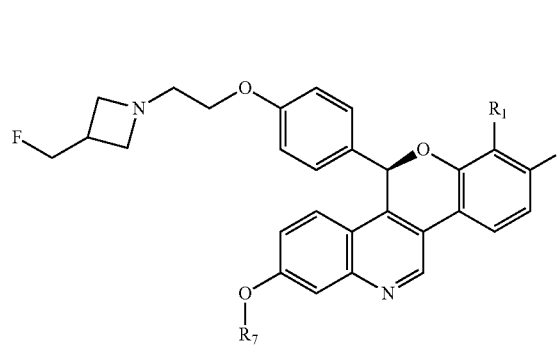

or a pharmaceutically acceptable salt thereof, wherein either $R_1$ or $R_2$ is independently Cl, F, —$CF_3$, or —$CH_3$, and the other is H; and $R_7$ is H or PG.

18. The process of claim 1, wherein the compound, or the pharmaceutically acceptable salt thereof, is selected from:

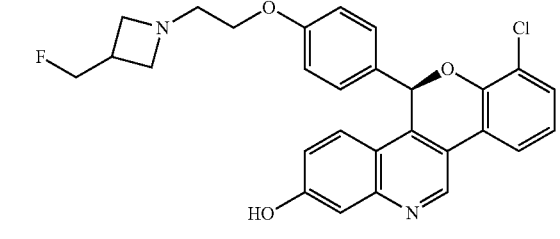

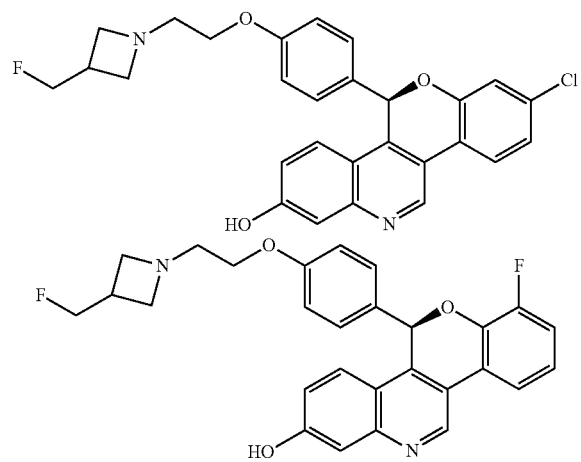

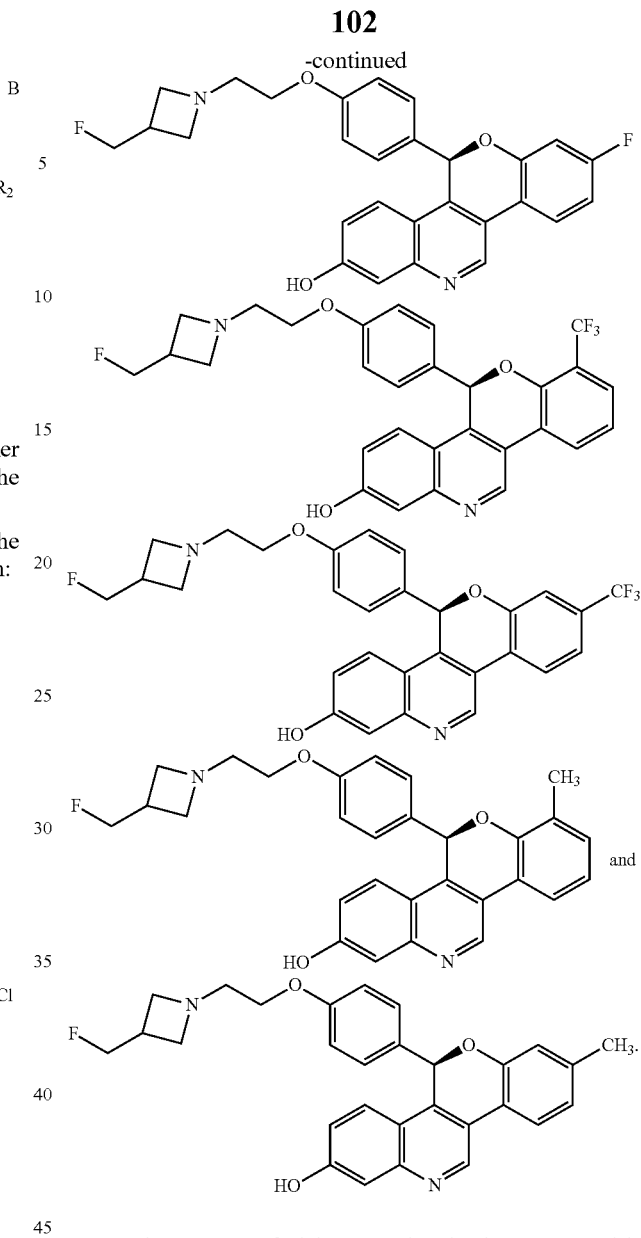

19. The process of claim 18, wherein the compound is provided as the tosylate salt.

20. A compound that is (R)-2-(4-(2-hydroxy-8-(trifluoromethyl)-5H-chromeno[4,3-c]quinolin-5-yl)phenoxy)ethane-1,1-diol or a salt thereof.

* * * * *

UNITED STATES PATENT AND TRADEMARK OFFICE
CERTIFICATE OF CORRECTION

PATENT NO. : 11,926,634 B2
APPLICATION NO. : 18/160457
DATED : March 12, 2024
INVENTOR(S) : Arguelles Delgado et al.

It is certified that error appears in the above-identified patent and that said Letters Patent is hereby corrected as shown below:

In the Claims

In Claim 9, delete "$Li_1Al_1H_4$," and insert -- $Li_1AlH_4$, --.

Signed and Sealed this
Twenty-third Day of July, 2024

Katherine Kelly Vidal
*Director of the United States Patent and Trademark Office*